(12) United States Patent
Fukui et al.

(10) Patent No.: US 11,213,020 B2
(45) Date of Patent: Jan. 4, 2022

(54) ATOPIC DERMATITIS MODEL NON-HUMAN ANIMAL AND USE THEREOF

(71) Applicant: KYUSHU UNIVERSITY, NATIONAL UNIVERSITY CORPORATION, Fukuoka (JP)

(72) Inventors: Yoshinori Fukui, Fukuoka (JP); Kazuhiko Yamamura, Fukuoka (JP); Takehito Uruno, Fukuoka (JP); Masutaka Furue, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 360 days.

(21) Appl. No.: 16/079,244

(22) PCT Filed: Feb. 24, 2017

(86) PCT No.: PCT/JP2017/007198
§ 371 (c)(1),
(2) Date: Mar. 15, 2019

(87) PCT Pub. No.: WO2017/146227
PCT Pub. Date: Aug. 31, 2017

(65) Prior Publication Data
US 2019/0191675 A1    Jun. 27, 2019

(30) Foreign Application Priority Data

Feb. 25, 2016 (JP) .............................. JP2016-034510

(51) Int. Cl.
| | | |
|---|---|---|
| *A01K 67/027* | (2006.01) | |
| *G01N 33/50* | (2006.01) | |
| *C12Q 1/66* | (2006.01) | |
| *C12Q 1/02* | (2006.01) | |
| *A61K 45/00* | (2006.01) | |
| *C12N 15/09* | (2006.01) | |
| *C12N 5/10* | (2006.01) | |
| *G01N 33/53* | (2006.01) | |
| *C12Q 1/68* | (2018.01) | |
| *A61K 49/00* | (2006.01) | |

(52) U.S. Cl.
CPC ........ *A01K 67/0276* (2013.01); *A01K 67/027* (2013.01); *A61K 45/00* (2013.01); *A61K 49/0008* (2013.01); *C12N 5/10* (2013.01); *C12N 15/09* (2013.01); *C12Q 1/02* (2013.01); *C12Q 1/66* (2013.01); *C12Q 1/68* (2013.01); *G01N 33/50* (2013.01); *G01N 33/505* (2013.01); *G01N 33/53* (2013.01); *A01K 2217/056* (2013.01); *A01K 2227/105* (2013.01); *A01K 2267/03* (2013.01); *G01N 2333/54* (2013.01)

(58) Field of Classification Search
CPC ........ A01K 2267/0368; A01K 67/0276; A01K 2217/056; A01K 2267/03; A01K 2267/0387; C12N 5/10; C12N 15/09
See application file for complete search history.

(56) References Cited

FOREIGN PATENT DOCUMENTS

| | | |
|---|---|---|
| EP | 2942356 | 11/2015 |
| JP | 2011-516065 A | 5/2011 |
| WO | WO2009/123764 | 10/2009 |

OTHER PUBLICATIONS

Helen et al Curr Opinion Allergy Clin Immuno, 10, 6, 515-520 (Year: 2010).*
Harada et al Blood, 119, 4451-4461 (Year: 2012).*
Zhang et al N. Engl. J. Med., 361 (21), 2046-2055, (Year: 2009).*
Harada et al Blood, 119 (19), 4451-4461 (Year: 2012).*
Munoz et al. Stem Cell Rev. and Rep., vol. 5, 6-9 (Year: 2009).*
Tong et al. Nature, vol. 467(7312), pp. 211-213 (Year: 2010).*
Hong et al. Stem Cells and Development, vol. 21(9), pp. 1571-1586 (Year: 2012).*
Brevini et al., Theriogenology, vol. 74, pp. 544-550 (Year: 2010).*
Paris et al. Theriogenology, vol. 74, pp. 516-524 (Year: 2010).*
Ezashi et al Annu. Rev. Anim. Biosci. 4:223-53 (Year: 2016).*
Patil et al., Indian Journal of Public Health research & Development, vol. 2, No. 1, 106-109 (Year: 2011).*
Khodarovich et al., Applied Biochemistry and Microbiology, vol. 49, No. 9, 711-722 (Year: 2013).*
Selsby et al., (ILAR Journal, vol. 56, No. 1, p. 116-126 (Year: 2015).*
Yang et al., PNAS, 113(41), E6209-E6218, 1-10 (Year: 2016).*
Su et al Curr Opin Allergy Clin Immul., 10(61), pp. 515-520 (Year: 2010).*
Kaye et al. Journal of Immunology, 3342-3353, (Year: 1992).*
Udea et al Nature Communication, 3, 1098, 1-13), (Year: 2012).*
Ueda et al Journal of Clinical and Experimental Medicine, 247, 6, 565-566, (Year: 2013).*
Nobb et al. Acta Derm Vererol, 92, 24-28 (Year: 2012).*
PCT Search Report and Written Opinion for PCT/JP2017/007198, completed May 10, 2017.
Zhang, Qian, et al., "Combined Immunodeficiency Associated with DOCK8 Mutations," 2009, New England J. Med., vol. 361, No. 21, pp. 2046-2055.
Harada, Yosuke, et al., "DOCK8 is a Cdc42 activator critical for interstitial dendritic cell migration during immune responses." 2012, Blood, vol. 119, No. 19, pp. 4451-4461.
Ueda, Yoshihiro, et al., "Mst1 ni yoru Kyosen Saibo no Integrin Secchaku Seigyo to Sentaku Kiko," 2013, Journal of Clinical and Experimental Medicine, vol. 247, No. 6, pp. 565-566.
Su, Helen C., et al., "DOCK8 Deficiency," 2011, Annals of the New York Academy of Sciences, No. 1246, pp. 26-33.

(Continued)

*Primary Examiner* — Anoop K Singh
(74) *Attorney, Agent, or Firm* — Barnes & Thornburg LLP

(57) ABSTRACT

An atopic dermatitis model non-human animal, containing a gene mutation in which a complex containing dedicator of cytokinesis 8 (DOCK8) protein, mammalian STE20-like kinase 1 (MST1) protein, and endothelial PAS domain protein 1 (EPAS1) protein is not formed in CD4+ T cells.

2 Claims, 21 Drawing Sheets

Specification includes a Sequence Listing.

(56) References Cited

OTHER PUBLICATIONS

Yamamura, Kazuhiko, et al., "The Transcription Factor EPAS1 Links DOCK8 Deficiency to Atopic Skin Inflammation via IL-31 Induction," 2017, Nature Communications, vol. 8, No. 13946.
Chan, W.K., "Knockdown of Dock8 in Zebrafish Reveals a Role for Dock8 in Extra-Lymphoid Tissue Development," J Allergy Clin Immunol (Abstract 525), Feb. 2012, p. 138.
Kaye, J. et al., "Selective development of CD4+ T cells in transgenic mice expressing a class II MHC-restricted antigen receptor," Nature, vol. 341, Oct. 26, 1989, 746-749.
Kaye, J. et al., "Involvement of the Same Region of the T Cell Antigen Receptor in Thymic Selection and Foreign Peptide Recognition," The Journal of Immunology, vol. 148, No. 11, Jun. 1, 1992, 3342-3353.
Krishnaswamy, J.K. et al., "Coincidental loss of DOCK8 function in NLRP10-deficient and C3H/HeJ mice results in defective dendritic cell migration," PNAS, vol. 112, No. 10, Mar. 10, 2015, 3056-3061.
Randall, K.L. et al., "DOCK8 mutations cripple B cell immune synapse, germinal centers and long-lived antibody production," Nat Immunol. Dec. 2009: 10(12): 1283-1291.
Randall, K.L., "DOCK8 deficiency impairs CD8 T cell survival and function in humans and mice," The Journal of Experimental Medicine, vol. 208, No. 11, Oct. 17, 2011 (Oct. 17, 2011), pp. 2305-2320.
Su, Helen C., DOCK8 (Dedicator of cytokinesis 8) deficiency, Curr Opin Allergy Clin Immunol., vol. 10, No. 6, Dec. 1, 2010, pp. 515-520.
EP Search Report for EP Application 17756661.9, dated Nov. 18, 2019.

\* cited by examiner

SEQUENCE LISTING

```
<160> NUMBER OF SEQ ID NOS: 33

<210> SEQ ID NO 1
<211> LENGTH: 16
<212> TYPE: PRT
<213> ORGANISM: Manduca sexta

<400> SEQUENCE: 1

Ala Asn Glu Arg Ala Asp Leu Ile Ala Tyr Leu Lys Gln Ala Thr Lys
1               5                   10                  15

<210> SEQ ID NO 2
<211> LENGTH: 1491
<212> TYPE: DNA
<213> ORGANISM: Homo sapiens

<400> SEQUENCE: 2
agcatagtga tttgtgcctg tggtcccagc tatttgggag gctgaggtag gaggatcact        60
tgagcccagg ggatcggggc tgccgtgagt tgtgatgatg ccactgcact ctggcctggg       120
tgacagaatg agaccctgtc tcaaaaaaaa aaaaaaagaa agaaaaagaa agctaatgaa       180
```

```
cttagaaata gtttctaagg ccagagtggt ggctcgcacc tgtaatccca gcactttgag         240
aggcggaggc aggtggatca caaggtcagg cgtttgagac cagcctggcc aacatagtga         300
accccgtctc tactaaaaat acaaaaatta gctgtgcgtg gtggtgggcg cctgtaatcc         360
cagccactca ggaggctgag gcaagagaat tgcttgaacc tgggaagtgg aggttgcagt         420
gagccgagat tgcgctactg cactccagcc caggcgacag agcaagactc tgtctcaaaa         480
aaaaagaaag aaagaaagaa agaaagaaaa gcaataaagt ttctaggctg cgcagtggc         540 tcatgcctgt aattccagca ctttgggaag ccgaggcagg cagatcacct gaggtcagga         600
gttagagacc agcttgacca acatggcgaa accccatttc tactaaaaat acaaaaatta         660
gctgggcatg gtggcacgtg cctgtagtcc cagctacttg ggaggctgag actgaggcat         720
gagaattgct tgagcccagg agacagaggt tgcagtgatc acgccaccgc actccagcct         780
gggtgacaga gcaagactcc atctcaaaaa aaaaaaaaag aaaaaagata tgaacaagga         840
tttcaagcaa taactctgga tcacagtctc tggttctggg ccctgagatt gcagaggcac         900
gatggagagt ccagtgatgt ccaaggccac atggagttga gatgaagcct tcgacccgcc         960
acattcacag cagttatggg gccgtccctg cacaccggcg tgggcatatg ctgcagaaat        1020
ttccagagat accgcattct gcacatctca tgccggcttc gcatttcctc cccagaaatt        1080
ccctgtggcc gctggccttg aactcctgga agtcacccgc tccttggtgg tatggtcgtg        1140
tctgtcaacc ctgggcttca aaattttgtc tagtcaaatc aacaggctcc ttccaagaag        1200
aatggcaaag atgcattcat gtgccttctt gtgaagtatg tgtgtgtctg agtcaggcat        1260
ctgcccacct ggagggtaac ctcagcattt ccattcagcc ctttcactca gccgtggcca        1320
gtagaacttt tgagtgtttt ctggagaaaa gctgagtaaa tggttttgcc atgggcggga        1380
cgctgactgc tctttctcct caccctggcc ctttatatac ctccaggcag ccatggcgaa        1440
cacatctggc tccagaagcc cccactgaag ctggccttgc tctctctcgc c                 1491
```

<210> SEQ ID NO 3
<211> LENGTH: 1367
<212> TYPE: DNA
<213> ORGANISM: Mus musculus

<400> SEQUENCE: 3

```
agggctctgg gtgtgtggtg gaagtgttcc atcagtgatc aattagccca gcctaacaaa          60
tacttcattt ttttctttga tagacagctg ctctctgcag tcctgcctgg gctgccactc         120
actgtgagac aaagctggcc taactttgca tcagtcttcc ctcttctgtc tcctgaatgt         180
tgggattaca ggcatgagct gccatgcctg gctgaacgac tctttatttc aatttagtta         240
acgtgttcgg gtgtttgatc agcatgtatg tctgcacagt ttgtgtatgc ctggtgccca         300
cagaggctcg agagtgtcag attccccccca aaactggagt tacagttttg agccgcccca         360
tgcttgatag caatcaaacc tgggtcctct gaaagagcat ccagtgcatg taaccactga         420
accatctctc caaaccatga acatcacttt aatttttttt aatagttaaa ggatattttg         480
attctaaaga tgtaaaagaa cgtctcacct attttgaaat ttggtaataa atgtttcttc         540
aaagcttaaa aaaattagtt caggtttttt ttttttttca gtcagtgatt tgctaagctg         600
cccaaactgg cttagaattt gtgaccctct tgtctcagca tactgagtgt taagattaca         660
agtgcacccc ctacccagtt cccataatta actgatccac ccccaccccc atcccacccc         720
actcccattg cctgggcaag taactcttga gccccattct ggttctagag tctgaagtca         780
```

-continued

| | |
|---|---|
| caaaggtgca ggtgagaacg caaggacaag ggcaggccct ggagcacaga tgccttctcc | 840 |
| ttatgccttc cctgtgttca ctagagccat cccccctgcct ccggaattcc cacagatgga | 900 |
| tcgctctgtg gcttcttaaa acttccctgc agggcactga ccctcagccc ctctaagtca | 960 |
| cttcttcccc agtgattgta cttttcaatc gggcttcaaa cttcctctc attaaatcag | 1020 |
| caagcacttt ccaagaaaag agagatgctc aagatgcctt cctgtgtggt atgtgtatgc | 1080 |
| gtttgtgtgt gtgcacgcat gtgtgtcat gtgactcaat cttctgcctt gccttgaggg | 1140 |
| taacctcagc atttccttcc agccctgctt tccccaggcc gagccgaggc tggcaacctt | 1200 |
| ttgaaaatgt tttctggaga aaagctgagc aatggttttg ccatgggcgg gcctttgatc | 1260 |
| tgcttcctca tgacaaccct ttatatattg cctggtggcc atggcgaaca caccaggctc | 1320 |
| cagagaccac aggcaaagcg ggccttcctc actctcttac cgtcgcc | 1367 |

```
<210> SEQ ID NO 4
<211> LENGTH: 17
<212> TYPE: PRT
<213> ORGANISM: Gallus gallus

<400> SEQUENCE: 4

Ile Ser Gln Ala Val His Ala Ala His Ala Glu Ile Asn Glu Ala Gly
1               5                   10                  15

Arg

<210> SEQ ID NO 5
<211> LENGTH: 21
<212> TYPE: DNA
<213> ORGANISM: Mus musculus

<400> SEQUENCE: 5
cagtatgact ccactcacgg c                                           21

<210> SEQ ID NO 6
<211> LENGTH: 21
<212> TYPE: DNA
<213> ORGANISM: Mus musculus

<400> SEQUENCE: 6
tcacgccaca gctttccaga g                                           21

<210> SEQ ID NO 7
<211> LENGTH: 30
<212> TYPE: DNA
<213> ORGANISM: Mus musculus

<400> SEQUENCE: 7
aaacaagagt ctcaggatct ttataacaac                                  30

<210> SEQ ID NO 8
<211> LENGTH: 21
<212> TYPE: DNA
<213> ORGANISM: Mus musculus

<400> SEQUENCE: 8
agccatctta tcacccaaga a                                           21

<210> SEQ ID NO 9
<211> LENGTH: 20
<212> TYPE: DNA
<213> ORGANISM: Mus musculus
```

<400> SEQUENCE: 9
gagcaaaggg tccctgtctc                                                    20

<210> SEQ ID NO 10
<211> LENGTH: 20
<212> TYPE: DNA
<213> ORGANISM: Mus musculus

<400> SEQUENCE: 10
aattcatcgg gggccatgtt                                                    20

<210> SEQ ID NO 11
<211> LENGTH: 20
<212> TYPE: DNA
<213> ORGANISM: Mus musculus

<400> SEQUENCE: 11
ggcagcgtgt acaaggctat                                                    20

<210> SEQ ID NO 12
<211> LENGTH: 20
<212> TYPE: DNA
<213> ORGANISM: Mus musculus

<400> SEQUENCE: 12 atatggggc tttccttcag                                                     20

<210> SEQ ID NO 13
<211> LENGTH: 19
<212> TYPE: DNA
<213> ORGANISM: Homo sapiens

<400> SEQUENCE: 13
gtgaaggtcg gagtcaacg                                                     19

<210> SEQ ID NO 14
<211> LENGTH: 21
<212> TYPE: DNA
<213> ORGANISM: Homo sapiens

<400> SEQUENCE: 14
ggtgaagacg ccagtggact c                                                  21

<210> SEQ ID NO 15
<211> LENGTH: 23
<212> TYPE: DNA
<213> ORGANISM: Homo sapiens

<400> SEQUENCE: 15
tggacctcgc actaaaatca ttg                                                23

<210> SEQ ID NO 16
<211> LENGTH: 22
<212> TYPE: DNA
<213> ORGANISM: Homo sapiens

<400> SEQUENCE: 16
cgaaaggaag agatggcctt aa                                                 22

<210> SEQ ID NO 17
<211> LENGTH: 20
<212> TYPE: DNA
<213> ORGANISM: Homo sapiens

```
<400> SEQUENCE: 17
gcaactcctg tcttgcattg                                              20

<210> SEQ ID NO 18
<211> LENGTH: 20
<212> TYPE: DNA
<213> ORGANISM: Homo sapiens

<400> SEQUENCE: 18
cagttctgtg gccttcttgg                                              20

<210> SEQ ID NO 19
<211> LENGTH: 20
<212> TYPE: DNA
<213> ORGANISM: Mus musculus

<400> SEQUENCE: 19
ctggtgaaaa ggacctctcg                                              20

<210> SEQ ID NO 20
<211> LENGTH: 26
<212> TYPE: DNA
<213> ORGANISM: Mus musculus

<400> SEQUENCE: 20
tgaagtactc attatagtca agggca                                       26

<210> SEQ ID NO 21
<211> LENGTH: 30
<212> TYPE: DNA
<213> ORGANISM: Mus musculus

<400> SEQUENCE: 21
aaacaagagt ctcaggatct ttataacaac                                   30

<210> SEQ ID NO 22
<211> LENGTH: 21
<212> TYPE: DNA
<213> ORGANISM: Mus musculus

<400> SEQUENCE: 22
acggcagctg tattgattcg t                                            21

<210> SEQ ID NO 23
<211> LENGTH: 25
<212> TYPE: DNA
<213> ORGANISM: Mus musculus

<400> SEQUENCE: 23
ccaagaacac cacagagagt gagct                                        25

<210> SEQ ID NO 24
<211> LENGTH: 25
<212> TYPE: DNA
<213> ORGANISM: Mus musculus

<400> SEQUENCE: 24
gactcattca tggtgcagct tatcg                                        25

<210> SEQ ID NO 25
<211> LENGTH: 23
<212> TYPE: DNA
```

```
<213> ORGANISM: Mus musculus

<400> SEQUENCE: 25
cctgagcagg atggagaatt aca                                    23

<210> SEQ ID NO 26
<211> LENGTH: 19
<212> TYPE: DNA
<213> ORGANISM: Mus musculus

<400> SEQUENCE: 26
tccagaacat gccgcagag                                         19

<210> SEQ ID NO 27
<211> LENGTH: 60
<212> TYPE: DNA
<213> ORGANISM: Mus musculus

<400> SEQUENCE: 27
gatctcaccg ccagattgtt gcaatcaagc cgaagcttga ttgcaacaat ctggctttta    60

<210> SEQ ID NO 28
<211> LENGTH: 60
<212> TYPE: DNA
<213> ORGANISM: Mus musculus

<400> SEQUENCE: 28
agcttaaaag ccagattgtt gcaatcaagc ttcggcttga ttgcaacaat ctggcggtga    60

<210> SEQ ID NO 29
<211> LENGTH: 20
<212> TYPE: PRT
<213> ORGANISM: Homo sapiens

<400> SEQUENCE: 29

Arg Asp Ser Phe His Arg Ser Ser Phe Arg Lys Cys Glu Thr Gln Leu
1               5                   10                  15

Ser Gln Gly Ser
            20

<210> SEQ ID NO 30
<211> LENGTH: 28
<212> TYPE: DNA
<213> ORGANISM: Mus musculus

<400> SEQUENCE: 30
tgccatgggc gggcctttga tctgcttc                               28

<210> SEQ ID NO 31
<211> LENGTH: 28
<212> TYPE: DNA
<213> ORGANISM: Mus musculus

<400> SEQUENCE: 31
tgccatgggc gaagttttga tctgcttc                               28

<210> SEQ ID NO 32
<211> LENGTH: 20
<212> TYPE: DNA
<213> ORGANISM: Mus musculus

<400> SEQUENCE: 32
atcttctgcc ttgccttgag                                        20
```

```
<210> SEQ ID NO 33
<211> LENGTH: 20
<212> TYPE: DNA
<213> ORGANISM: Mus musculus

<400> SEQUENCE: 33
atgaggaagc agatcaaagg                                              20
```

ATOPIC DERMATITIS MODEL NON-HUMAN ANIMAL AND USE THEREOF

CROSS-REFERENCE TO RELATED APPLICATIONS

This application is the U.S. national phase of PCT/JP2017/007198, filed on Feb. 24, 2017, which claims the benefit of Japanese Patent Application Serial Number 2016-034510, filed on Feb. 25, 2016, the entire disclosures of both of which are incorporated herein by reference.

TECHNICAL FIELD

The present invention relates to an atopic dermatitis model non-human animal and use thereof. More specifically, the present invention relates to an atopic dermatitis model non-human animal, a potential drug target for an atopic dermatitis treatment, a method for screening a therapeutic agent for atopic dermatitis, a therapeutic agent for atopic dermatitis, and a non-human animal for developing an atopic dermatitis model animal.

Priority is claimed on Japanese Patent Application No. 2016-034510, filed on Feb. 25, 2016, the content of which is incorporated herein by reference.

BACKGROUND ART

Atopic dermatitis is a chronic inflammatory skin disease, and patients thereof are increasing all over the world. Atopic dermatitis is characterized by the formation of erythematous exudative lesions accompanied by inflammatory infiltrates composed mainly of CD4-positive ($CD4^+$) T cells.

Itching and scratching behavior play important roles in the onset and deterioration of skin inflammation, and therefore identification of a pruritogen is important for effective treatment strategies for atopic dermatitis. In addition, at present, interleukin (IL)-31 is considered to be a major pruritogen.

IL-31 is produced from activated helper type 2 ($T_H2$) $CD4^+$ T cells. Intradermal injection of IL-31 to mice and transgenic mice overexpressing IL-31 exhibit increased scratching behavior and cause severe dermatitis. In addition, it is known that in patients with atopic dermatitis, cutaneous lymphocyte antigen (CLA)-positive skin homing $CD4^+$ T cells produce IL-31, and the IL-31 concentration in serum correlates with the severity of the disease. Furthermore, a result of a phase II clinical trial revealed that the itching behavior is suppressed when an anti-IL-31 receptor antibody is administered to the patients with atopic dermatitis.

Therefore, IL-31 is a cytokine derived from T cells and has a close relationship with itching in atopic dermatitis.

Incidentally, a hyper IgE syndrome is a complex primary immunodeficiency disorder characterized by atopic dermatitis accompanied with high serum IgE levels and susceptibility to infections with extracellular bacteria. It has recently been reported that the autosomal recessive type of hyper IgE syndrome is caused mainly by mutations in the dedicator of cytokinesis 8 (DOCK8) gene (refer to, for example, NPL 1).

It is known that DOCK8 is an evolutionarily conserved guanine nucleotide exchange factor (GEF) for activating Cdc42. The present inventors generated DOCK8-knockout ($DOCK8^{-/-}$) mice and have revealed that DOCK8 is essential for interstitial migration of dendritic cells (refer to, for example, NPL 2).

CITATION LIST

Patent Literature

[NPL 1] Zhang Q, et al., Combined Immunodeficiency Associated with DOCK8 Mutations, N. Engl. J. Med., 361 (21), 2046-2055, 2009.

[NPL 2] Harada Y, et al., DOCK8 is a Cdc42 activator critical for interstitial dendritic cell migration during immune responses, Blood, 119 (19), 4451-4461, 2012.

SUMMARY OF INVENTION

Technical Problem

As seen above, IL-31 is the major pruritogen in atopic dermatitis, but a mechanism regulating IL-31 production by $CD4^+$ T cells remains unknown. An object of the present invention is to clarify the mechanism regulating IL-31 production and to provide an atopic dermatitis model non-human animal.

Solution to Problem

The present invention includes the following aspects.

[1] An atopic dermatitis model non-human animal, having a gene mutation in which a complex containing dedicator of cytokinesis 8 (DOCK8) protein, mammalian STE20-like kinase 1 (MST1) protein, and endothelial PAS domain protein 1 (EPAS1) protein is not formed in $CD4^+$ T cells.

[2] The atopic dermatitis model non-human animal according to [1], in which the gene mutation is knockout or knockdown of DOCK8 gene or MST1 gene.

[3] The atopic dermatitis model non-human animal according to [1] or [2], in which a rearranged T cell receptor (TCR) is expressed.

[4] The atopic dermatitis model non-human animal according to any one of [1] to [3], further having a genotype of $DOCK8^{-/-}$ TCR Tg or $MST1^{--}$ TCR Tg (herein, TCR Tg represents a rearranged TCR transgene).

[5] The atopic dermatitis model non-human animal according to [3] or [4], in which the TCR is AND.

[6] An atopic dermatitis model cell, having a gene mutation in which a complex containing DOCK8 protein, MST1 protein, and EPAS1 protein is not formed.

[7] The cell according to [6], in which the gene mutation is knockout or knockdown of DOCK8 gene or MST1 gene.

[8] A method for screening a therapeutic agent for atopic dermatitis, including: quantitatively determining a degree of scratching behavior of the non-human animal according to any one of [1] to [5] under administration of a test substance; and determining that the test substance is the therapeutic agent for atopic dermatitis in a case where the quantitatively determined degree of the scratching behavior is decreased when compared to a degree of the scratching behavior of the non-human animal under non-administration of the test substance.

[9] A method for screening a therapeutic agent for atopic dermatitis, including: stimulating TCR of $CD4^+$ T cells from a patient with atopic dermatitis, $DOCK8^{-/-}$-$CD4^+$ T cells, or $MST1^{-/-}$ $CD4^+$ T cells in the presence of a test substance to quantitatively determine an expression level of interleukin (IL)-31 by the $CD4^+$ T cells; and determining that the test substance is the therapeutic agent for atopic dermatitis in a case where the expression level of the IL-31 is decreased when compared to an expression level of the IL-31 in a case where the TCR of the CD4$^+$ T cells is stimulated in the absence of the test substance.

[10] A method for screening a therapeutic agent for atopic dermatitis, including: expressing EPAS1 gene in T cells in the presence of a test substance to quantitatively determine an expression level of IL-31; and determining that the test substance is the therapeutic agent for atopic dermatitis in a case where the expression level is decreased when compared to an expression level of the IL-31 in a case where the EPAS1 gene is expressed in the cells in the absence of the test substance.

[11] A method for screening a therapeutic agent for atopic dermatitis, including: expressing EPAS1 gene in cells into which a reporter construct in which a reporter gene is linked downstream of an IL-31 promoter is introduced in the presence of a test substance to quantitatively determine an expression level of the reporter gene; and determining that the test substance is the therapeutic agent for atopic dermatitis in a case where the expression level of the reporter gene is decreased when compared to an expression level of the reporter gene in a case where the EPAS1 gene is expressed in the cells in the absence of the test substance.

[12] A method for screening a therapeutic agent for atopic dermatitis, including: stimulating TCR of DOCK8$^{-/-}$ T cells or MST1$^{-/-}$ T cells in the presence of a test substance to quantitatively determine an expression level of IL-31; and determining that the test substance is the therapeutic agent for atopic dermatitis in a case where the expression level is decreased when compared to an expression level of the IL-31 in a case where the TCR of the cells is stimulated in the absence of the test substance.

[13] A method for screening a therapeutic agent for atopic dermatitis, including: stimulating TCR of DOCK8$^{-/-}$ T cells or MST1$^{-/-}$ T cells, into which a reporter construct in which a reporter gene is linked downstream of an IL-31 promoter is introduced in the presence of a test substance to quantitatively determine an expression level of the reporter gene; and determining that the test substance is the therapeutic agent for atopic dermatitis in a case where the expression level of the reporter gene is decreased when compared to an expression level of the reporter gene in a case where the TCR of the cells is stimulated in the absence of the test substance.

[14] A method for screening a therapeutic agent for atopic dermatitis, including: measuring a binding force between EPAS1 protein and DOCK8 protein in the presence of a test substance; and determining that the test substance is the therapeutic agent for atopic dermatitis in a case where the binding force is increased when compared to the binding force between the EPAS1 protein and the DOCK8 protein in the absence of the test substance.

[15] A method for screening a therapeutic agent for atopic dermatitis, including: measuring a binding force between EPAS1 protein and MST1 protein in the presence of a test substance; and determining that the test substance is the therapeutic agent for atopic dermatitis in a case where the binding force is increased when compared to the binding force between the EPAS1 protein and the MST1 protein in the absence of the test substance.

[16] A method for screening a therapeutic agent for atopic dermatitis, including: measuring a binding force between DOCK8 protein and MST1 protein in the presence of a test substance; and determining that the test substance is the therapeutic agent for atopic dermatitis in a case where the binding force is increased when compared to the binding force between the DOCK8 protein and the MST1 protein in the absence of the test substance.

[17] A method for screening a therapeutic agent for atopic dermatitis, including: measuring a binding force between EPAS1 protein and SP1 protein in the presence of a test substance; and determining that the test substance is the therapeutic agent for atopic dermatitis in a case where the binding force is decreased when compared to the binding force between the EPAS1 protein and the SP1 protein in the absence of the test substance.

[18] A method for screening a therapeutic agent for atopic dermatitis, including: expressing EPAS1 gene in DOCK8$^{-/-}$ cells or MST1$^{-/-}$ cells in the presence of a test substance to quantitatively determine the abundance of nuclear EPAS1 protein; and determining that the test substance is the therapeutic agent for atopic dermatitis in a case where the abundance of the nuclear EPAS1 protein is decreased when compared to abundance of the nuclear EPAS1 protein in a case where the EPAS1 gene is expressed in the cells in the absence of the test substance.

[19] A method for screening a therapeutic agent for atopic dermatitis, including: quantitatively determining an expression level of EPAS1 in cells in the presence of a test substance; and determining that the test substance is the therapeutic agent for atopic dermatitis in a case where the expression level is decreased when compared to an expression level of the EPAS1 in the cells in the absence of the test substance.

[20] EPAS1 as a potential drug target of a therapeutic agent for atopic dermatitis.

[21] A therapeutic agent for atopic dermatitis which contains an EPAS1 inhibitor as an active ingredient.

[22] A non-human animal for generating an atopic dermatitis model animal, having a genotype of DOCK8$^{+/-}$ TCR Tg, DOCK8$^{+/-}$, DOCK8$^{-/-}$, MST1$^{+/-}$ TCR Tg, MST1$^{+/-}$, MST1$^{-/-}$, or TCR Tg (herein, TCR Tg represents a rearranged TCR transgene).

[23] The non-human animal for generating an atopic dermatitis model animal according to [22], in which the TCR is AND.

[24] A method for generating an atopic dermatitis model non-human animal, including: crossing a non-human animal having a genotype of DOCK8$^{+/-}$ TCR Tg with a non-human animal having a genotype of DOCK8$^{+/-}$ TCR Tg, DOCK8$^{+/-}$, or DOCK8$^{-/-}$, in which a non-human animal having a genotype of DOCK8$^{-/-}$ TCR Tg appearing in offspring is the atopic dermatitis model non-human animal (herein, TCR Tg represents a rearranged TCR transgene).

[25] A method for generating an atopic dermatitis model non-human animal, including: crossing a non-human animal having a genotype of MST1$^{+/-}$ TCR Tg with a non-human animal having a genotype of MST1$^{+/-}$ TCR Tg, MST1$^{+/-}$, or MST1$^{-/-}$, in which a non-human animal having a genotype of MST1$^{-/-}$ TCR Tg appearing in offspring is the atopic dermatitis model non-human animal (herein, TCR Tg represents a rearranged TCR transgene).

[26] A method for generating an atopic dermatitis model non-human animal according to [24] or [25], in which the TCR is AND.

Advantageous Effects of Invention

According to the present invention, it is possible to clarify the mechanism regulating IL-31 production and provide an atopic dermatitis model non-human animal.

Figure 4:
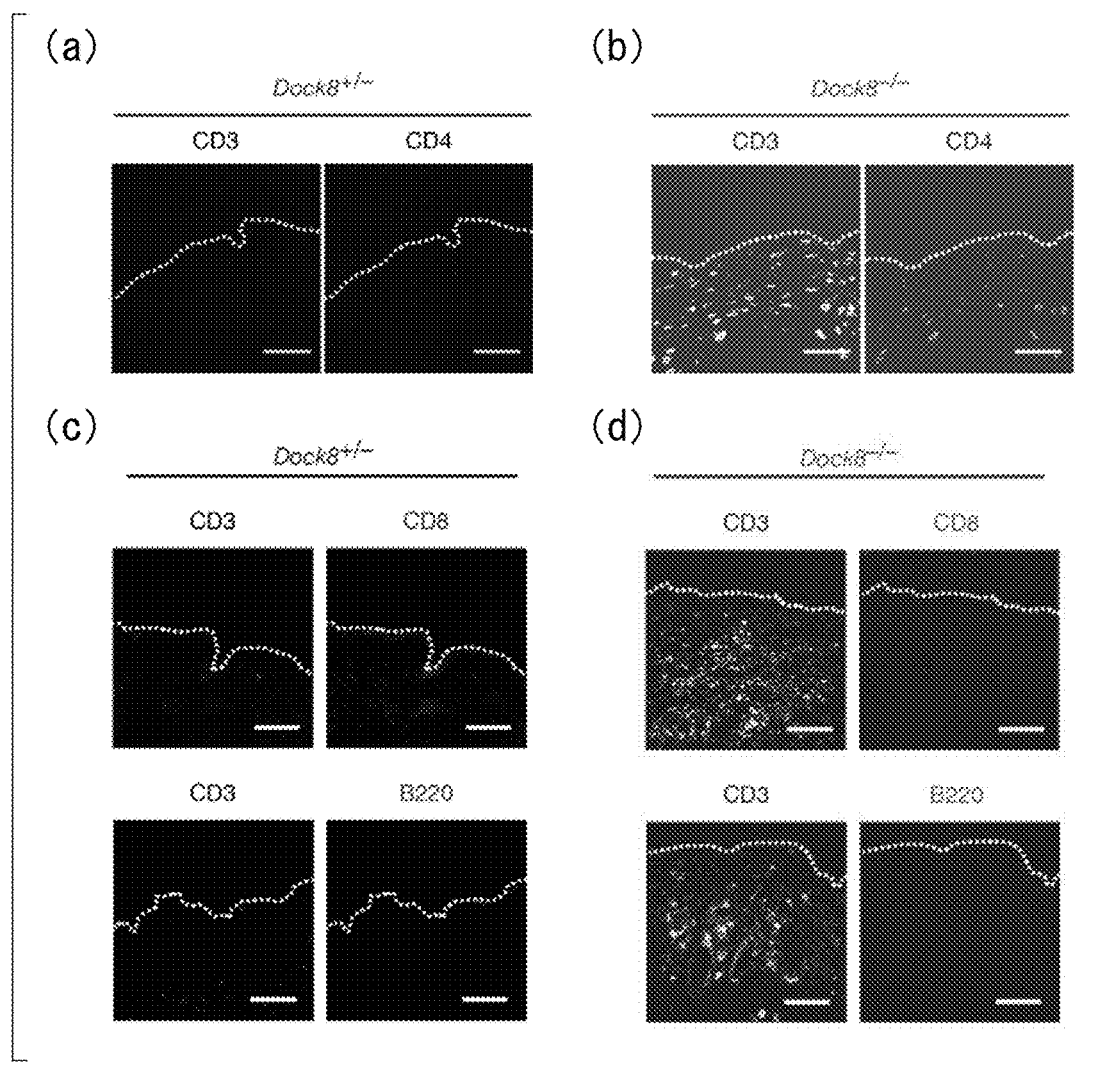

(a) and (b) of FIG. 4 are fluorescence microscopy photographs of the results in which the skin of the DOCK8$^{+/-}$ AND Tg mice (a) and the DOCK8$^{-/-}$ AND Tg mice (b) is stained with an anti-CD3 antibody and an anti-CD4 antibody as described in Experimental Example 3. (c) and (d) are fluorescence microscopy photographs of the results in which the skin of the DOCK8$^{+/-}$ AND Tg mice (c) and the DOCK8$^{-/-}$ AND Tg mice (d) is stained with the anti-CD3 antibody, an anti-CD8 antibody, and an anti-B220 antibody in Experimental Example 3.

Figure 5:
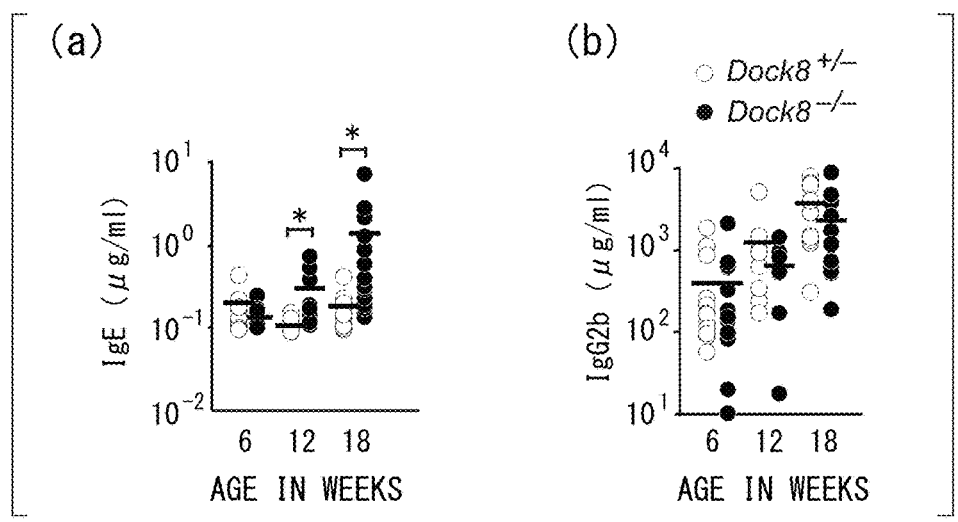

(a) and (b) of FIG. 5 are graphs of the results of measuring concentrations of IgE (a) and IgG2b (b) in sera of the DOCK8$^{+/-}$ AND Tg mice and the DOCK8$^{-/-}$ AND Tg mice in Experimental Example 4.

Figure 6:
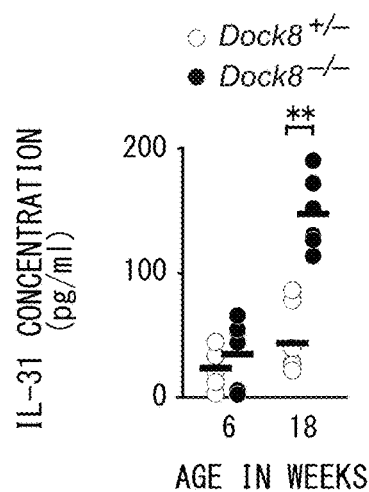

FIG. 6 is a graph of IL-31 concentration in the sera of the DOCK8$^{+/-}$ AND Tg mice and the DOCK8$^{-/-}$ AND Tg mice in Experimental Example 5.

Figure 7:
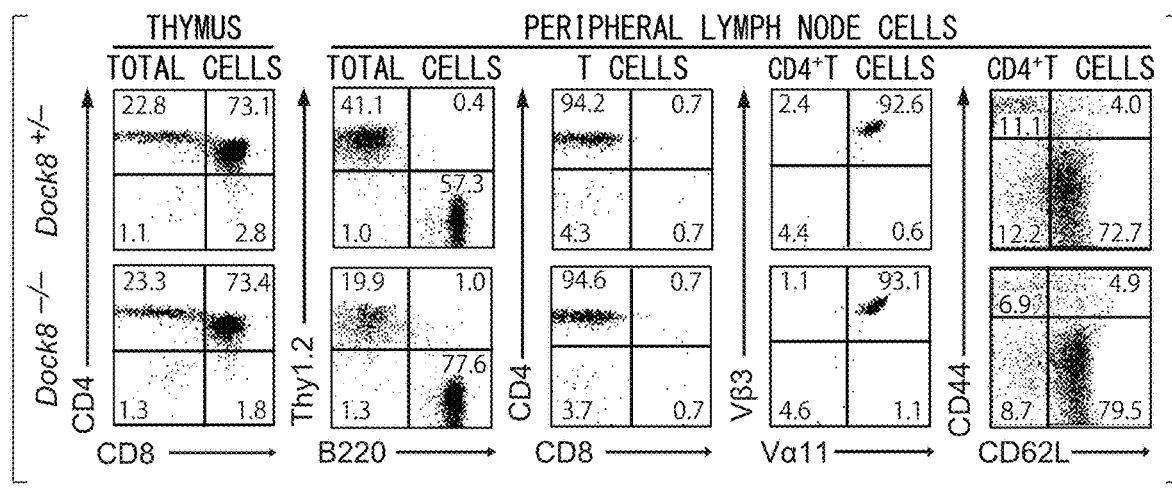

FIG. 7 is the results of flow cytometry analysis in Experimental Example 6.

Figure 8:
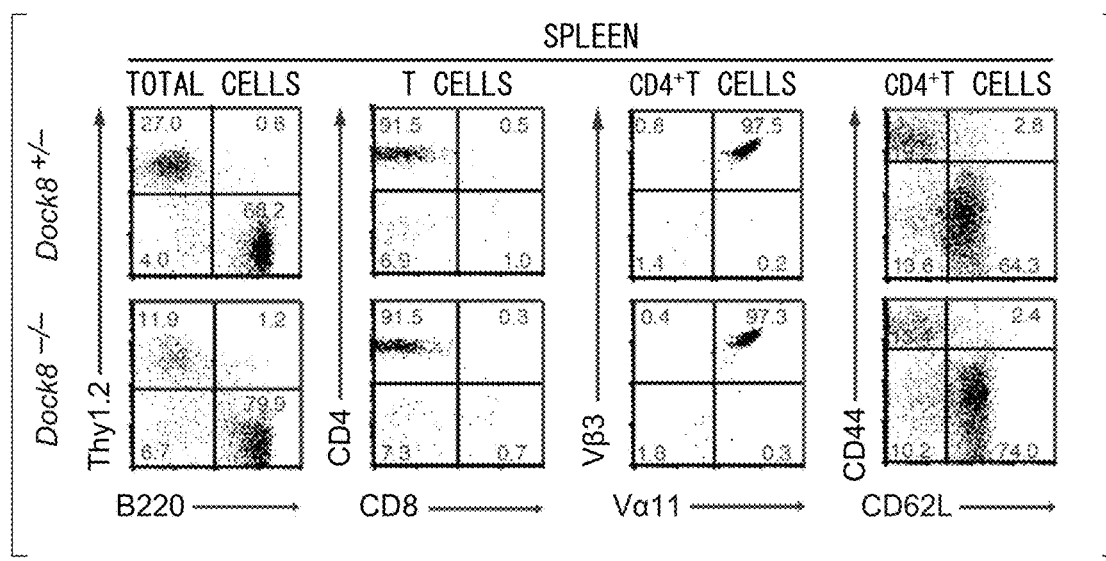

FIG. 8 is the results of flow cytometry analysis in Experimental Example 6.

Figure 9:
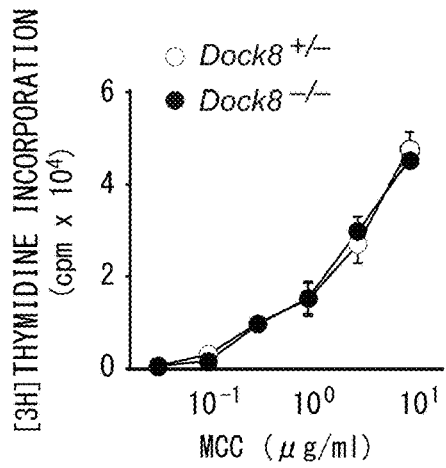

FIG. 9 is a graph of the results of examining antigen-specific proliferation of CD4$^+$ T cells in Experimental Example 7.

Figure 10:
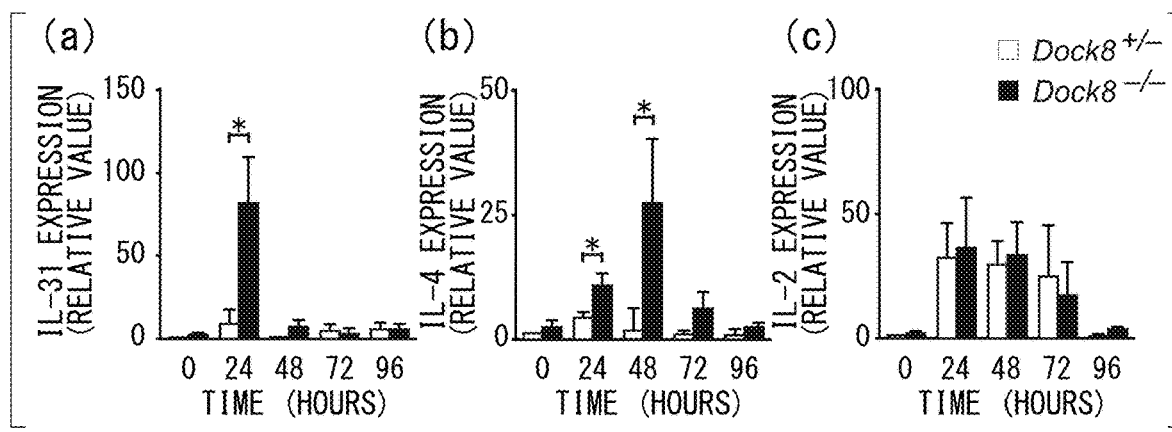

FIG. 10 shows results of Experimental Example 8. (a) is a graph showing the expression of the IL-31 gene, (b) is a graph showing the expression of the IL-4 gene, and (c) is a graph showing the expression of the IL-2 gene.

Figure 11:
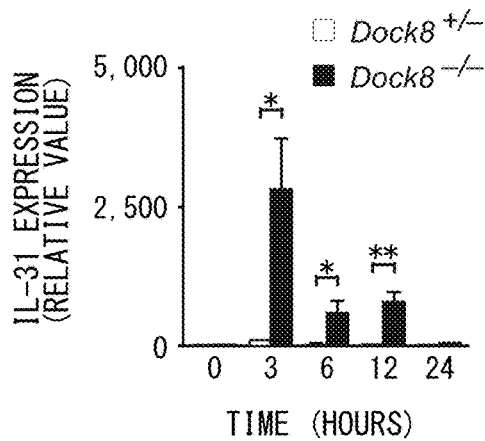

FIG. 11 is a graph showing the expression level of the IL-31 gene in secondary stimulated CD4$^+$ T cells in Experimental Example 8.

Figure 12:
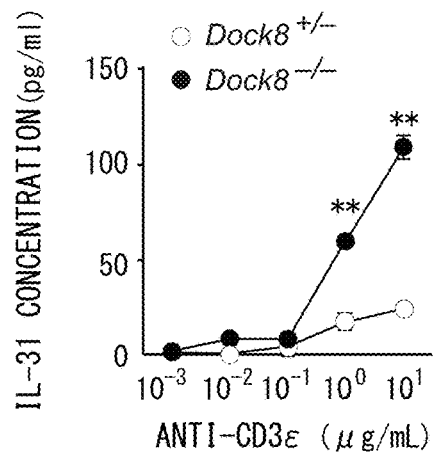

FIG. 12 is a graph of the results of IL-31 protein concentration measured by ELISA for the culture supernatant of the secondary stimulated CD4$^+$ T cells in Experimental Example 9.

Figure 13:
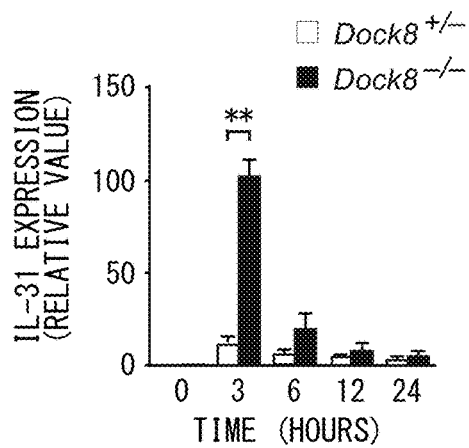

FIG. 13 is a graph showing the expression level of IL-31 gene in CD4$^+$ T cells primary stimulated in the presence of anti-IL-4 antibody in Experimental Example 10.

Figure 14:
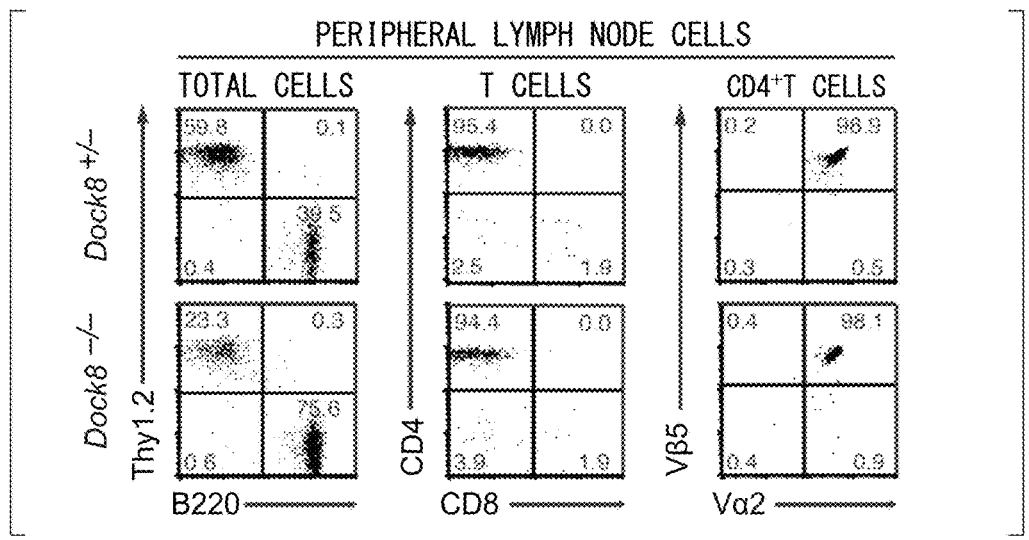

FIG. 14 shows the results of the flow cytometry analysis in Experimental Example 11.

Figure 15:
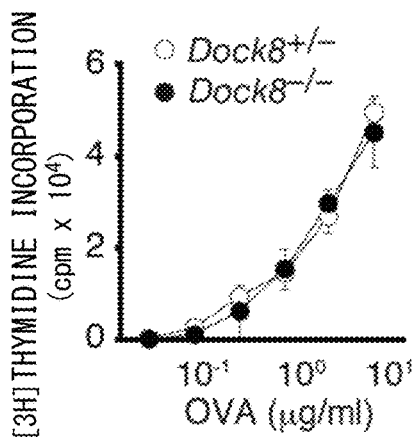

FIG. 15 is a graph showing antigen-specific proliferation of the CD4$^+$ T cells in Experimental Example 12.

Figure 16:
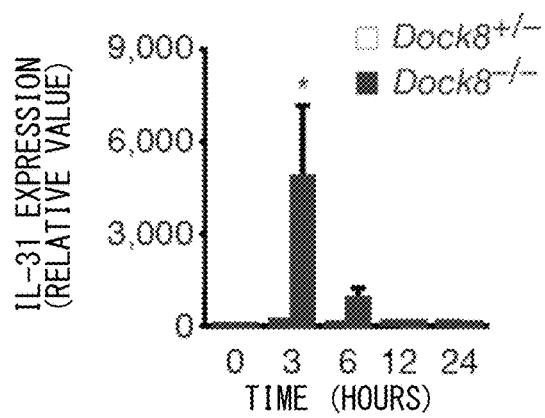

FIG. 16 is a graph showing the expression level of the IL-31 gene in the secondary stimulated CD4$^+$ T cells in Experimental Example 13.

Figure 17:
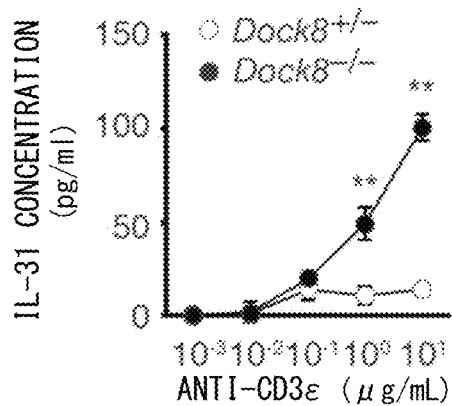

FIG. 17 is a graph of the results of IL-31 protein concentration measured by ELISA for the culture supernatant of the secondary stimulated CD4$^+$ T cells in Experimental Example 14.

Figure 18:
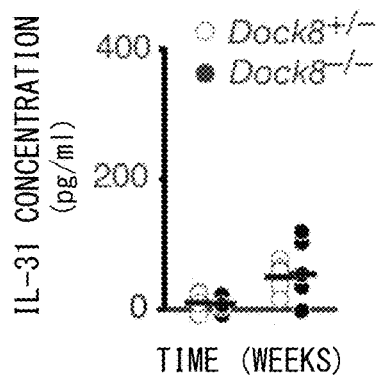

FIG. 18 is a graph showing IL-31 concentration in sera of DOCK8$^{+/-}$ OTII Tg mice and DOCK8$^{-/-}$ OTII Tg mice in Experimental Example 15.

Figure 19:
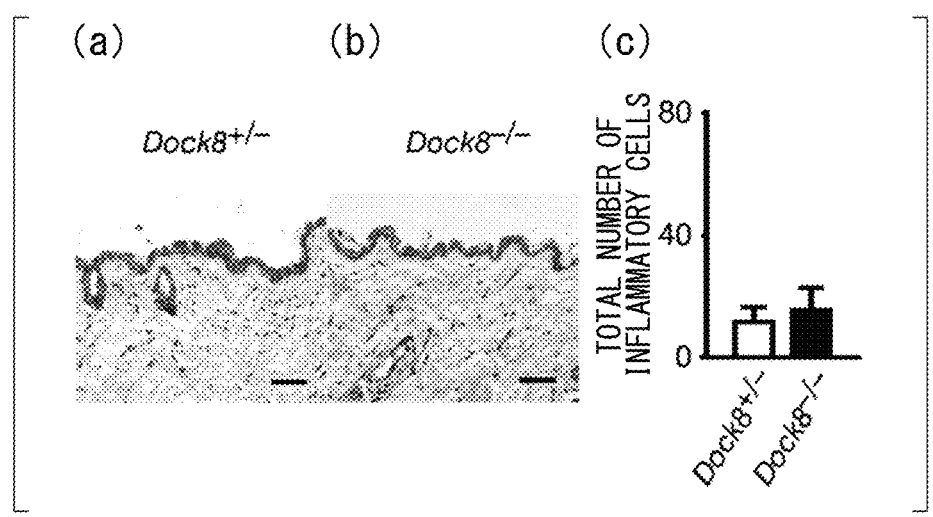

(a) and (b) of FIG. 19 are photographs of the results of hematoxylin and eosin staining of the skin of 18-week-old DOCK8$^{+/-}$ OTII Tg mice (a) and DOCK8$^{-/-}$ OTII Tg littermate mice (b) in Experimental Example 16. (c) is the results of the total number of inflammatory cells per 0.25 mm$^2$ in the skin of the DOCK8$^{+/-}$ OTII Tg mice (n=4) and the DOCK8$^{-/-}$ OTII Tg mice (n=4) in Experimental Example 16.

Figure 20:
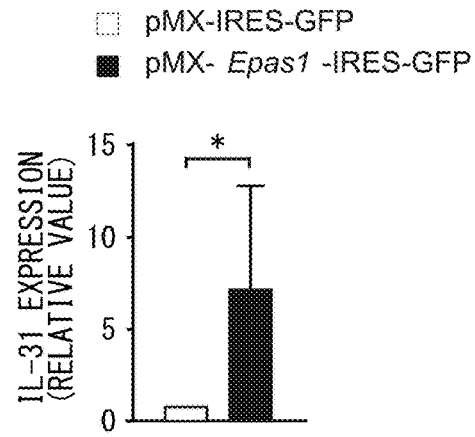

FIG. 20 is a graph showing the expression level of IL-31 gene in the CD4$^+$ T cells in Experimental Example 17.

Figure 21:
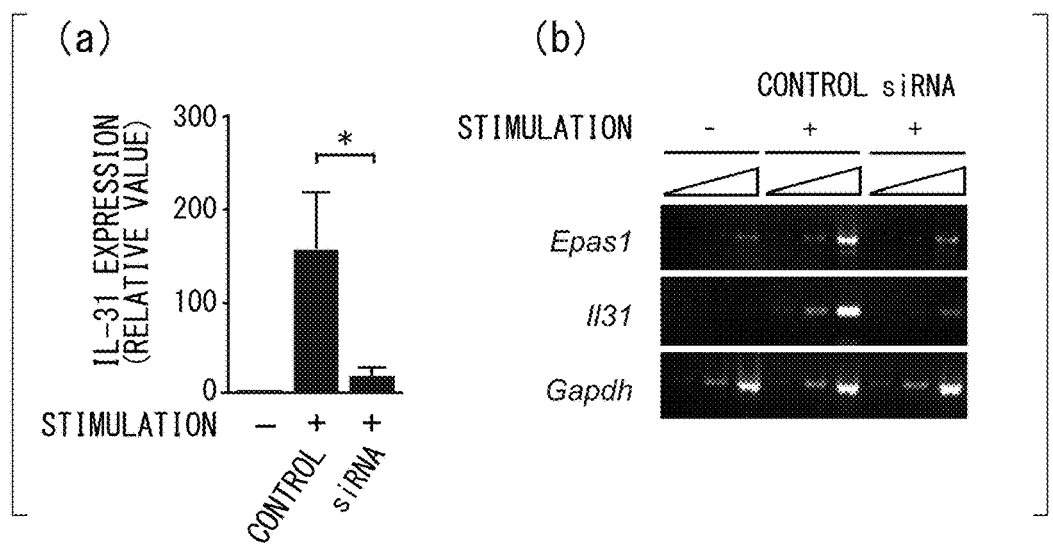

(a) of FIG. 21 is a graph showing the expression level of the IL-31 gene in Experimental Example 18. (b) is a graph of the results of RT-PCR in Experimental Example 18.

Figure 22:
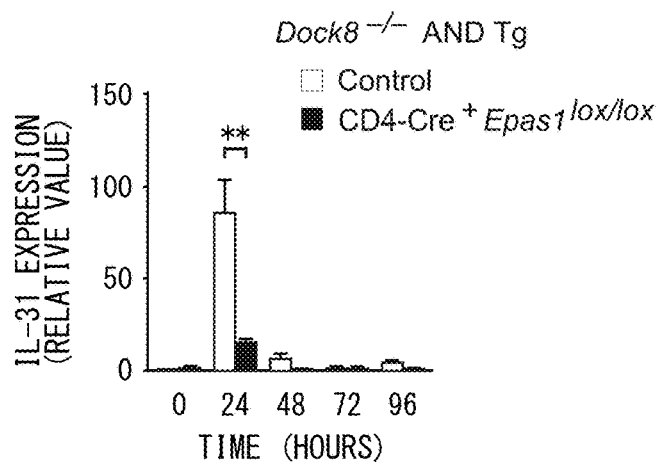

FIG. 22 is a graph showing the expression level of the IL-31 gene in Experimental Example 19.

Figure 23:
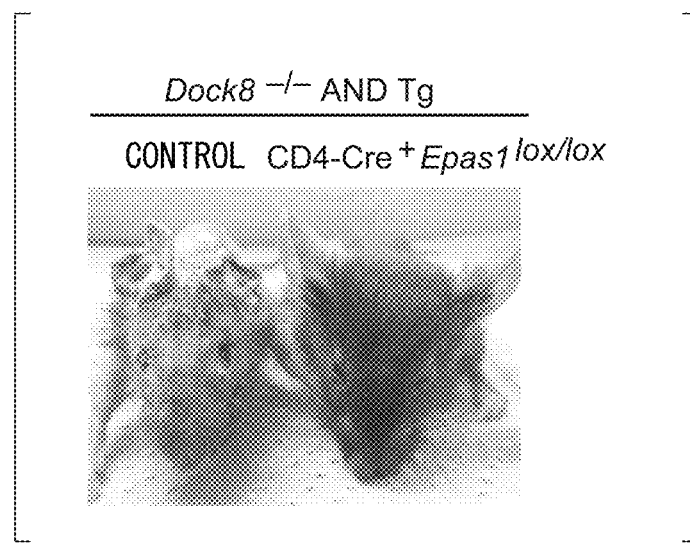

FIG. 23 is a representative photograph of CD4-Cre$^+$ EPAS1$^{lox/lox}$ DOCK8$^{-/-}$ AND Tg mice and control littermate mice in Experimental Example 20.

Figure 24:
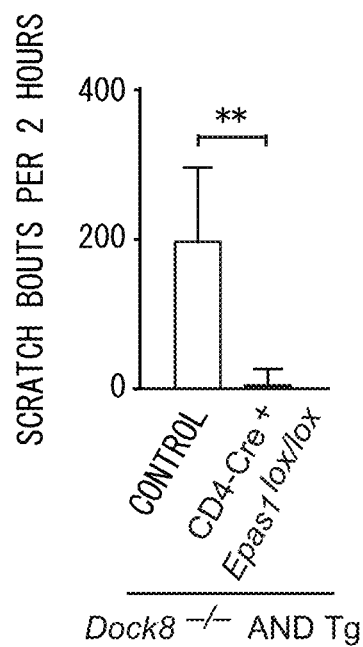

FIG. 24 is a graph showing quantitative measurements of scratching behaviors of the CD4-Cre$^+$ EPAS1$^{lox/lox}$DOCK8$^{-/-}$ AND Tg mice and the control littermate mice in Experimental Example 20.

Figure 25:
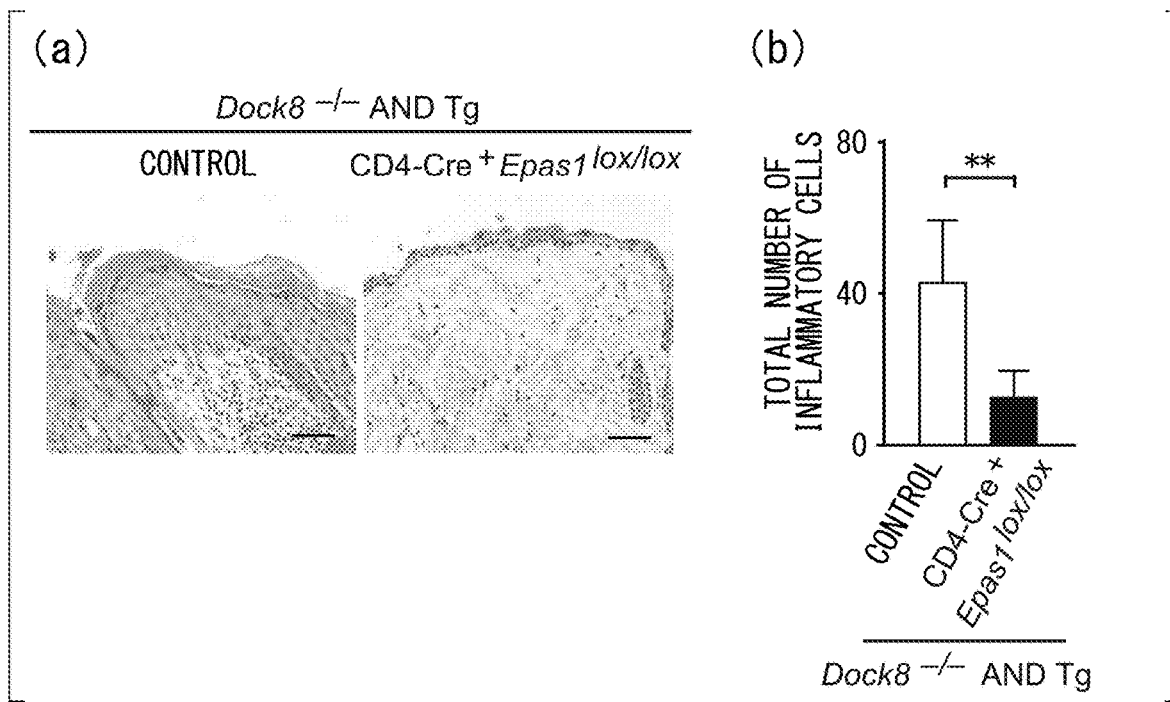

(a) of FIG. 25 shows photographs of the results of hematoxylin and eosin staining of the skin of the CD4-Cre$^+$ EPAS1$^{lox/lox}$DOCK8$^{-/-}$ AND Tg mice and the control littermate mice in Experimental Example 20. (b) is a graph of the total number of inflammatory cells per 0.25 mm$^2$ in the skin of the CD4-Cre$^+$ EPAS1$^{lox/lox}$DOCK8$^{-/-}$ AND Tg mice and the control littermate mice in Experimental Example 20.

Figure 26:
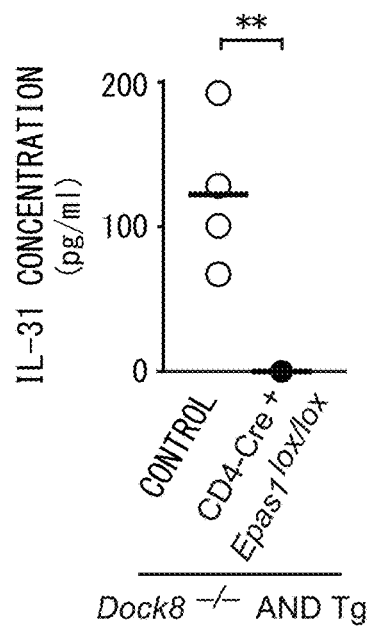

FIG. 26 is a graph showing the concentration of the IL-31 concentration in the sera of the CD4-Cre$^+$ EPAS1$^{lox/lox}$DOCK8$^{-/-}$ AND Tg mice and the control littermate mice in Experimental Example 20.

Figure 27:
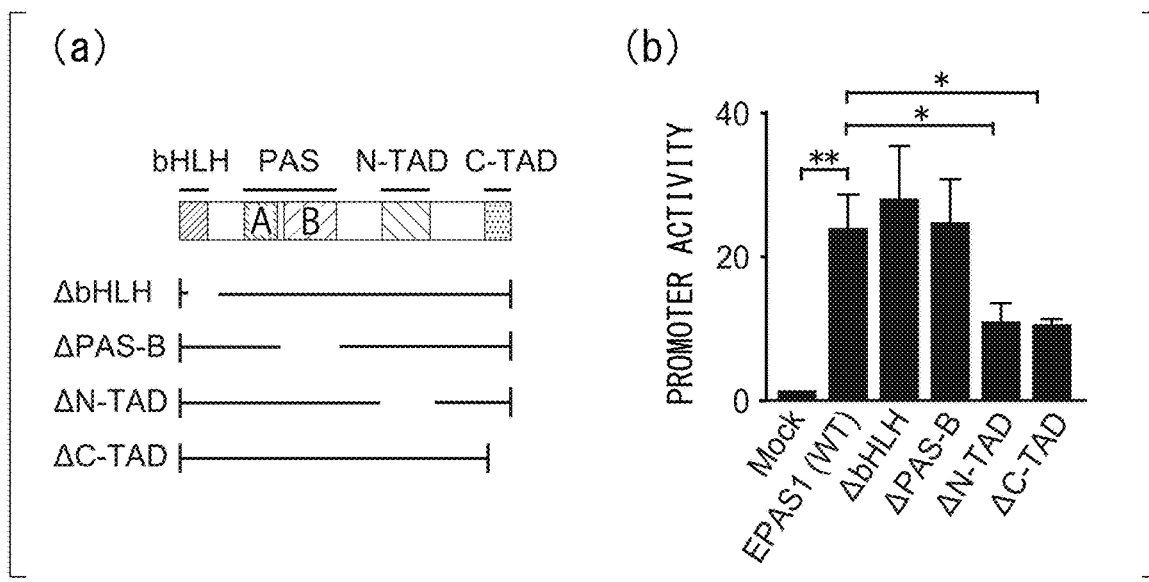

(a) of FIG. 27 is a schematic diagram of EPAS1 mutants used in Experimental Example 21. (b) is a graph showing the activity of IL-31 promoter in the presence of the EPAS1 mutants in Experimental Example 21.

Figure 28:
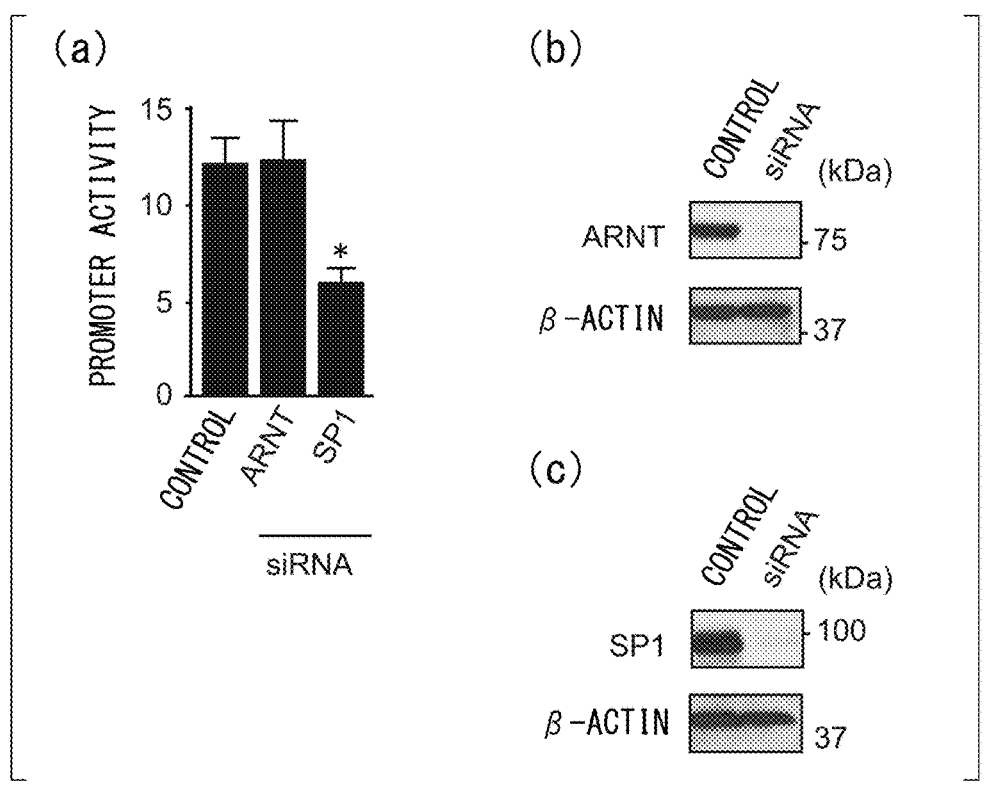

(a) of FIG. 28 is a graph showing the activity of the IL-31 promoter in Experimental Example 22. (b) are photographs of Western blotting showing the effect of knockdown of ARNT gene in Experimental Example 22. (c) are photographs of Western blotting showing the effect of knockdown of SP1 gene in Experimental Example 22.

Figure 29:
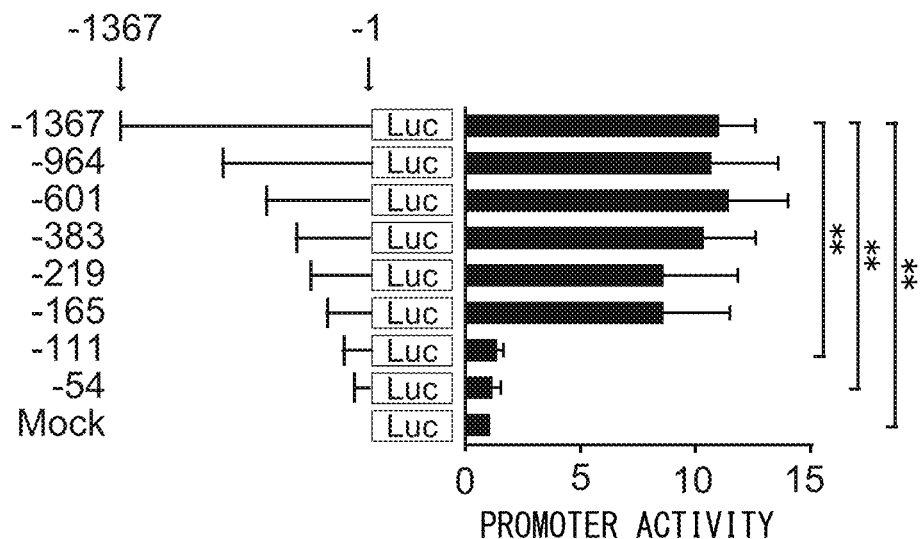

FIG. 29 is a graph showing the activity of IL-31 promoter in Experimental Example 23.

Figure 30:
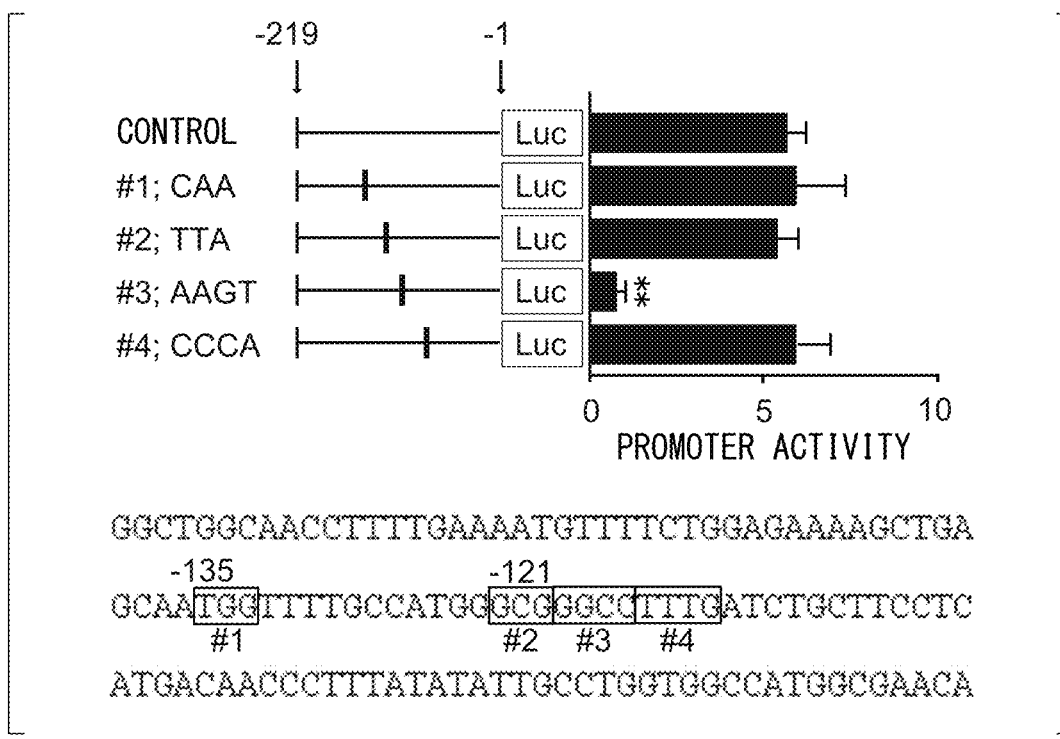

FIG. 30 is a graph showing the activity of IL-31 promoter in Experimental Example 24.

Figure 31:
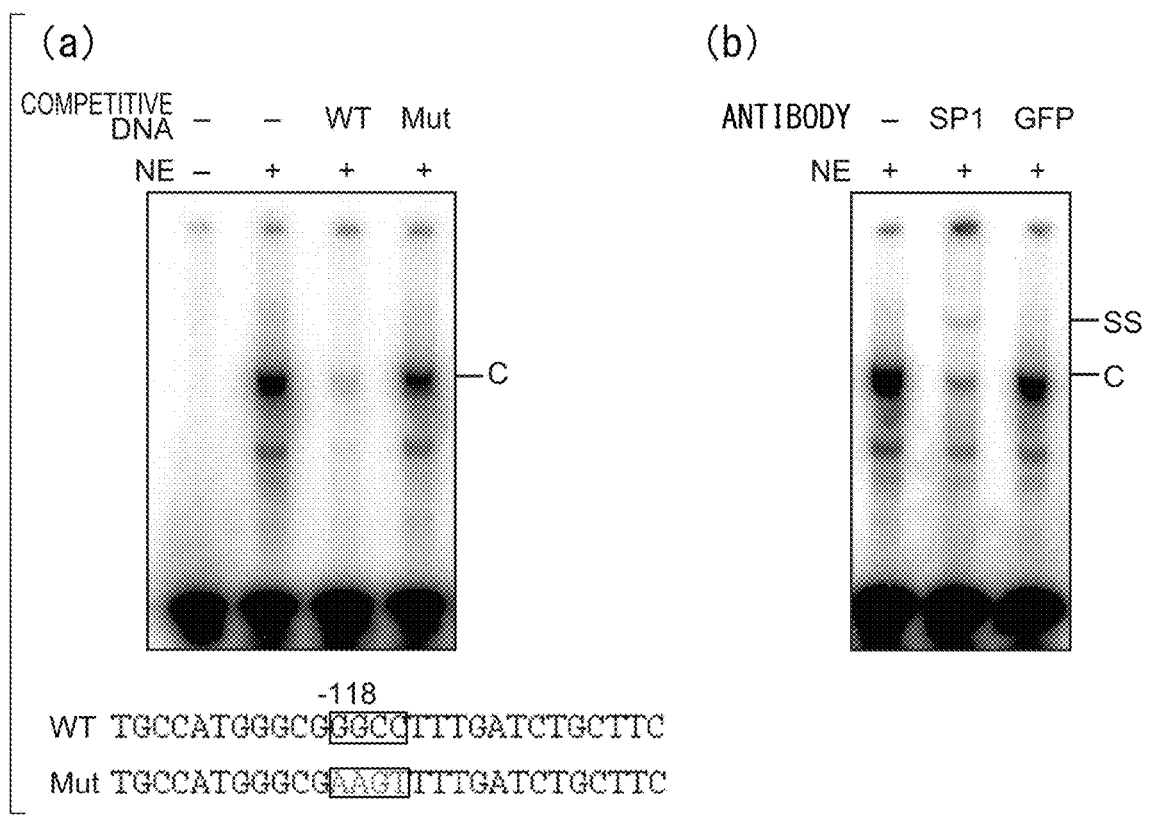

(a) and (b) of FIG. 31 are photographs showing the results of EMSA in Experimental Example 25.

Figure 32:
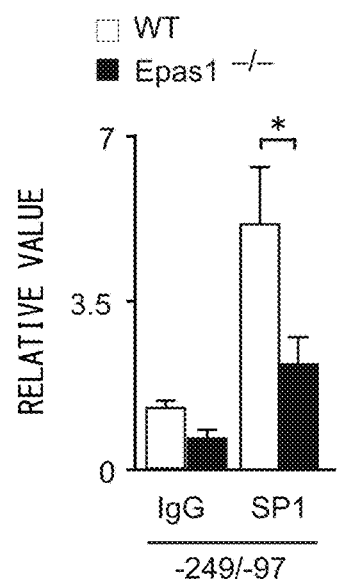

FIG. 32 is a graph of the results of ChIP assay in Experimental Example 26.

Figure 33:
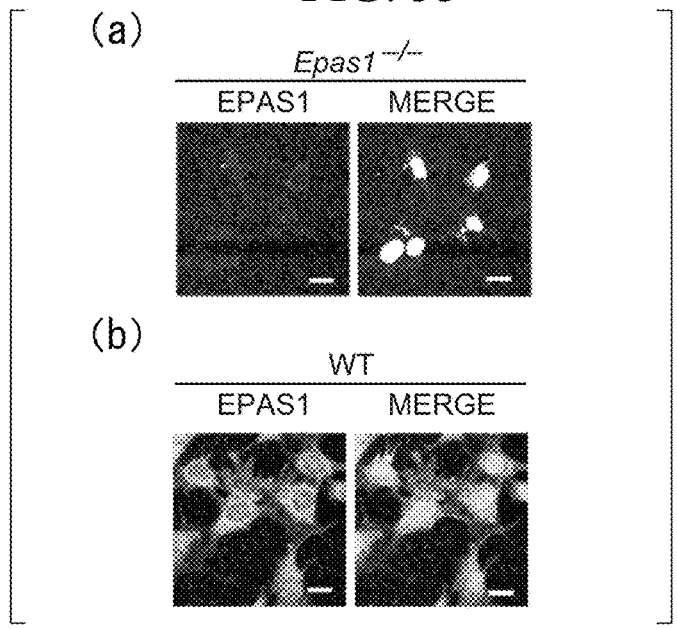

(a) of FIG. 33 shows fluorescence microscopy photographs of EPAS1$^{-/-}$ mouse embryonic fibroblasts (MEF) stained with anti-EPAS1 antibody in Experimental Example 27. (b) shows fluorescence microscopy photographs of a wild-type MEF stained with anti-EPAS1 antibody in Experimental Example 27.

Figure 34:
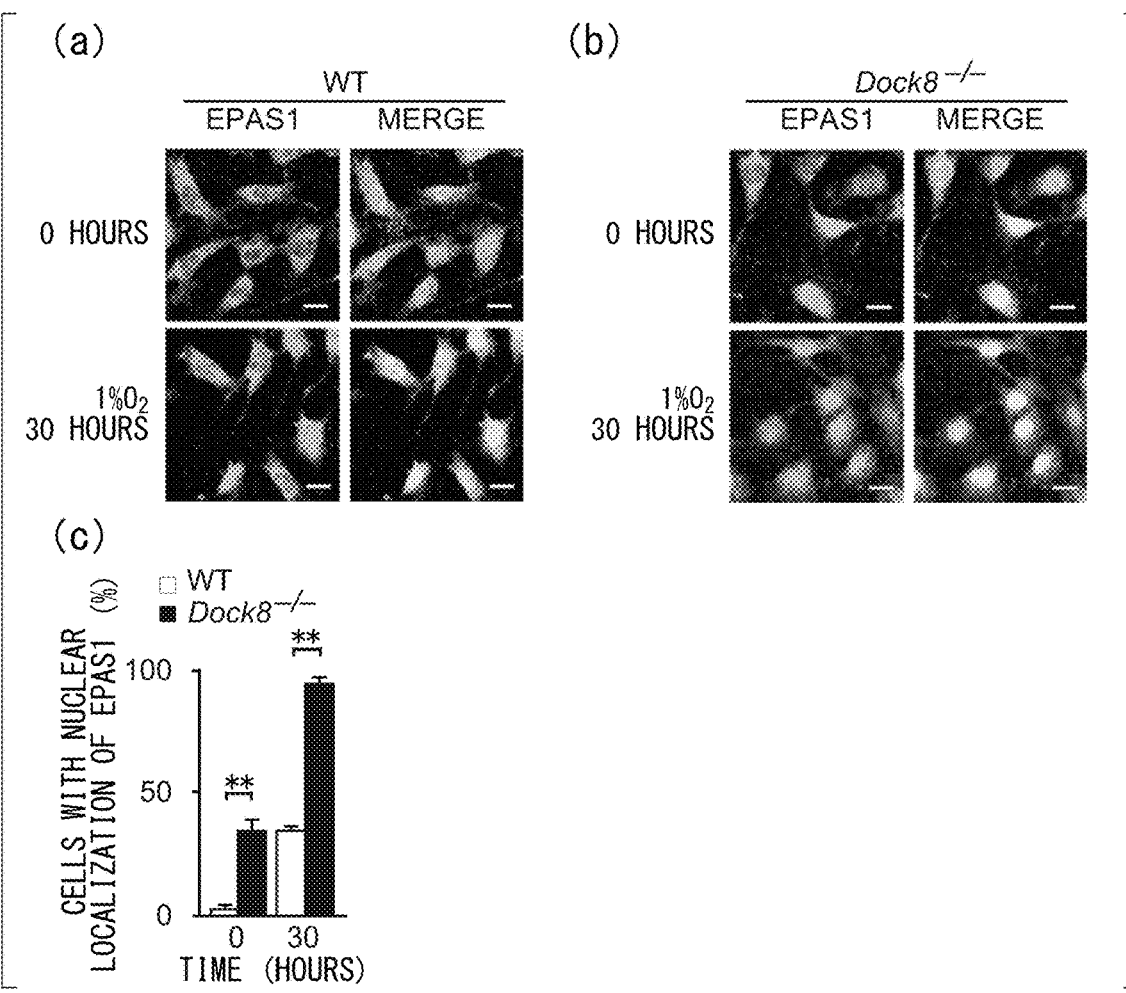

(a) and (b) of FIG. 34 are fluorescence microscopy photographs of the results of the immunofluorescence staining in Experimental Example 27. (c) is a graph showing the proportion of cells with nuclear localization of EPAS1 in Experimental Example 27.

Figure 35:
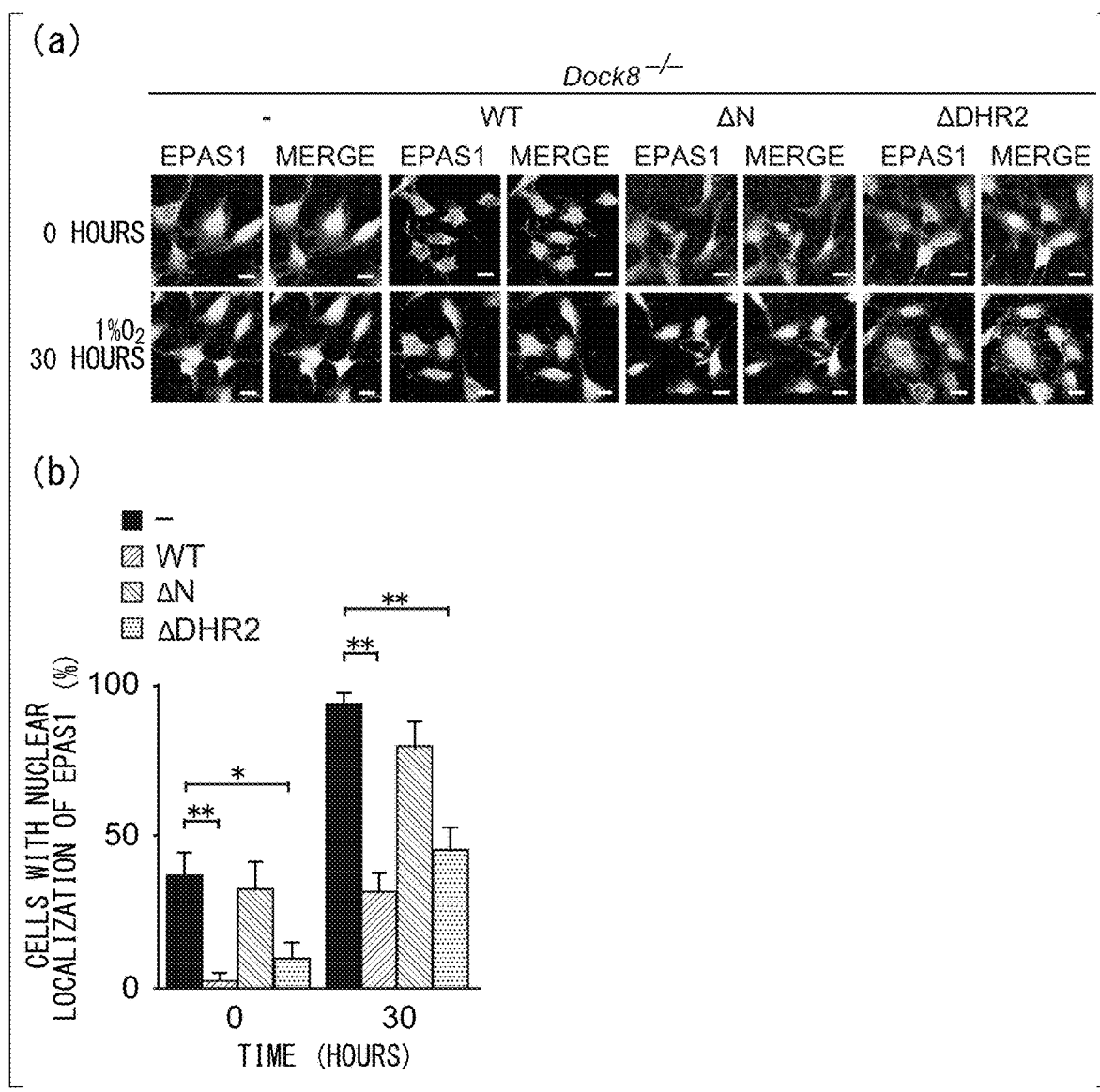

(a) of FIG. 35 is a fluorescence microscopy photograph of the results of the immunofluorescence staining in Experimental Example 28. (b) is a graph showing the proportion of the cells with nuclear localization of the EPAS1 in Experimental Example 28.

Figure 36:
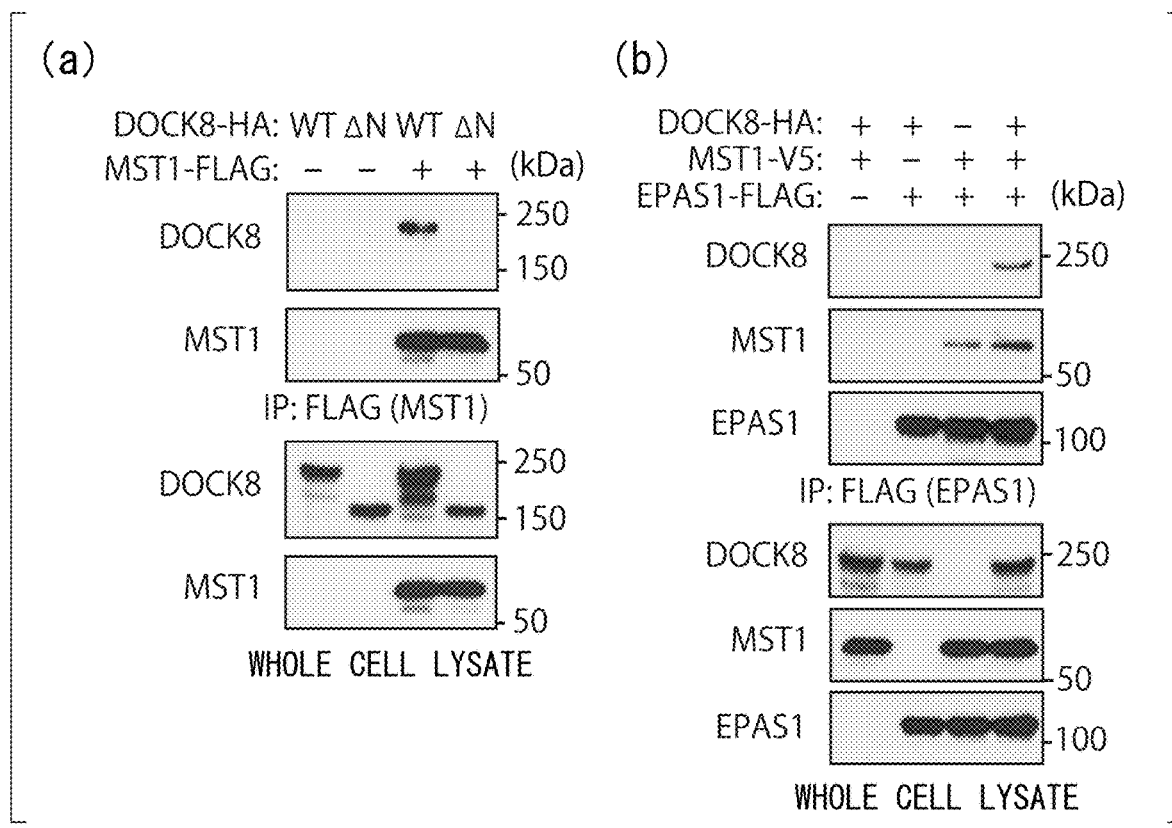

(a) and (b) of FIG. 36 are photographs of the results of immunoprecipitation in Experimental Example 29.

Figure 37:
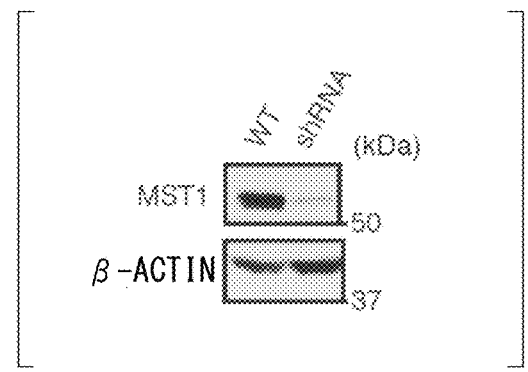

FIG. 37 shows photographs of Western blotting showing the effect of knockdown of MST1 gene in Experimental Example 30.

Figure 38:
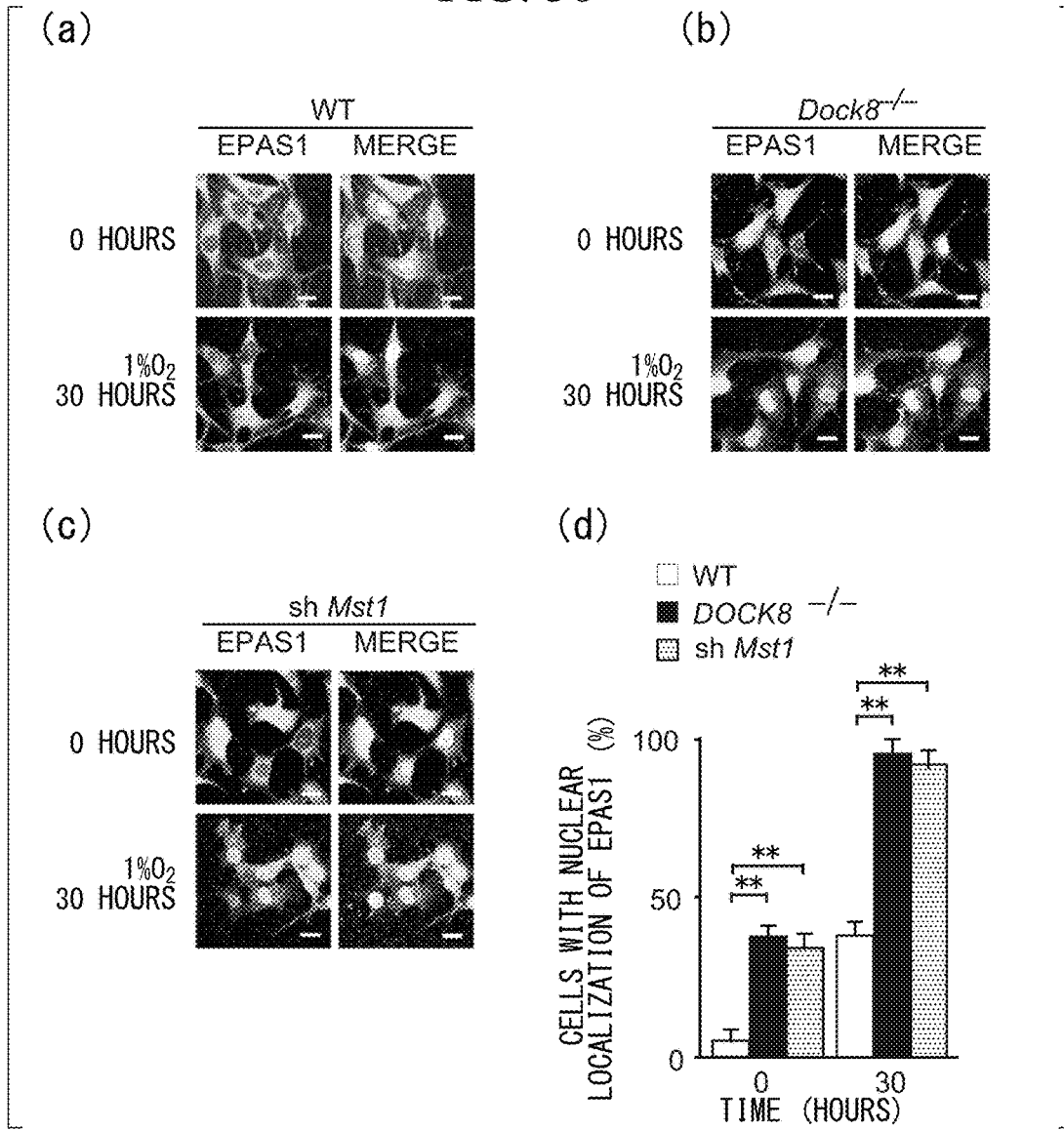

(a) to (c) of FIG. 38 are fluorescence microscopy photographs of the results of the immunofluorescence staining in Experimental Example 30. (d) is a graph showing the proportion of the cells with nuclear localization of EPAS1 in Experimental Example 30.

Figure 39:
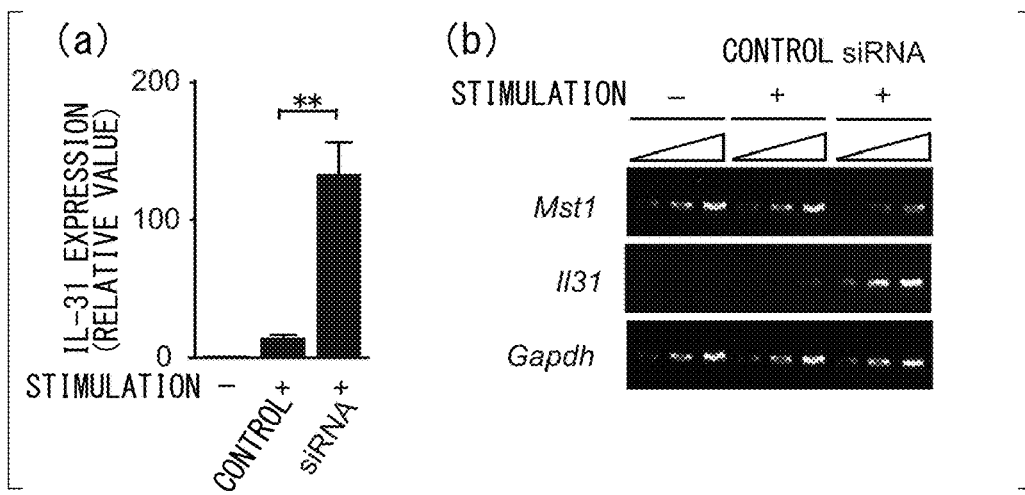

(a) of FIG. 39 is a graph showing the expression level of the IL-31 gene in Experimental Example 31. (b) is a graph of the results of the RT-PCR in Experimental Example 31.

Figure 40:
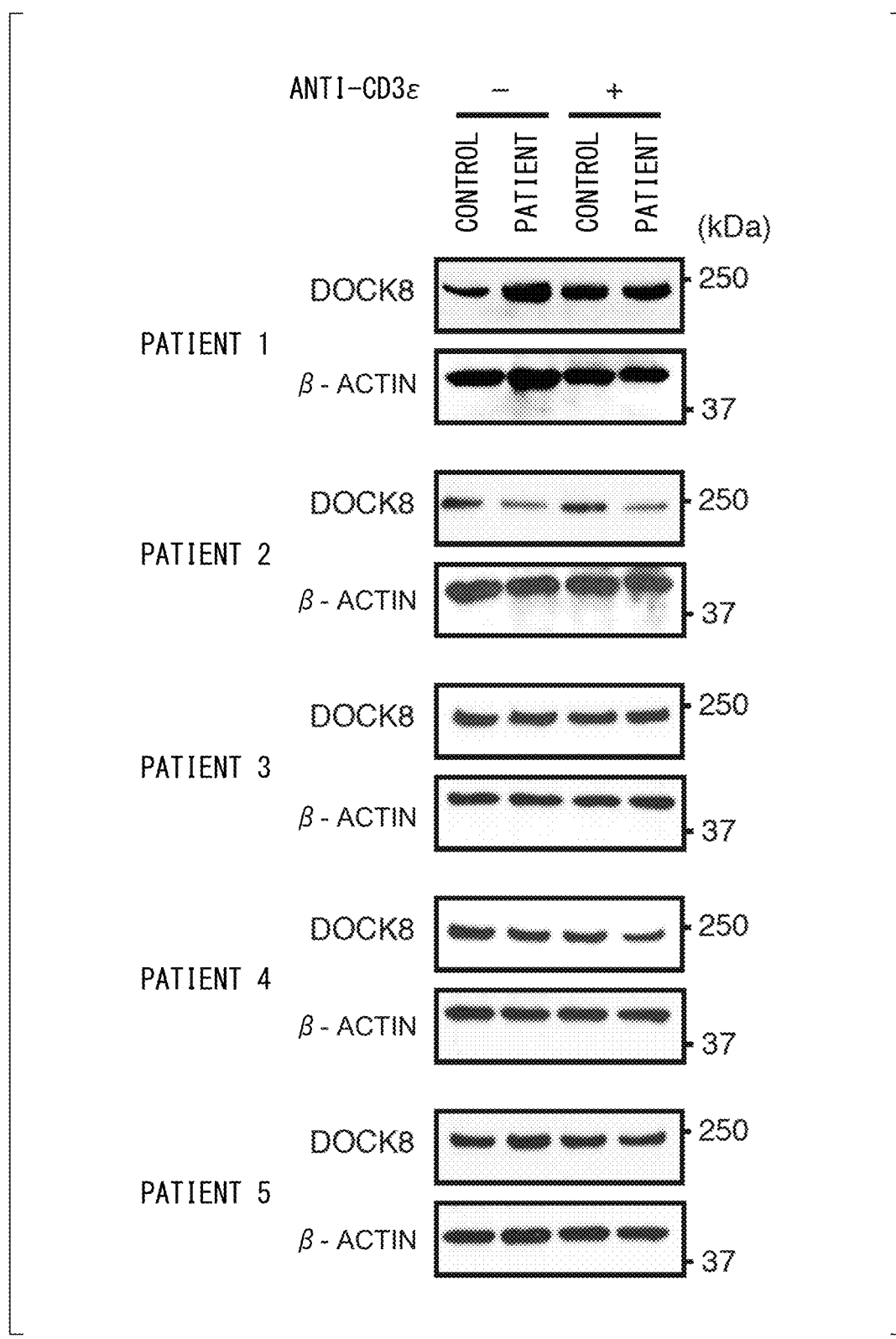

FIG. 40 shows photographs of the results of the Western blotting in Experimental Example 32.

Figure 41:
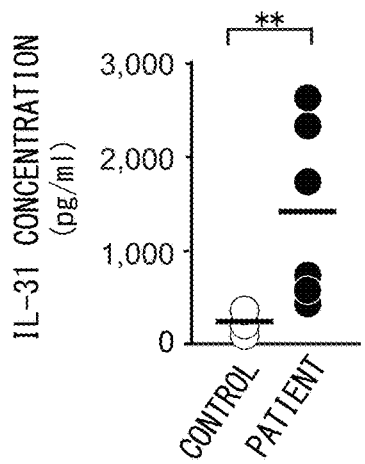

FIG. 41 is a graph showing the concentration of the IL-31 in serum of an atopic dermatitis patient and a healthy subject (control) in Experimental Example 33.

Figure 42:
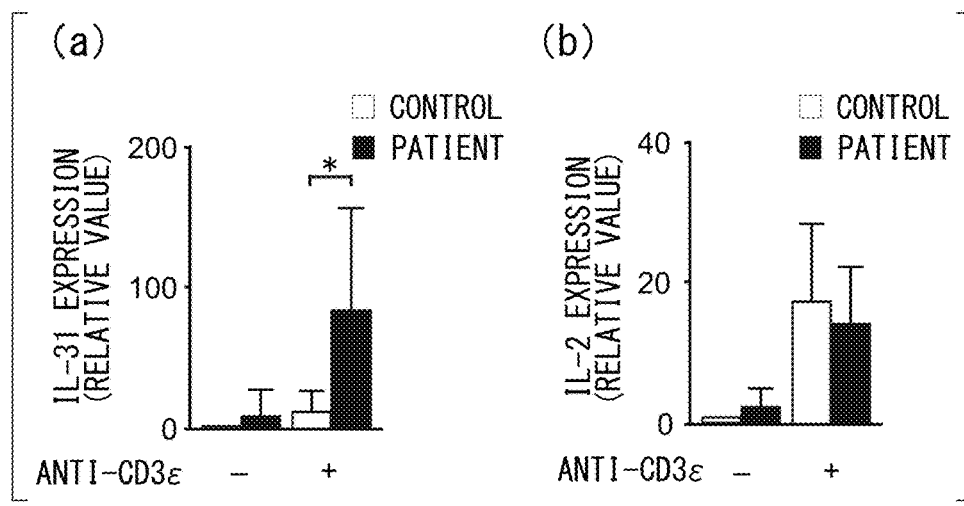

(a) of FIG. 42 is a graph showing the expression level of the IL-31 gene in Experimental Example 34. (b) is a graph showing the expression level of IL-2 gene in Experimental Example 34.

Figure 43:
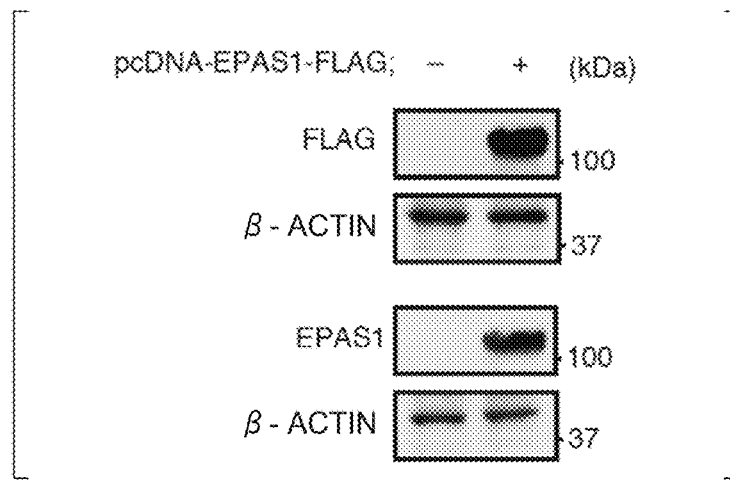

FIG. 43 shows photographs showing the validity of the anti-EPAS1 antibody by the Western blotting in Experimental Example 35.

Figure 44:
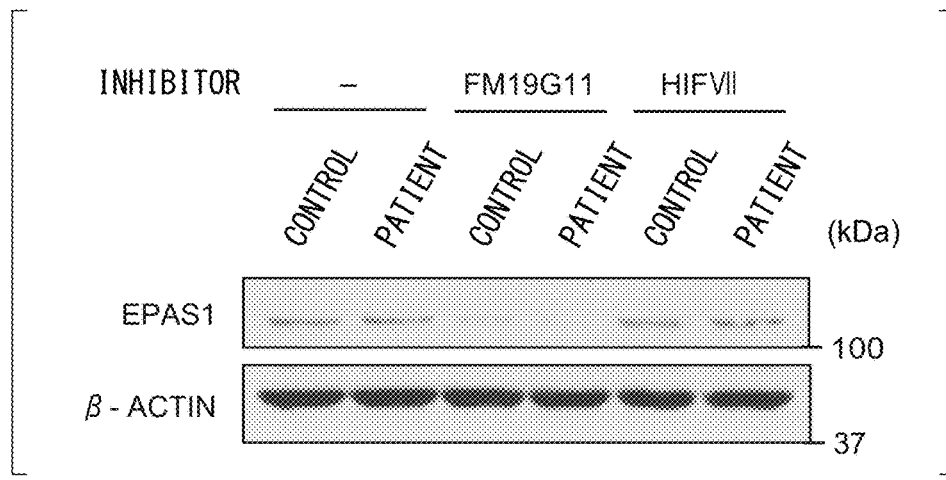

FIG. 44 shows photographs showing the effect of EPAS1 inhibitors on EPAS1 expression by the Western blotting in Experimental Example 35.

Figure 45:
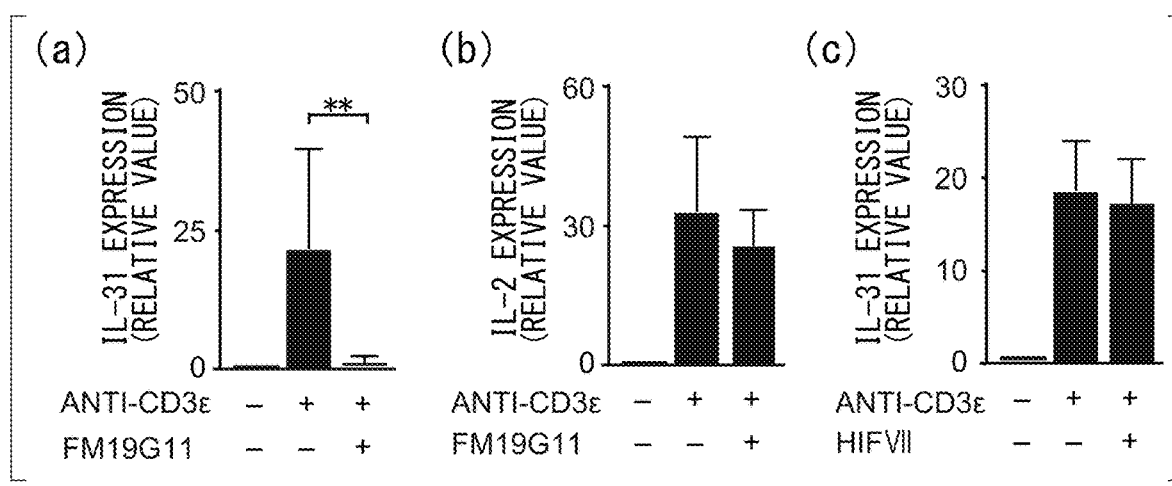

(a) of FIG. 45 is a graph showing the effect of FM19G11 on the expression level of IL-31 gene in Experimental Example 36. (b) is a graph showing the effect of FM19G11 on the expression level of IL-2 gene in Experimental Example 36. (c) is a graph showing the effect of HIFVII on the expression level of the IL-31 gene in Experimental Example 36.

Figure 46:
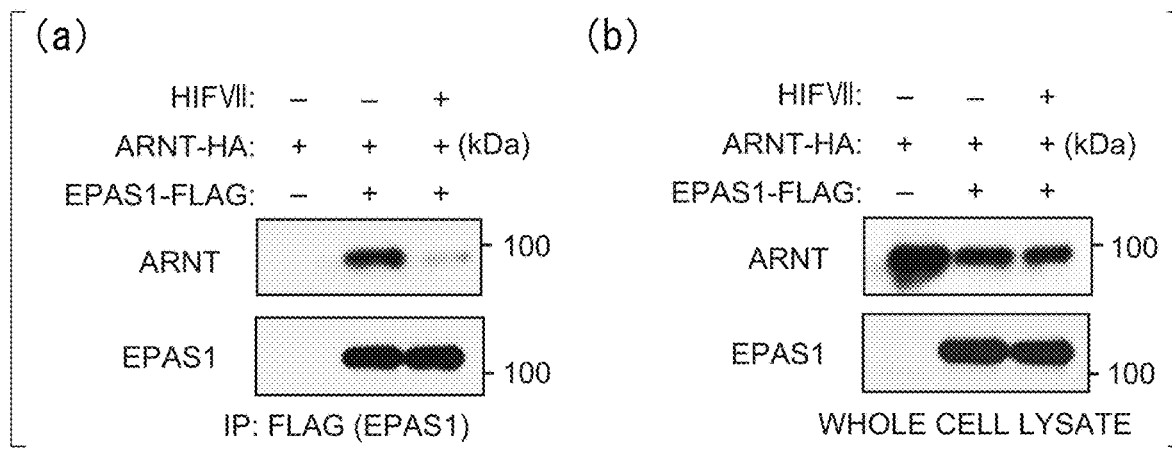

(a) and (b) of FIG. 46 are photographs of the results of the immunoprecipitation in Experimental Example 37.

Figure 47:
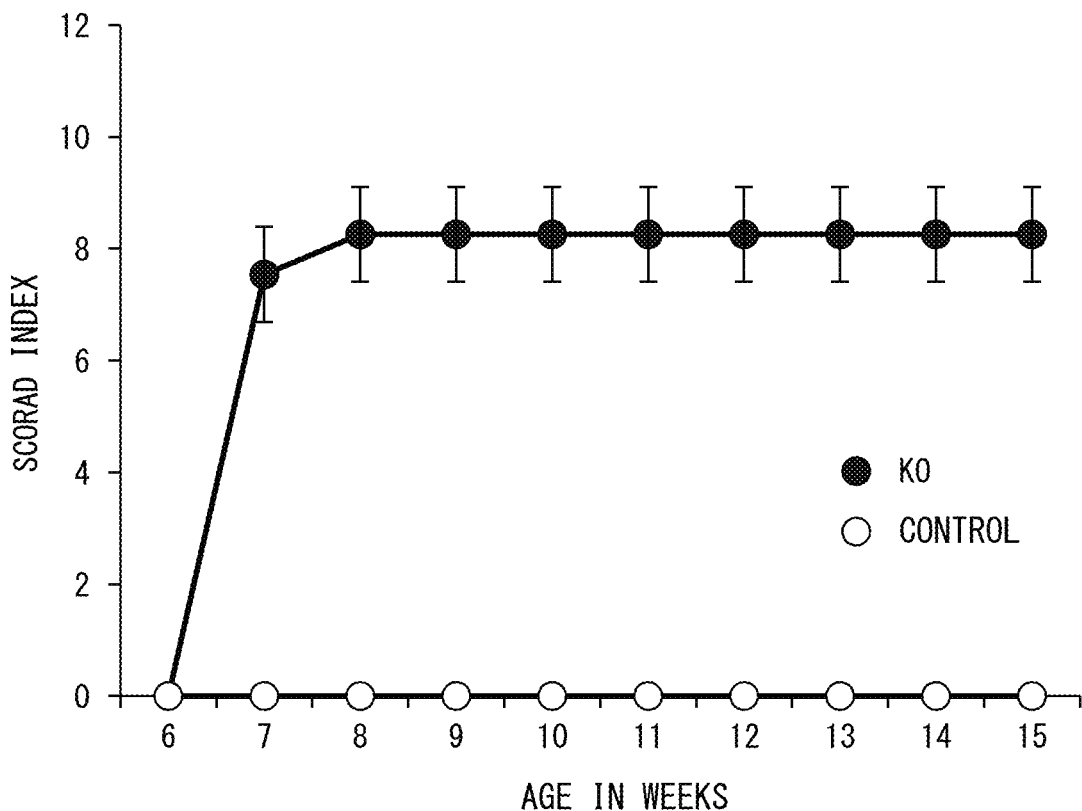

FIG. 47 is a graph of the results of quantitative assessment of dermatitis of DOCK8-conditional knockout mice and control mice in Experimental Example 38.

Figure 48:
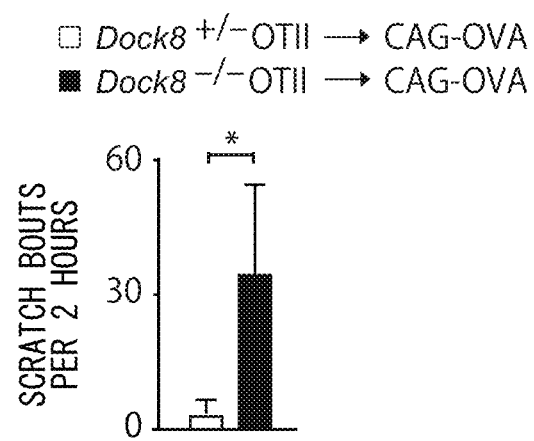

FIG. 48 is a graph showing quantitative measurements of scratching behaviors of CAG-OVA mice following adoptive transfer of either CD4$^+$ T cells from DOCK8$^{+/-}$ OTII Tg mice or DOCK8$^{-/-}$ OTII Tg mice in Experimental Example 39.

DESCRIPTION OF EMBODIMENTS

[Atopic Dermatitis Model Non-Human Animal]

In one embodiment, the present invention provides an atopic dermatitis model non-human animal which has a gene mutation so as not to form a complex comprising DOCK8 protein, MST1 protein, and EPAS1 protein in CD4$^+$ T cells.

The non-human animal is not particularly limited, and examples thereof include a mouse, a rat, a rabbit, a pig, a cow, a monkey, and the like. The atopic dermatitis model non-human animal of the present embodiment has a gene mutation through which a complex comprising DOCK8 protein, MST1 protein, and EPAS1 protein is not formed in the CD4$^+$ T cells.

In the present specification, the atopic dermatitis model non-human animal means a non-human animal which is a model for atopic dermatitis. The model for atopic dermatitis means an experimental system capable of reproducing at least a part of onset mechanisms of the atopic dermatitis or symptoms of atopic dermatitis. For example, CD4$^+$ T cells derived from the atopic dermatitis model non-human animal of the present embodiment produce large amounts of IL-31 on TCR stimulation, and therefore it can be used as a model for atopic dermatitis. In addition, after CD4$^+$ T cells derived from the atopic dermatitis model non-human animal of the present embodiment are stimulated and transferred to another non-human animal (recipient), the atopic dermatitis develops in the recipient, and thus such recipient of the non-human animal can be used as a model for atopic dermatitis. In the related art, the mechanism of how CD4$^+$ T cells produce large amounts of the IL-31 on the TCR stimulation has not been known. Therefore, the atopic dermatitis model non-human animal of the present embodiment can be effectively used for development of a therapeutic agent and a therapeutic method for atopic dermatitis.

In the atopic dermatitis model non-human animal of the present embodiment, a rearranged T cell receptor (TCR) may be expressed. The rearranged TCR is not particularly limited as long as it is TCR that recognizes a specific antigen, and examples thereof include AND, OTII, and the like. The AND and the OTII will be described later. The above-described TCR may have self-reactivity. For example, as will be described in examples later, the AND is considered to be a TCR having self-reactivity.

In one embodiment, the present invention provides an atopic dermatitis model non-human animal which has the gene mutation in which the complex comprising DOCK8 protein, MST1 protein, and EPAS1 protein is not formed in the CD4$^+$ T cells, and in which the TCR having self-reactivity is expressed. As will be described in the examples later, the atopic dermatitis spontaneously develops in the atopic dermatitis model non-human animal of the present embodiment.

In NC/Nga mice, which have been used as an atopic dermatitis model mice in the related art, the atopic dermatitis is caused due to parasitic mites. However, in the NC/Nga mice, the atopic dermatitis does not develop under specific-pathogen-free (SPF) environments. In addition, there is a case where the NC/Nga mice do not show scratching behavior even when the dermatitis occurs, and there is a case where an individual excessively exhibiting dermatitis does not show an itching reaction. As above, the NC/Nga mice have different symptoms from human atopic dermatitis patients.

With respect to the above description, the atopic dermatitis spontaneously develops in the atopic dermatitis model non-human animal of the present embodiment even under SPF environments. In addition, the atopic dermatitis model non-human animal of the present embodiment is stable in symptoms of the dermatitis and the itching reaction, and shows symptoms extremely similar to those of human atopic dermatitis patients, in that the itching reaction becomes strong, and the concentration of IL-31 in serum increases, in accordance with progression of the symptoms of the dermatitis.

Therefore, the atopic dermatitis model non-human animal of the present embodiment is extremely useful for clarifying the pathogenesis of human atopic dermatitis, developing a therapeutic drug and a therapeutic method, and the like.

As will be described in the examples later, the present inventors have clarified the mechanism of regulating IL-31 expression that is a pruritogen of atopic dermatitis. That is, in CD4$^+$ T cells of a wild type, the complex containing the DOCK8 protein, the MST1 protein, and EPAS1 protein is formed, and therefore the EPAS1 protein is localized within the cytoplasm. With respect to the above description, if the above complex cannot be formed, the EPAS1 protein is translocated into the nucleus and induces IL-31 expression in association with SP1 protein. Association between EPAS1 and the SP1 is important for induction of transcription of the IL-31.

In addition, it is known that the EPAS1 forms a complex with an aryl hydrocarbon receptor nuclear translocator (also called ARNT, HIF-1β), and activates transcription of a target gene in response to environmental stress such as hypoxia, for example. In addition, it has been reported that the ARNT is involved in neurogenesis and control of lumen formation of trachea/salivary gland, and it is known that the ARNT is an important factor in development. Accordingly, there is a concern that drugs affecting the functions of ARNT may have severe side effects.

However, as will be described in the examples later, the present inventors have revealed that the EPAS1 functions independently of the ARNT and induces IL-31 production. That is, it has been revealed that the EPAS1 activates the IL-31 promoter independently of the ARNT, but in collaboration with the SP.

The above description means that, in a case where the EPAS1 is a therapeutic target, there is less concern that causes severe side effects. That is, the EPAS1 is suitable as a therapeutic target for atopic dermatitis.

Therefore, in the one embodiment, the present invention provides the EPAS1 as a potential drug target of the therapeutic target for atopic dermatitis.

Note that RefSeq ID of human DOCK8 protein is NP_982272, and RefSeq ID of mouse DOCK8 protein is NP_083061. In addition, RefSeq ID of human MST1 protein is NP_006273, and RefSeq ID of mouse MST1 protein is NP_067395. In addition, RefSeq ID of human EPAS1 protein is NP_001421, and RefSeq ID of mouse EPAS1 protein is NP_034267.

In the atopic dermatitis model non-human animal of the present embodiment, the gene mutation in which the tri-molecular complex comprising the DOCK8 protein, the MST1 protein, and the EPAS1 protein is unformable is not particularly limited as long as it is a mutation by which the EPAS1 protein is localized in the nucleus, and examples of the mutation may be knockout of DOCK8 gene or MST1 gene, may be a knockdown of the DOCK8 gene or the MST1 gene, or may be a gene mutation in which an N terminal side of the DOCK8 protein is deleted.

As will be described in the examples later, the present inventors have revealed that EPAS1 is localized in the nucleus of the cells when DOCK8 is knocked out, 527 amino acids of the N terminal side of the DOCK8 protein are deleted, and the knockdown of the MST1 gene, and the like, and therefore the IL-31 gene expression increases following TCR stimulation.

The DOCK8 gene or the MST1 gene may be knocked out in all organs or may be knocked out only with a cell population containing the CD4$^+$ T cells by conditional knockout or the like.

In the atopic dermatitis model non-human animal of the present embodiment, in addition to the gene mutation as described above, CD4$^+$ T cells may express a (rearranged) TCR transgene (TCR Tg) which reorganizes a specific antigen. That is, the atopic dermatitis model non-human animal of the present embodiment may have a genotype of DOCK8$^{-/-}$ TCR Tg or MST1$^{-/-}$ TCR Tg. Herein, TCR Tg represents a rearranged TCR transgene.

As will be described in the examples later, the present inventors have revealed that in CD4$^+$ T cells where nuclear transportation of the EPAS1 is likely to occur, large amounts of IL-31 are induced following TCR stimulation. As a result, the concentration of the IL-31 in serum increases, and therefore atopic dermatitis develops.

Examples of the rearranged TCR include the AND. It is known that the AND is the TCR that recognizes a peptide (SEQ ID NO: 1) consisting of 88th to 103rd amino acids of Moth cytochrome c (MCC), which forms a complex with MHC class II I-E$^\kappa$ molecule, but the AND recognizes I-A$^b$ molecules in the thymus to differentiate and mature (refer to, for example, Kaye J. et al., Selective development of CD4+ T cells in transgenic mice expressing a class II MHC-restricted antigen receptor, Nature 341, 746-749, 1989.).

The atopic dermatitis model non-human animal of the present embodiment may have a genotype of DOCK8$^{-/-}$ AND Tg or MST1$^{-/-}$ AND Tg.

In the non-human animal having the genotype of DOCK8$^{-/-}$ AND Tg, DOCK8 gene is deleted, and therefore the CD4$^+$ T cells cannot form the complex containing the DOCK8 protein, the MST1 protein, and EPAS1 protein. In addition, these CD4$^+$ T cells produce large amounts of the IL-31, and thus the atopic dermatitis spontaneously develops in this non-human animal.

Furthermore, in the non-human animal having the genotype of MST1$^{-/-}$ AND Tg, the MST1 gene is deleted, and therefore the CD4$^+$ T cells cannot form the complex containing the DOCK8 protein, the MST1 protein, and EPAS1 protein. In addition, these CD4$^+$ T cells produce large amounts of the IL-31, and thus the atopic dermatitis spontaneously develops in this non-human animal.

In the present specification, the term "AND Tg" means that AND TCR is expressed, and may be AND$^{Tg-}$ or may be AND$^{Tg/Tg}$. However, in the non-human animal having the genotype of AND$^{Tg/Tg}$, there is a case where an unintentional gene is deleted through the integrated position of the AND gene on genome, and therefore AND$^{Tg/-}$ is preferable.

The non-human animal of the present embodiment may be in a form of an individual or in a form of a fertilized egg or embryo. In the above-described individual, atopic dermatitis spontaneously develops by breeding. In addition, the fertilized egg or embryo is transplanted into the uterus of the non-human animal so as to be grown into an individual, and thus can be used.

[Atopic Dermatitis Model Cell]

In one embodiment, the present invention provides an atopic dermatitis model cell which has a gene mutation in which the tri-molecular complex comprising DOCK8 protein, MST1 protein, and EPAS1 protein is not formed.

The cells of the present embodiment may be cells harvested from the above-described atopic dermatitis model non-human animal, or may be the cultured cells in which the DOCK8 gene or the MST1 gene is knocked out or knocked down. The cultured cells are not particularly limited, and for example, human cells can be used.

The cells may be, for example, cells of a hematopoietic cell type, and may be, for example, cells of a non-hematopoietic cell type such as fibroblasts.

The cells of the present embodiment can be used for, for example, a method of screening a therapeutic agent for atopic dermatitis, which will be described later.

[Non-Human Animal for Generating Atopic Dermatitis Model Animal and Method for Generating Atopic Dermatitis Model Non-Human Animal]

In one embodiment, the present invention provides a non-human animal for generating an atopic dermatitis model animal, which contains a genotype of DOCK8$^{+/-}$ TCR Tg, DOCK8$^{+/-}$, DOCK8$^{-/-}$, MST1$^{+/-}$ TCR Tg, MST1$^{+/-}$, MST1$^{-/-}$, or TCR Tg (herein, TCR Tg represents a rearranged TCR transgene). The rearranged TCR is not particularly limited as long as it is TCR that recognizes a specific antigen, and examples thereof include AND, OTII, and the like.

In a case where the above-described TCR is the AND, the non-human animal for generating an atopic dermatitis model animal of the present embodiment has a genotype of DOCK8$^{+/-}$ AND Tg, DOCK8$^{+/-}$, DOCK8$^{-/-}$, MST1$^{+/-}$ AND Tg, MST1$^{+/-}$, MST1$^{-/-}$, or AND Tg.

In the non-human animal having the genotype of DOCK8$^{+/-}$ AND Tg, DOCK8$^{+/-}$, DOCK8$^{-/-}$, MST1$^{+/-}$ AND Tg, MST1$^{+/-}$, MST1$^{-/-}$, or AND Tg, atopic dermatitis does not spontaneously develop. However, by crossing these non-human animals, an atopic dermatitis model non-human animal in which atopic dermatitis spontaneously develops appears in offspring thereof. Accordingly, it can be said that these non-human animals are a non-human animal for generating an atopic dermatitis model animal.

For example, in the non-human animal having the genotype of DOCK8$^{+/-}$ AND Tg, atopic dermatitis does not develop. However, by crossing this non-human animal with, for example, a non-human animal having the genotype of DOCK8$^{+/-}$ AND Tg, DOCK8$^{+/-}$, DOCK8$^{-/-}$, and the like, a non-human animal having the genotype of DOCK8$^{-/-}$ AND Tg appears in offspring thereof. This non-human animal is an atopic dermatitis model non-human animal in which atopic dermatitis spontaneously develops.

Similarly, in the non-human animal having the genotype of MST1$^{+/-}$ AND Tg, atopic dermatitis does not develops. However, by crossing this non-human animal with, for example, a non-human animal having the genotype of MST1$^{+/-}$ AND Tg, MST1$^{+/-}$, MST1$^{-/-}$, and the like, the non-human animal having the genotype of MST1$^{-/-}$ AND Tg appears in offspring thereof. This non-human animal is an atopic dermatitis model non-human animal in which atopic dermatitis spontaneously develops.

That is, in the one embodiment, the present invention provides a method for generating an atopic dermatitis model non-human animal, which includes crossing a non-human animal having a genotype of DOCK8$^{+/-}$ TCR Tg with a non-human animal having a genotype of DOCK8$^{+/-}$ TCR Tg, DOCK8$^{+/-}$, or DOCK8$^{-/-}$. Herein, TCR Tg represents a rearranged TCR transgene. The rearranged TCR is not particularly limited as long as it is TCR that recognizes a specific antigen, and examples thereof include AND, OTII, and the like.

Among the offspring of the non-human animal obtained by the generation method of the present embodiment, for example, a non-human animal having the genotype of DOCK8$^{-/-}$ AND Tg is an atopic dermatitis model non-human animal in which the atopic dermatitis spontaneously develops.

In addition, among the offspring of the non-human animal obtained by the generation method of the present embodiment, for example, in the non-human animal having the genotype of DOCK8$^{-/-}$ or DOCK8-/- OTII Tg, the atopic dermatitis does not develops. However, the CD4$^+$ T cells derived from such non-human animal produce large amounts of IL-31 following TCR stimulation, and therefore such non-human animal is used as a model for atopic dermatitis. In addition, after CD4$^+$ T cells derived from the non-human animal having the genotype of DOCK8$^{-/-}$, DOCK8$^{-/-}$ OTII Tg, or the like are stimulated and transferred into another non-human animal (recipient), and the like, atopic dermatitis spontaneously develops in the non-human animal (recipient), and therefore the non-human animal can be used as a model for atopic dermatitis.

In addition, in one embodiment, the present invention provides a method for generating a atopic dermatitis model non-human animal, which includes crossing a non-human animal having a genotype of MST1$^{+/-}$TCR Tg with a non-human animal having a genotype of MST1$^{+/-}$TCR Tg, MST1$^{+/-}$, or MST1$^{-/-}$. Herein, TCR Tg represents a rearranged TCR transgene. The rearranged TCR is not particularly limited as long as it is TCR that recognizes a specific antigen, and examples thereof include AND, OTII, and the like.

Among the offspring of the non-human animal obtained by the production method of the present embodiment, for example, the non-human animal having the genotype of MST1$^{-/-}$ AND Tg is an atopic dermatitis model non-human animal in which atopic dermatitis spontaneously develops.

In addition, among the offspring of the non-human animal obtained by the generating method of the present embodiment, for example, in the non-human animal having the genotype of MST1$^{-/-}$ or MST1$^{-/-}$ OTII Tg, atopic dermatitis does not develop spontaneously. However, the CD4$^+$ T cells derived from the non-human animal produce large amounts of IL-31 following TCR stimulation, and therefore the non-human animal is used as a model for atopic dermatitis. In addition, after CD4$^+$ T cells derived from the non-human animal having the genotype of MST1$^{-/-}$, MST1$^{-/-}$ OTII Tg, or the like are stimulated and transferred into another non-human animal (recipient), and the like, the atopic dermatitis is caused in the non-human animal (recipient), and therefore the non-human animal can be used as a model for atopic dermatitis.

Method for Screening Therapeutic Agent for Atopic Dermatitis

First Embodiment

In one embodiment, the present invention provides a method for screening the therapeutic agent for atopic dermatitis, which includes a step of quantitative measurements of scratching behavior of the above-described atopic dermatitis model non-human animal under administration of a test substance; and determination that the test substance is the therapeutic agent for atopic dermatitis in a case where the quantitatively determined degree of the scratching behavior is decreased, compared to the degree of scratching behavior in the absence of the test substance administration.

The scratching behavior can not be evaluated at a cell level, and thus needs to be evaluated at an individual level. As described above, the above-described atopic dermatitis model non-human animal shows extremely similar symptoms as those of the human atopic dermatitis. For this reason, by the method for screening of the present embodiment, it is possible to efficiently screen a therapeutic agent effective for the human atopic dermatitis.

As the test substance, for example, a compound library or the like can be used, and the same applies for a screening method to be described later. In addition, therapeutic agents for atopic dermatitis, which are obtained by any one of screening methods described later, or a candidate substance thereof may be used as the test substance.

A method for administering the test substance is not particularly limited, and for example, the test substance may be administered orally, may be administered to the blood by injection or the like, or may be applied to the skin.

A method for quantitative measurements of scratching behavior is not particularly limited. Examples of the method include a measurement of a frequency of the scratching behavior. The frequency of the scratching behavior can be measured by, for example, playing recordings obtained by videotaping the non-human animal for a predetermined time frame, counting the number of the scratching behaviors, and the like.

In a case where the degree of the scratching behavior is decreased by administration of the test substance, it can be determined that the corresponding test substance is a therapeutic agent for atopic dermatitis. As a mechanism of such a test substance, suppression of IL-31 production, blocking a signaling pathway downstream of IL-31 receptor, and the like are considered.

Second Embodiment

In one embodiment, the present invention provides a method for screening the therapeutic agent for atopic dermatitis, which includes a step of stimulating the TCR of the CD4$^+$ T cells from a patient with atopic dermatitis, DOCK8$^{-/-}$ CD4$^+$ T cells or MST1$^{-/-}$ CD4$^+$ T cells in the presence of the test substance to quantitatively compare the expression level of the IL-31 by the CD4$^+$ T cells; and determining that the test substance is the therapeutic agent for atopic dermatitis in a case where the expression level of the IL-31 is decreased compared to that in the absence of the test substance.

The expression level of the IL-31 may be quantitatively determined at a transcription level by, for example, quantitative real-time PCR or the like, or may be quantitatively measured at a protein level by, for example, an ELISA method or the like.

As will be described in the examples later, if the TCR of the CD4$^+$ T cells from the patient with the atopic dermatitis, DOCK8$^{-/-}$ CD4$^+$ T cells or MST1$^{-/-}$ CD4$^+$ T cells are stimulated, the expression level of the IL-31 is increased. Therefore, the substance that suppresses such increase in the expression level of the IL-31 is a candidate therapeutic agent for atopic dermatitis. In other words, the therapeutic agent for atopic dermatitis can also be called an IL-31 expression inhibitor.

The DOCK8$^{-/-}$ CD4$^+$ T cells and the MST1$^{-/-}$ CD4$^+$ T cells may be harvested from the above-described atopic dermatitis model non-human animal overproducing the IL-31, or may be cells in which the DOCK8 gene or the MST1 gene is knocked out or knocked down in an established T cell line or the like. In addition, in the DOCK8$^{-/-}$ CD4$^+$ T cells and the MST1$^{-/-}$ CD4$^+$ T cells, a rearranged TCR may be expressed.

In addition, the TCR stimulation may be performed by the antigen specific to its TCR, or may be performed with an anti-TCR antibody. Furthermore, as will be described in the examples later, by performing the TCR stimulation twice, the expression level of the IL-31 can be remarkably increased.

Third Embodiment

In one embodiment, the present invention provides a method for screening the therapeutic agent for atopic dermatitis, which includes a step of expressing the EPAS1 gene in T cells in the presence of the test substance to quantitatively compare the expression level of IL-31; and determining that the test substance is the therapeutic agent for atopic dermatitis in a case where the expression level is decreased compared to the level in the absence of the test substance.

As will be described in the examples later, if the EPAS1 gene is overexpressed in the CD4$^+$ T cells, the expression level of IL-31 is increased. Therefore, the substance that suppresses the increase in the expression level of IL-31 is a candidate therapeutic agent for atopic dermatitis. In other words, the therapeutic agent for atopic dermatitis can also be called an IL-31 expression inhibitor.

The T cells may be primary T cells, may be an established T cell line, or may be a thymocyte cell line.

Fourth Embodiment

In one embodiment, the present invention provides a method for screening the therapeutic agent for atopic dermatitis, which includes a step of expressing EPAS1 gene in cells having a reporter construct composed of IL-31 promoter region in the presence of the test substance to see quantitatively measure the expression level of the reporter gene; and determining that the test substance is the therapeutic agent for atopic dermatitis in a case where the expression level of the reporter gene is decreased compared to the level of an expression level of the reporter gene in the absence of the test substance.

As will be described in the examples later, the present inventors have clarified that IL-31 promoter activation can be induced in the presence of the EPAS1 by a reporter assay. As such, the substance that suppresses the IL-31 promoter activation is a candidate therapeutic agent for atopic dermatitis. In other words, the therapeutic agent for atopic dermatitis can also be called an IL-31 expression inhibitor.

Examples of the IL-31 promoter include a promoter of human IL-31 shown in SEQ ID NO: 2, a promoter of mouse IL-31 shown in SEQ ID NO: 3, or the like.

Examples of the reporter gene include luciferase gene. The EPAS1 gene may be, for example, human EPAS1 gene. A method for controlling EPAS1 gene expression is not particularly limited, and may be performed by, for example, introducing an expression vector of the EPAS1 gene into cells, transiently overexpressing the gene, and the like. Alternatively, the expression of the EPAS1 gene may be regulated by using a tetracycline expression induction system or the like capable of regulating ON and OFF of target gene expression by addition of tetracycline or doxycycline, for example. Alternatively, endogenously expressed EPAS1 gene may be used.

The cells are not particularly limited, and for example, human cells can be used. The cells may be, for example, cells of hematopoietic cell type, or may be, for example, cells of the non-hematopoietic cell type such as fibroblasts.

Fifth Embodiment

In one embodiment, the present invention provides a method for screening the therapeutic agent for atopic dermatitis, which includes a step of stimulating the TCR of DOCK8$^{-/-}$ T cells or MST1$^{-/-}$ T cells in the presence of the test substance to quantitatively compare the expression level of IL-31; and determining that the test substance is the therapeutic agent for atopic dermatitis in a case where the expression level of IL-31 is decreased compared to the level in the absence of the test substance.

As will be described in the examples later, when the TCR of the DOCK8$^{-/-}$ CD4$^+$ T cells or MST1$^{-/-}$ CD4$^+$ T cells is stimulated, the expression level of IL-31 is increased. Therefore, the substance that suppresses the increase in the expression level of IL-31 is a candidate therapeutic agent for atopic dermatitis. In other words, the therapeutic agent for atopic dermatitis can also be called an IL-31 expression inhibitor.

The DOCK8$^{-/-}$ T cells and the MST1$^{-/-}$ T cells may be cells harvested from the above-described atopic dermatitis model non-human animal, or may be cells in which the DOCK8 gene or the MST1 gene is knocked out or knocked down in the primary T cells, an established T cell line, a thymocyte cell line, or the like.

The TCR stimulation may be performed by the antigen specific to the TCR, or may be performed with anti-TCR antibody.

Sixth Embodiment

In one embodiment, the present invention provides a method for screening the therapeutic agent for atopic dermatitis, which includes a step of stimulating the TCR of the DOCK8$^{-/-}$ T cells or MST1$^{-/-}$ T cells expressing the reporter construct composed of the IL-31 promoter region in the presence of test substance to quantitatively measure the expression level of the reporter gene; and determining that the test substance is the therapeutic agent for atopic dermatitis in a case where the expression level of the reporter gene is decreased compared to an expression level of the reporter gene in the absence of the test substance.

As will be described in the examples later, when the TCR of the DOCK8$^{-/-}$ CD4$^+$ T cells or MST1$^{-/-}$ CD4$^+$ T cells is stimulated, the expression level of IL-31 is increased. Therefore, the substance that suppresses the increase in the expression level of IL-31 is a candidate therapeutic agent for atopic dermatitis. In other words, the therapeutic agent for atopic dermatitis can also be called an IL-31 expression inhibitor.

Examples of the IL-31 promoter include the promoter of the human IL-31 shown in SEQ ID NO: 2, the promoter of the mouse IL-31 shown in SEQ ID NO: 3, or the like. Examples of the reporter gene include the luciferase gene.

The DOCK8$^{-/-}$ T cells and the MST1$^{-/-}$ T cells may be harvested from the above-described atopic dermatitis model non-human animal, or may be cells in which the DOCK8 gene or the MST1 gene is knocked out or knocked down in the primary T cells, an established T cell line, a thymocyte cell line, or the like.

In addition, the TCR stimulation may be performed by antigen specific to the TCR, or may be performed with the anti-TCR antibody.

Seventh Embodiment

In one embodiment, the present invention provides a method for screening the therapeutic agent for atopic dermatitis, which includes a step of measuring a binding force between EPAS1 protein and DOCK8 protein in the presence of the test substance; and determining that the test substance is the therapeutic agent for atopic dermatitis in a case where the binding force is increased compared to that in the absence of the test substance.

As will be described in the examples later, in the CD4$^+$ T cells of the wild type, the complex containing the DOCK8 protein, the MST1 protein, and EPAS1 protein is formed, and therefore EPAS1 is localized within the cytoplasm. In contrast, if the above complex cannot be formed, EPAS1 is translocated into the nucleus and induces IL-31 gene expression in collaboration with SP1.

Accordingly, the substance that increases the binding force between EPAS1 protein and the DOCK8 protein can be used as a candidate therapeutic agent for atopic dermatitis. The binding force between EPAS1 protein and the DOCK8 protein can be measured by, for example, the ELISA method, immnunoprecipitation, BIACORE (registered trademark), or the like. Herein, in the ELISA method or the immunoprecipitation, it can be said that as a binding amount between EPAS1 protein and the DOCK8 protein becomes high, the binding force between them becomes high. In addition, in the measurement by the BIACORE (registered trademark), it can be said that, for example, as a $K_D$ value becomes small, the binding force becomes high.

The binding force between EPAS1 protein and the DOCK8 protein may be measured using a cell sample in which the test substance is added to a medium. Alternatively, the binding force may be measured in a test tube using purified EPAS1 protein and purified DOCK8 protein, in the presence of a test substance.

Eighth Embodiment

In one embodiment, the present invention provides a method for screening the therapeutic agent for atopic dermatitis, which includes a step of measuring a binding force between EPAS1 and the MST1 protein in the presence of the test substance; and determining that the test substance is the therapeutic agent for atopic dermatitis in a case where the binding force is increased compared to that in the absence of the test substance.

As will be described in the examples later, in the CD4$^+$ T cells of the wild type, the complex containing the DOCK8 protein, the MST1 protein, and EPAS1 is formed, and therefore EPAS1 is localized within the cytoplasm. If the above complex cannot be formed, EPAS1 is transported into the nucleus and induces IL-31 gene expression in collaboration with SP1.

Accordingly, the substance that increases the binding force between EPAS1 and the MST1 protein can be used as a candidate therapeutic agent for atopic dermatitis. The binding force between EPAS1 and the MST1 protein can be measured in the same manner as that of the binding force between EPAS1 and the DOCK8 protein, which was described above.

Ninth Embodiment

In one embodiment, the present invention provides a method for screening the therapeutic agent for atopic dermatitis, which includes a step of measuring a binding force between the DOCK8 protein and the MST1 protein in the presence of the test substance; and determining that the test substance is the therapeutic agent for atopic dermatitis in a case where the binding force is increased compared to that in the absence of the test substance.

As will be described in the examples later, in the CD4$^+$ T cells of the wild type, the complex containing DOCK8 protein, MST1 protein, and EPAS1 protein is formed, and therefore EPAS1 protein is localized within the cytoplasm. If the above complex cannot be formed, EPAS1 is transported into the nucleus and induces IL-31 gene expression in collaboration with SP1.

Accordingly, it can be said that the substance that increases the binding force between DOCK8 protein and MST1 protein also has an action of allowing the EPAS1 to localize within the cytoplasm. Therefore, the substance that increases the binding force between DOCK8 protein and MST1 protein can be used as a candidate therapeutic agent for atopic dermatitis. The binding force between DOCK8 protein and MST1 protein can be measured in the same manner as that of the binding force between EPAS1 protein and DOCK8 protein, which was described above.

Tenth Embodiment

In one embodiment, the present invention provides a method for screening the therapeutic agent for atopic dermatitis, which includes a step of measuring a binding force between EPAS1 protein and SP1 protein in the presence of the test substance; and determining that the test substance is the therapeutic agent for atopic dermatitis in a case where the binding force is decreased compared to that in the absence of the test substance.

As will be described in the examples later, if EPAS1 is transported into the nucleus, EPAS1 induces the IL-31 gene expression in collaboration with the SP1.

Accordingly, the substance that decreases the binding force between EPAS1 protein and SP1 protein can be used as a candidate therapeutic agent for atopic dermatitis. The binding force between EPAS1 and SP1 can be measured in the same manner as that of the binding force between EPAS1 and the DOCK8 protein, which was described above.

Eleventh Embodiment

In one embodiment, the present invention provides a method for screening the therapeutic agent for atopic dermatitis, which includes a step of expressing the EPAS1 gene in DOCK8$^{-/-}$ cells or MST1$^{-/-}$ cells in the presence of the test substance to quantitatively measure the abundance of nuclear EPAS1 protein; and determining that the test substance is the therapeutic agent for atopic dermatitis in a case where the abundance of the nuclear protein is decreased compared to that in the absence of the test substance.

As will be described in the examples later, the present inventors have clarified that, in normal cells, EPAS1 is localized in the cytoplasm under normal conditions, and EPAS1 is translocated into the nucleus under hypoxia. In addition, it has been clarified that, in DOCK8$^{-/-}$ cells or MST1$^{-/-}$ cells, EPAS1 is likely to translocate into the nucleus even under the normal conditions.

Accordingly, in the DOCK8$^{-/-}$ cells or MST1$^{-/-}$ cells under the normal conditions, the substance that decreases the abundance of nuclear EPAS1 protein is a candidate therapeutic agent for atopic dermatitis. Herein, the term "under normal conditions" means a condition under which an oxygen concentration is normal (about 20% (v/v)).

The DOCK8$^{-/-}$ cells or MST1$^{-/-}$ cells may be harvested from the above-described atopic dermatitis model non-human animal, or may be cells in which the DOCK8 gene or the MST1 gene is knocked out or knocked down in cultured cells. The cultured cells are not particularly limited, and for example, human cells can be used. The cells may be, for example, cells of the hematopoietic cell type, and may be, for example, cells of the non-hematopoietic cell type such as fibroblasts.

Twelfth Embodiment

In one embodiment, the present invention provides a method for screening the therapeutic agent for atopic dermatitis, which includes a step of quantitatively determining the expression level of the EPAS1 in the cells in the presence of the test substance; and determining that the test substance is the therapeutic agent for atopic dermatitis in a case where the expression level is decreased compared to that in the absence of the test substance.

As will be described in the examples later, EPAS1 induces IL-31 gene expression in collaboration with SP1 protein. Accordingly, the substance that decreases the expression level of EPAS1 is a candidate therapeutic agent for atopic dermatitis.

The expression level of the EPAS1 may be quantitatively determined at the transcriptional level by, for example, quantitative real-time PCR or the like, or may be quantitatively determined at the protein level by, for example, the Western blotting method or the like.

In addition, the cells may be harvested from the above-described atopic dermatitis model non-human animal, may be cells in which the DOCK8 gene or the MST1 gene is knocked out or knocked down, or may be cells having a wild-type genotype. The cells may be, for example, human cells. In addition, the cells may be, for example, cells of the hematopoietic cell type, and may be, for example, cells of the non-hematopoietic cell type such as fibroblasts.

[Potential Drug Target of Therapeutic Agent for Atopic Dermatitis]

In one embodiment, the present invention provides the EPAS1 as a potential drug target of the therapeutic agent for atopic dermatitis. The EPAS1 may be a gene that encodes EPAS1, or may be EPAS1.

As will be described in the examples later, the present inventors have clarified that the EPAS1 has new properties such as (1) controlling IL-31 gene expression, and (2) functioning independently of the ARNT protein involved in the neurogenesis and control of lumen formation of the trachea/salivary gland. Accordingly, the EPAS1 is suitable for use as the potential drug target of the therapeutic agent for atopic dermatitis.

[Therapeutic Agent for Atopic Dermatitis]

In one embodiment, the present invention provides a therapeutic agent for atopic dermatitis which contains an EPAS1 inhibitor as an active ingredient.

The EPAS1 inhibitor means a substance that inhibits the functions of the EPAS1. As will be described in the examples later, EPAS1 induces IL-31 gene expression in collaboration with SP1 protein. Accordingly, the EPAS1 inhibitor is a candidate therapeutic agent for atopic dermatitis.

Examples of the EPAS1 inhibitor include an expression-inhibitory substance of the EPAS1, a substance that decreases the IL-31 gene expression by EPAS1, and the like. Examples of the substance that decreases IL-31 gene expression by EPAS1 include a substance that specifically binds to EPAS1 to inhibit the EPAS1-SP1 interaction, and substance that specifically binds to SP1 to inhibit the EPAS1-SP1 interaction, and the like.

(Expression-Inhibitory Substance)

Examples of the expression-inhibitory substance include siRNA, shRNA, a ribozymes, an antisense nucleic acid, a low-molecular-weight compound, or the like. By administering these expression-inhibitory substances to a living body, EPAS1 expression can be inhibited. As a result, IL-31 gene expression can be suppressed, and therefore it is possible to treat the atopic dermatitis. Examples of the above-described low-molecular-weight compound include FM19G11 (3-[(2,4-dinitrobenzoyl)amino]-benzoic acid 2-(4-methylphenyl)-2-oxoethyl ester, [2-oxo-2-(p-tolyl) ethyl] 3-[(2,4-dinitrobenzoyl)amino]benzoate, refer to, for example, Moreno-Manzano V., et al., FM19G11, a new hypoxia-inducible factor (HIF) modulator, affects stem cell differentiation status. J. Biol. Chem., 285 (2), 1333-1342, 2010).

Small interfering RNA (siRNA) is double-stranded RNA small molecules of 21 to 23 base pairs used for gene silencing via RNA interference. The siRNA introduced into a cell binds to RNA-induced silencing complex (RISC). This complex binds to and cleaves mRNA that has a complementary sequence with the siRNA. Therefore, gene expression is suppressed in a sequence-specific manner.

The siRNA can be prepared by respectively synthesizing sense and antisense oligonucleotides with an automated DNA/RNA synthesizer, denaturing the oligonucleotides in, for example, an appropriate annealing buffer at 90° C. to 95° C. for about 1 minute, and then annealing of the oligonucleotide at 30° C. to 70° C. for about 1 to 8 hours.

Short hairpin RNA (shRNA) is a hairpin type RNA sequence used for gene silencing via RNA interference. The shRNA may be introduced into a cell by a vector and expressed with a U6 promoter or an H1 promoter, or may be prepared by synthesizing an oligonucleotide having an shRNA sequence with the automated DNA/RNA synthesizer, and self-annealing of the oligonucleotide in the same method as that of the siRNA. A hairpin structure of the shRNA introduced into the cell is cleaved into the siRNA and binds to the RNA-induced silencing complex (RISC). This complex binds to and cleaves the mRNA that has the complementary sequence with the siRNA. Therefore, gene expression is suppressed in a sequence-specific manner.

Ribozyme is RNA having catalytic activity. The ribozyme has various activities, but studies on the ribozyme as an enzyme that cleaves RNA make it possible to design the ribozyme aimed at site-specific cleavage of RNA. The ribozyme may be of a size of 400 nucleotides or more, such as a group I intron type, or M1 RNA contained in RNase P, or may have about 40 nucleotides, which is called a hammerhead type, a hairpin type, or the like.

The antisense nucleic acid is a nucleic acid complementary to a target sequence. The antisense nucleic acid can suppress the expression of a target gene by inhibition of transcription initiation by triplex formation, suppression of transcription by hybridization with a site where an opened-loop structure is locally formed by RNA polymerase, inhibition of transcription by hybridization with RNA still in the process of synthesis, suppression of splicing by hybridization with a junction of intron and exon, suppression of splicing by hybridization with a spliceosome-formation site, suppression of migration from nucleus to cytoplasm by hybridization with mRNA, suppression of splicing by hybridization with a capping site and a poly(A) addition site, inhibition of translation initiation by hybridization with a translation initiation factor binding site, inhibition of translation by hybridization with a ribosome binding site around a start codon, inhibition of elongation of a peptide chain by hybridization with a mRNA translation region and a polysome binding site, suppression of gene expression by hybridization with a site of interaction between a nucleic acid and a protein, or the like.

The siRNA, the shRNA, the ribozyme, and the antisense nucleic acid may include various chemical modifications in order to improve stability and activity thereof. For example, phosphate residues may be substituted with chemically modified phosphate residues such as phosphorothioate (PS), methylphosphonate, and phosphorodithionate, in order to prevent degradation by a hydrolase such as a nuclease. In addition, at least a part thereof may be constituted by a nucleic acid analog such as peptide nucleic acid (PNA).

(Specific Binding Substance)

The substance that specifically binds to EPAS1 can inhibit its association with, for example, SP1 protein through the binding to EPAS1. As a result, IL-31 expression can be suppressed, and therefore it is possible to treat the atopic dermatitis. Similarly, the substance that specifically binds to SP1 can inhibit its association with, for example, EPAS1 through the binding to SP1. As a result, IL-31 gene expression can be suppressed, and therefore it is possible to treat the atopic dermatitis.

Examples of the specific binding substance include an antibody, an antibody fragment, an aptamer, a low-molecular-weight compound, or the like. The antibody can be produced by, for example, immunizing an animal such as a mouse with an antigen. Alternatively, the antibody can be produced by screening antibody libraries such as phage libraries, or the like.

Examples of the antibody fragment include Fv, Fab, scFv, or the like. The above-described antibody or antibody fragment may be polyclonal or monoclonal. In addition, the above-described antibody or antibody fragment may be an antibody or antibody fragment to which a compound such as polyethylene glycol is bound. By being bound with the polyethylene glycol, it becomes possible to increase blood stability, for example.

The aptamer is a substance having a specific binding ability with respect to a labeled substance. Examples of the aptamer include a nucleic acid aptamer, a peptide aptamer, or the like. The nucleic acid aptamer having the specific binding ability with respect to EPAS1 can be selected by, for example, the systematic evolution of ligands by exponential enrichment (SELEX) method or the like. In addition, the peptide aptamer having the specific binding ability with respect to EPAS1 can be selected by, for example, a yeast two-hybrid method, or the like.

In addition to the above-described examples, the specific binding substance may be obtained by screening a compound library or the like, with a binding property to a target substance as a reference for example.

(Substance Decreasing IL-31 Gene Expression by EPAS1 Protein)

It can be said that a substance that decreases EPAS1-mediated IL-31 gene expression is a candidate therapeutic agent for atopic dermatitis. Such a substance can be screened from the compound library or the like by any of the screening methods described above, for example.

(Dosage Form and Dosage)

The above-described therapeutic agent for atopic dermatitis may itself be administered to a living body, or may be administered to a living body in a form of being formulated as a pharmaceutical composition mixed with a pharmaceutically acceptable carrier.

The pharmaceutical composition may be formulated into a dosage form to be used orally, such as tablets, capsules, elixirs, or microcapsules, and may be formulated into a dosage form to be used parenterally, such as injections, ointments, or patches.

Examples of the pharmaceutically acceptable carrier include solvents such as sterilized water and physiological salt solution; binders such as gelatin, corn starch, tragacanth gum, and gum arabic; excipients such as crystalline cellulose; swelling agents such as corn starch, gelatin, and alginic acid, or the like.

The pharmaceutical composition may contain an additive. Examples of the additive include lubricants such as magnesium stearate; sweeteners such as sucrose, lactose, and saccharin; flavoring agents such as peppermint and *Gault-*

*heria adenothrix* oil; stabilizers such as benzyl alcohol and phenol; buffers such as phosphate, and sodium acetate; solubilizers such as benzyl benzoate and benzyl alcohol; antioxidants; preservatives; surfactants; emulsifiers, or the like.

The pharmaceutical composition can be formulated by appropriately combining the above-described carriers and additives, and mixing the carriers and additives in unit dosage form required for generally accepted pharmaceutical practice.

In a case where the pharmaceutical composition is the injection, examples of a solvent for the injection include isotonic solutions containing adjuvants such as physiological salt solution, glucose, D-sorbitol, D-mannose, D-mannitol, and sodium chloride. The solvent for the injection may contain alcohols such as ethanol; polyalcohols such as propylene glycol and polyethylene glycol; nonionic surfactants such as polysorbate 80 (trademark) and HCO-50, or the like.

Administration of the therapeutic agent for atopic dermatitis to the patient can be carried out intranasally, transbronchially, intramuscularly, transdermally, or orally by methods known to those skilled in the art, in addition to intraarterial injection, intravenous injection, subcutaneous injection, or the like.

The dosage of the therapeutic agent for atopic dermatitis varies depending on symptoms, but in the case of oral administration, the dosage is generally, for example, 0.1 to 100 mg, for example, 1 to 50 mg, for example, 1 to 20 mg, or the like per day for an adult (body weight of 60 kg).

In the case of parenteral administration, the single dosage varies depending on a subject to be administered, a target organ, a symptom, and an administration method. For example, in the form of the injection, the dosage of about, for example, 0.01 to 30 mg, for example, 0.1 to 20 mg, or, for example, 0.1 to 10 mg per day is administered for an adult (body weight of 60 kg) by intravenous injection or local injection.

Other Embodiments

In one embodiment, the present invention provides a method for treating atopic dermatitis, which includes administering an effective dose of the EPAS1 inhibitor to patients who need to be treated or to animals with the atopic dermatitis.

In such embodiment, the present invention provides a method for inhibiting IL-31 gene expression, which includes administering an effective dose of the EPAS1 inhibitor to patients who need to be treated or to animals with the atopic dermatitis.

In such embodiment, the present invention provides the EPAS1 inhibitor for treating the atopic dermatitis.

In such embodiment, the present invention provides use of the EPAS1 inhibitor for producing the therapeutic agent for atopic dermatitis.

EXAMPLES

Next, the present invention will be described in more detail by showing experimental examples, but the present invention is not limited to the following experimental examples.

[Materials and Methods]
(Mice)

DOCK8$^{-/-}$ mice were developed in advance (refer to NPL 2). Hetero mice (DOCK8$^{+/-}$) were backcrossed onto a C57BL/6 background for more than nine generations. DOCK8$^{+/-}$ mice were crossed with AND TCR Tg mice to obtain DOCK8$^{+/-}$ AND Tg mice or DOCK8$^{-/-}$ AND Tg mice. EPAS1$^{lox/lox}$ mice were obtained from the Jackson Laboratory and crossed with CD4-Cre Tg mice to obtain CD4-Cre$^+$ EPAS11$^{lox/lox}$DOCK8$^{-/-}$ AND Tg mice. Mice were bred under specific-pathogen-free (SPF) environments in the animal facility of Kyushu University. Age- and sex-matched littermates were used as controls. All animal experiments were approved by the committee of Ethics of Animal Experiments, Kyushu University, and carried out according to guidelines. Mice were selected randomly and assigned to each experimental group according to genotype. Experimenters who performed the experiments were blinded to mouse genotypes.

(Measurement of Scratching Behavior)

Mice were put into an acrylic cage of 11×14×20 cm for at least 1 hour for acclimation, and then the behaviors of the mice were videotaped. The video was played for determination of a total number of the scratching behaviors per 2-hour period.

(Histology and Immunofluorescence Staining)

Skin tissues were fixed in 4% (w/v) paraformaldehyde and embedded in paraffin blocks. Sections having a thickness of 3 μm were stained with hematoxylin and eosin, and observed with a bright-field microscope. For immunofluorescence analyses, tissues were embedded in OCT compound (Sakura Finetech) and frozen in liquid nitrogen. Frozen sections having a thickness of 10 μm were fixed in 4% (w/v) paraformaldehyde for 30 minutes and blocked with 10% goat serum for 1 hour. The sections were then stained with phycoerythrin (PE)-conjugated anti-mouse CD3 antibody (model "17A2", Biolegend), fluorescein isothiocyanate (FITC)-conjugated anti-mouse CD45R/B220 antibody (model "RA3-6B2", BD Biosciences), FITC-conjugated anti-mouse CD8a antibody (model "53-6.7", BD Biosciences), or biotinylated anti-mouse CD4 antibody (model "H129.19", BD Biosciences), followed by incubation with Alexa Fluor 488-conjugated streptavidin (Thermo Fisher Scientific). For EPAS1 staining, mouse embryonic fibroblasts (MEF) (3×10$^5$ cells/mL) were cultured on the poly-L-lysine coated glass-bottom dishes (Matsunami) in 1% 02 environment for 30 hours, fixed with 4% (w/v) paraformaldehyde for 30 minutes, and permeabilized with 0.2% Triton X-100 for 30 minutes. After being blocked with 10% goat serum for 1 hour at room temperature, cells were then stained with 4',6-diamidino-2-phenylindole (DAPI; Dojindo Laboratories) and rabbit anti-EPAS1 antibody (NOVUS Biologicals), followed by incubation with Alexa Fluor 488-conjugated donkey anti-rabbit IgG antibody (Fab fragment, Jackson ImmunoReseach). All images were captured with a laser scanning confocal microscope (Carl Zeiss).

(ELISA)

IL-31 concentrations in serum samples and cell culture supernatants were measured with ELISA kits (R&D Systems for human samples and USCN for mouse samples), according to the manufacturer's instructions. Measurement of the concentrations of serum IgE and IgG2b was carried out as follows. First, the serum samples were serially diluted and placed in 96-well plates coated with goat anti-mouse IgE antibody or goat anti-mouse Ig (IgM+IgG+IgA, H+L) antibody. After 2-hour incubation, the wells were washed with phosphate-buffered saline (PBS) and incubated with alkaline phosphatase-conjugated rat anti-mouse IgE antibody or goat anti-mouse IgG2b antibody (Southern Biotech).

(Flow Cytometry)

The following antibodies and reagents were used. FITC-conjugated anti-mouse CD45R/B220 antibody (model "RA3-6B2"), FITC-conjugated anti-mouse CD4 antibody (model "RM4-5"), biotinylated anti-mouse CD4 antibody (model "RM4-5"), PE-conjugated anti-mouse CD8a antibody (model "53-6.7"), PE-conjugated anti-mouse CD44 antibody (model "IM7"), FITC-conjugated anti-mouse CD62L antibody (model "MEL-14"), FITC-conjugated anti-mouse Vα1 antibody (model "RR8-1"), FITC-conjugated anti-mouse Vα2 antibody (model "B20.1"), biotinylated anti-mouse Vβ3 antibody (model "KJ25"), biotinylated anti-mouse Vβ5 antibody (model "MR9-4"), and allophycocyanin (APC)- or PerCP-cyanine5.5-conjugated streptavidin antibody (all of which were from BD Biosciences), and biotinylated anti-mouse CD90.2/Thy1.2 (model "30-H12", eBioscience). Before staining with the antibodies, cells were incubated for 10 minutes on ice with anti-Fcγ III/II receptor antibody (model "2.4G2", BD Biosciences) to block Fc receptors. Flow cytometric analyses were carried out using FACS Calibur (trade name, BD Biosciences).

(Preparation and Culture of Cells)

Mouse CD4$^+$ T cells were isolated from the spleen and peripheral lymph nodes by magnetic sorting with Dynabeads mouse CD4, followed by treatment with DETACHaBEAD mouse CD4 (Life Technologies), and suspended in RPMI 1640 medium (Wako) containing 10% heat-inactivated fetal calf serum (FCS), 50 μM 2-mercaptoethanol (Nacalai Tesque), 2 mM L-glutamine (Life Technologies), 100 U/mL 1 penicillin, 100 μg/mL streptomycin, 1 mM sodium pyruvate (Life Technologies), and MEM non-essential amino acids (Life Technologies). For performing primary stimulation, CD4$^+$ T cells ($3 \times 10^5$ cells/well) were cultured in a 24-well plate with T cell-depleted, irradiated spleen cells ($5 \times 10^6$ cells/well) in the presence of MCC88-103 peptide (SEQ ID NO: 1, 3 μg/mL) or OVA323-339 peptide (SEQ ID NO: 4, 1 μg/mL).

For performing secondary stimulation, CD4$^+$ T cells recovered from the culture were re-stimulated with plate-bound anti-CD3ε antibody (model "145-2C11", eBioscience, 1 μg/mL), and with anti-CD28 antibody (model "37.51, BD Biosciences, 1 μg/mL) for some cases.

T cell proliferation assays were carried out by cultivating CD4$^+$ T cells ($5 \times 10^4$ cells/well) with T cell-depleted, irradiated spleen cells ($1 \times 10^6$ cells/well) in the presence or absence of various concentrations of the predetermined peptide for 66 hours. [$^3$H]-thymidine (0.037 MBq) was added during the final 18 hours of the culture, and the incorporated radioactivity was measured with a liquid scintillation counter.

Human peripheral blood samples were collected from atopic dermatitis patients and healthy volunteers in compliance with Institutional Review Board protocols of the facility. Human peripheral blood mononuclear cells (PBMC) were separated by Percoll (GE Healthcare) gradient centrifugation. The CD4$^+$ T cells were isolated from PBMCs by magnetic sorting by using Dynabeads human CD4 followed by treatment with DETACHaBEAD human CD4 (Life Technologies).

After being suspended in complete RPMI 1640 medium, CD4$^+$ T cells ($3 \times 10^5$ cells/well) were stimulated in a 24-well plate coated with anti-human CD3ε antibody (model "Hit3a", Tonbo Biosciences) for 6 hours. In some experiments, the CD4$^+$ T cells were treated with EPAS1 inhibitors, FM19G11 or HIFVII at 30 μM (both from Calbiochem).

These experiments were approved by the Ethics committee of Kyushu University Hospital, and a written informed consent was obtained from all patients and the healthy volunteers.

(RT-PCR and Quantitative Real-Time PCR)

Total RNA was extracted using ISOGEN (trade name, Nippon Gene). After treatment with RNase-free DNase I (Life Technologies), RNA samples were reverse-transcribed with oligo (dT) primers (Life Technologies) and SuperScript III reverse transcriptase (Life Technologies) for amplification by PCR.

Sequence numbers of base sequences of primers used for RT-PCR of each gene are listed in Table 1. Note that, in the present specification, GAPDH is an abbreviation for glyceraldehyde triphosphate dehydrogenase.

TABLE 1

| Gene | Sense primer | Antisense primer |
| --- | --- | --- |
| Mouse GAPDH | SEQ ID NO: 5 | SEQ ID NO: 6 |
| Mouse IL-31 | SEQ ID NO: 7 | SEQ ID NO: 8 |
| Mouse EPAS1 | SEQ ID NO: 9 | SEQ ID NO: 10 |
| Mouse MST1 | SEQ ID NO: 11 | SEQ ID NO: 12 |

Real-time PCR was performed using ABI PRISM 7,000 Sequence Detection System (trade name, Applied Biosystems) and SYBR Green PCR Master Mix (Applied Biosystems).

Sequence numbers of base sequences of primers used for real-time PCR are listed in Table 2. Note that, in the present specification, HPRT is an abbreviation of hypoxanthine-guanine phosphoribosyltransferase.

TABLE 2

| Gene | Sense primer | Antisense primer |
| --- | --- | --- |
| Human GAPDH | SEQ ID NO: 13 | SEQ ID NO: 14 |
| Human IL-31 | SEQ ID NO: 15 | SEQ ID NO: 16 |
| Human IL-2 | SEQ ID NO: 17 | SEQ ID NO: 18 |
| Mouse HPRT | SEQ ID NO: 19 | SEQ ID NO: 20 |
| Mouse IL-31 | SEQ ID NO: 21 | SEQ ID NO: 22 |
| Mouse IL-4 | SEQ ID NO: 23 | SEQ ID NO: 24 |
| Mouse IL-2 | SEQ ID NO: 25 | SEQ ID NO: 26 |

The expression levels of human and mouse target genes were normalized based on expression levels of GAPDH and HPRT. Sequence detection software attached to real-time PCR equipment was used for analyses.

(Microarray Analysis)

Total RNA was extracted using ISOGEN (trade name, Nippon Gene). cRNA was amplified and labelled using a commercially available kit (model "Low Input Quick Amp Labeling Kit", Agilent Technologies).

The cRNA was then hybridized to a microarray (model "44K 60-mer oligomicroarray (Whole Mouse Genome oligo DNA Microarray Kit Ver 2.0", Agilent Technologies). The hybridized microarray slides were scanned using a scanner manufactured by Agilent Technologies. The relative hybridization intensities and background hybridization values were calculated using software (model "Feature Extraction Software version 9.5.1.1", Agilent Technologies). Raw signal intensities and flags for each probe were calculated based on the hybridization intensities and spot information, according to the procedures recommended by Agilent Technologies. To identify up- or down-regulated genes in experimental samples, the present inventors calculated Z-scores and ratios based on the normalized signal intensities of each probe (up-regulated genes, Z-score >2.0 and ratio >1.5-fold; down-regulated genes, Z-score <−2.0 and ratio <0.66-fold).

(Knockdown of Target Genes by siRNAs)

To knock down EPAS1 gene or MST1 gene expression in DOCK8$^{-/-}$ or DOCK8$^{+/-}$ AND Tg CD4$^+$ T cells, a commercially available kit (trade name, model "Accell siRNA SMART pool", model "E-040635-00-0005" (for EPAS1) or model "E-059385-00-0005" (for MST1) (Dharmacon) was used.

Transfection was performed according to the manufacturer's instructions using oligonucleotide (trade name "Accell Red Non-targeting siRNA", model "D-001960-01-05", Dharmacon) as a control.

Briefly, DOCK8$^{-/-}$ or DOCK88$^{+/-}$ AND Tg CD4$^+$ T cells ($3\times10^5$ cells/well) were cultured with T cell-depleted, irradiated spleen cells ($5\times10^6$ cells/well) and MCC88-103 peptide (SEQ ID NO: 1, 3 µg/mL) in medium (model "Accell siRNA Delivery Media", Dharmacon) supplemented with 2.5% FCS. The siRNA or the control oligonucleotide was then added to the culture at the final concentration of 1 µM. After 4 days of the culture, viable CD4$^+$ T cells were recovered and re-stimulated with plate-bound anti-CD3ε antibody (model "145-2C11", 1 µg/mL) and anti-CD28 antibody (model "37.51", 1 µg/mL) for 3 hours. The knockdown efficacy was checked by RT-PCR.

In a case of knockdown of SP1 gene and ARNT gene expression in MEFs, the siRNAs (trade name "On-Target plus SMART pool", model "L-040633-02-0005" (for SP1) or "L-040639-01-0005" (for ARNT), Dharmacon) and irrelevant oligonucleotide (trade name "BLOCK-iT Alexa Fluor Red", Life Technologies) were used.

For transfection, first, 400 µL of the siRNA solution (150 nM) in serum-free DMEM medium (Wako) was mixed with 5 µL DharmaFect transfection reagent, and left to stand for 20 minutes at room temperature. This solution was added drop-wise to MEFs ($3\times10^5$ cells/well) suspended in 1.6 mL DMEM medium containing 10% FCS. Then, cells were incubated for 24 hours at 37° C. before transient transfection for luciferase reporter assays. The knockdown efficacy was checked by Western blot analyses.

(Plasmids and Transfection)

To generate mouse IL-31 reporter plasmid (pGL4.10-IL-31), a promoter region of the mouse IL-31 gene from position 1,367 to 1 was amplified by PCR and subcloned into pGL4.10 [luc2] vector (Promega). Deletions and mutations in the IL-31 promoter region were created by PCR. These plasmids were transfected into MEFs with Lipofectamine 2,000 reagent (Life Technologies) for luciferase reporter assays.

The pcDNA vector (Invitrogen) was used to create expression vectors encoding FLAG-tagged human and mouse EPAS1 (pcDNA-EPAS1) or its deletion mutants, HA-tagged mouse DOCK8 (pcDNA-DOCK8), FLAG-tagged or V5-tagged mouse MST1 (pcDNA-MST1), and HA-tagged human ARNT (pcDNA-ARNT).

These expression constructs were transfected into HEK-293T cells with polyethyleminine for immunoprecipitation.

The pBJ vector (pBJ-neo) encoding neomycin was used to create expression vectors encoding WT (wild type) DOCK8 and its mutants, mutants (ΔN) lacking the N-terminal 527 amino acid residues of DOCK8, and mutants (ΔDHR2) lacking amino acid residues from 1,535 to 2,100 of DOCK8.

The retroviral vector pMX was used to generate pMX-EPAS1-IRES-GFP (green fluorescent protein) plasmid.

This plasmid DNA was transfected into Platinum-E packaging cells (COSMO BIO) with FuGENE 6 transfection reagent (Promega). The cell culture supernatants were harvested 48 hours after transfection, supplemented with polybrene (5 µg/mL) and IL-2 (5 ng/mL), and were used to infect the CD4$^+$ T cells.

After centrifugation at 2000 rpm for 1 hour, plates were incubated for 8 hours at 32° C. and for 16 hours at 37° C. Two additional retroviral infections were performed at daily intervals, and the GFP-positive CD4$^+$ T cells were sorted by FACSAria (BD Biosciences) for RNA extraction 30 hours after the third transfection.

To generate the retroviral vector pSUPER retro-puro sh MST1, a double-stranded DNA fragment consisting of oligonucleotides (SEQ ID NOs: 27 and 28) corresponding to specific regions of MST1 was ligated to the pSUPER retro-puro vector (OligoEngine) at the Bgl II and Hind III sites.

MEFs were retrovirally transduced with pSUPER retro-puro sh MST1 as described above.

(Luciferase Reporter Assays)

MEFs were co-transfected with pRL-SV40-*Renilla* luciferase plasmid (0.1 µg, Promega) and pGL4.10-IL-31 (2 µg), and pcDNA-EPAS1 or its mutants (2 µg).

For transfection, these plasmid DNAs were mixed with Lipofectamine 2,000 transfection reagent (5 µL) in 500 µL of the Opti-DMEM medium (Life Technologies), and left to stand for 20 minutes at room temperature, and the mixture was added drop-wise to MEFs ($3\times10^5$ cells/well) cultured in 1.5 mL of DMEM medium containing 1% FCS. 6 hours after transfection, cells were suspended in DMEM containing 10% FCS and incubated for additional 24 hours. In some experiments, pGL4.10-IL-31-derived mutants were used.

A total amount of plasmid DNA was equalized by the control vector. Luciferase activity was measured with a commercially available kit (model "Dual-Luciferase Reporter Assay System", Promega) according to the manufacture's protocols.

(Immunoblotting and Immunoprecipitation)

Cells were lysed in 20 mM Tris-HCl buffer (pH 7.5) containing 1% Triton X-100, 150 mM NaCl, 1 mM EDTA, 1 mM EGTA, 2.5 mM sodium pyrophosphate, 1 mM β-glycerophosphate, 1 mM Na$_3$VO$_4$, and complete protease inhibitors (Roche).

After centrifugation, the supernatants were mixed with an equal volume of 2× sample buffer (125 mM Tris-HCl, 0.01% bromophenacyl bromide, 4% SDS, 20% glycerol, and 200 µM dithiothreitol). Samples were boiled for 5 minutes and analyzed by inmmunoblotting.

The following antibodies were used. Rabbit anti-EPAS1 antibody (Novus Biologicals), rabbit anti-SP1 antibody (Millipore), rabbit anti-ARNT antibody (Cell Signaling), rabbit anti-MST1 antibody (Cell Signaling), goat anti-bactin antibody (model "I-19", Santa Cruz) rat anti-HA antibody (model "3F10", Roche), anti-FLAG antibody (MBL) and anti-V5 antibody (Life Technologies).

Polyclonal antibody against DOCK8 was produced by immunizing rabbits with KLH-coupled synthetic peptide corresponding to the C-terminal sequence of human and mouse DOCK8 (2081 to 2100, SEQ ID NO: 29). In some experiments, immunoblotting was performed by immunoprecipitation of HEK-293T cell lysates with the appropriate antibodies. Signals were measured using software (software name "ImageJ", http://imagej.nih.gov/ij/) and normalized to β-actin.

(EMSA)

Nuclear extracts were prepared from MEFs using a standard method. Briefly, cells were rinsed with PBS, resuspended in buffer A (10 mM HEPES-K$^+$, pH 7.9, 10 mM KCl, 0.1 mM EDTA, 0.1 mM EGTA, 0.5 mM DTT, 1 mM PMSF)

and incubated on ice for 15 minutes. Cells were then lysed by adding NP-40 to a final concentration of 0.67% and immediately vortexing for 10 seconds.

The lysate was centrifuged at 20,000 g for 30 seconds at 4° C. to pellet nuclei. Nuclei were resuspended in buffer B (20 mM HEPES-K$^+$, pH 7.9, 400 mM NaCl, 1 mM EDTA, 1 mM EGTA, 1 mM DTT, 1 mM PMSF), incubated for 15 minutes on ice with intermittent agitation and centrifuged at 20,000 g for 5 minutes at 4° C. to prepare nuclear extracts.

In addition, a DNA probe (WT, SEQ ID NO: 30) corresponding to the mouse IL-31 promoter region containing the consensus SP1-binding sequence was labelled with [$\gamma$-$^{32}$P] ATP (Perkin Elmer) using T4 polynucleotide kinase (Promega) and purified using illustra (trademark) MicroSpin (trademark) G-25 columns (GE Healthcare).

Protein-DNA binding was carried out as follows. 4 μg nuclear extracts were incubated in 9 μL of binding buffer (20 mM HEPES-K$^+$, pH 7.9, 50 mM KCl, 3 mM MgCl2, 10% glycerol, 1 mM DTT) supplemented with 2 μg poly(dI-dC) (Sigma-Aldrich) in the presence or absence of unlabelled competitor DNA (WT (SEQ ID NO: 30) or its mutant (SEQ ID NO: 31)) for 2.5 hours on ice, before addition of 1 μL of [$^{32}$P]-labelled probe (0.035 pmol) and incubation at room temperature for 20 minutes.

Protein-DNA complexes were separated on a 6% native polyacrylamide/0.5×TBE gel at 4° C., dried onto a filter paper at 80° C. for 2 hours under vacuum and analyzed with the BAS2,000 BIO Imaging Analyzer (Fuji Photo Film).

For supershift assays, 3 μg anti-SP1 antibody (Millipore) or 6 μg anti-GFP antibody (Invitrogen) as a control were added to nuclear extracts and incubated on ice for 2.5 hours before addition of radiolabelled probes.

(Chromatin Immunoprecipitation)

MEFs of wild type (WT) and EPAS1$^{-/-}$ were cultured in 10 mL of DMEM medium containing 10% FCS for 12 hours in two 100 mm culture dishes, followed by culturing in 1% O$_2$ environment for 24 hours. The cells were then cross-linked with 1% formaldehyde for 10 minutes at room temperature, and then glycine was added and reacted at room temperature for 5 minutes to neutralize. The cells were then washed with PBS containing protease inhibitors, and then nuclei were extracted using a commercially available kit (model "Magna ChIP (trademark) HiSens kit", Millipore) according to the manufacturer's protocol.

Isolated nuclei were resuspended in sonication buffer and sonicated using an ultrasound homogenizer (model "Cell disruptor 200", Branson) with 16 sets of 10 pulses using the power set at "6" on ice for shearing chromatin DNA. Then, after centrifugation at 10,000 g for 10 minutes at 4° C., sheared chromatin DNA was recovered and treated with RNase and proteinase K for quantifying DNA content.

The immunoprecipitation was carried out as follows. First, 3 to 7 μg chromatin DNA was mixed with magnetic Protein A/G beads preincubated with 2 μg anti-SP1 antibody (model "07-645", Millipore) or 1 μg rabbit normal IgG (Cell Signaling) and incubated at 4° C. overnight.

The magnetic beads were washed three times with buffer containing physiologic salt and once with low salt buffer. Then, the magnetic beads were treated with proteinase K at 65° C. for 2 hours, and heated at 95° C. for 15 minutes for inactivation of proteinase K and elution of bound chromatin DNA.

Eluted DNA was analyzed by quantitative real-time PCR using primers (SEQ ID NOs: 32 and 33) which amplify the mouse IL-31 promoter (−249/−97).

(Statistical Analysis)

Differences between groups were compared by unpaired one-tailed Student's t test (in a case of two groups) or a one-way analysis of variance (in a case of multiple groups), followed by post hoc Bonferroni test. In addition, P values less than 0.05 were considered significant.

I. Atopic Dermatitis in DOCK8$^{-/-}$ AND Tg Mice

Experimental Example 1

The AND is the TCR that recognizes a peptide (SEQ ID NO: 1) consisting of 88th to 103rd amino acids of Moth cytochrome c (MCC), which forms a complex with MHC class II I-E$^\kappa$ molecule.

In order to investigate the influence of deficiency of DOCK8 on CD4$^+$ T cell differentiation and function, the present inventors crossed AND TCR transgenic (Tg) mice with DOCK8$^{-/-}$ mice. As a result, the present inventors revealed that DOCK8$^{-/-}$ AND Tg mice spontaneously develop severe atopic dermatitis by 14 to 15 weeks of age.

Figure 1:
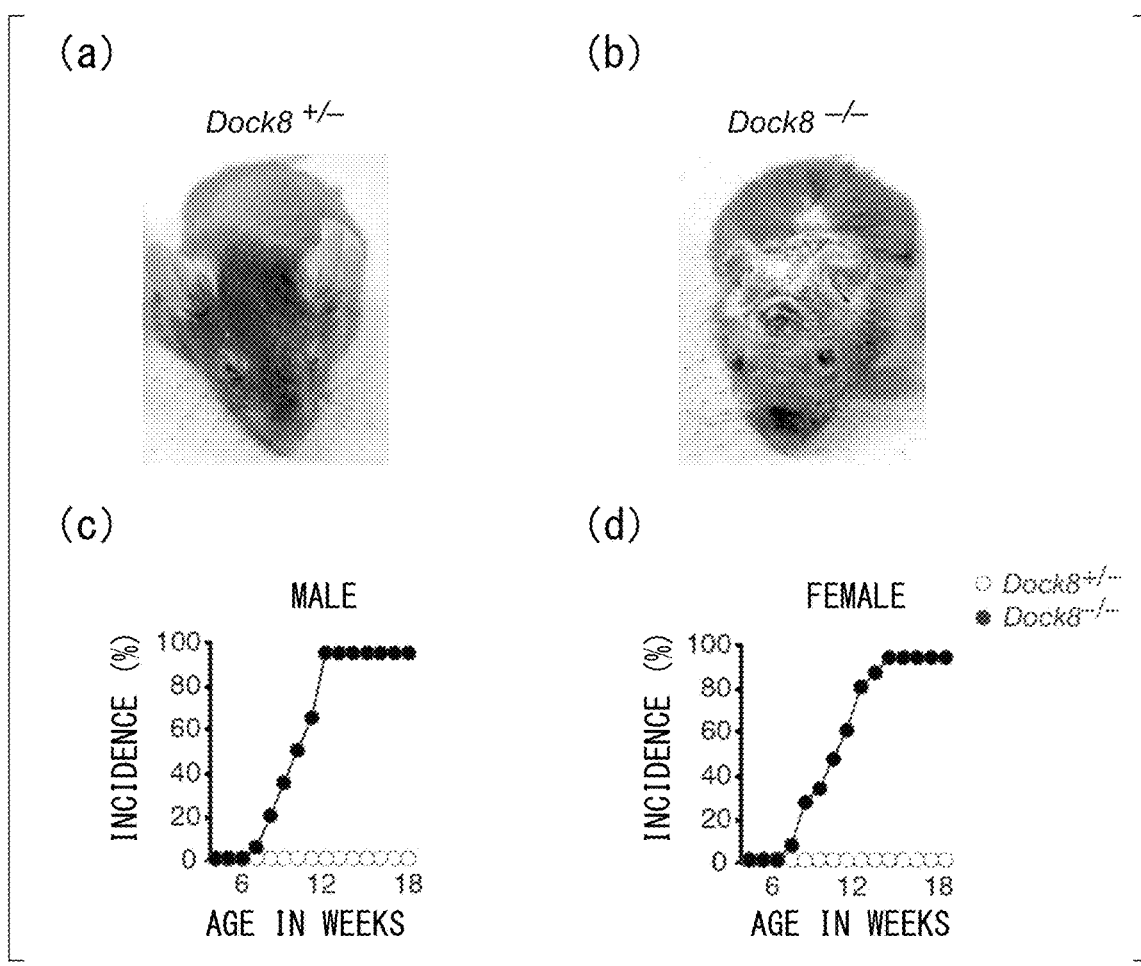
FIG. 1 shows results of Experimental Example 1. (a) is a representative photograph of 18-week-old DOCK8$^{+/-}$ AND Tg mice. (b) is a representative photograph of 18-week-old DOCK8$^{-/-}$ AND Tg mice. (c) is a graph showing the incidence of atopic dermatitis of male mice (n=20) having a genotype of DOCK8$^{-/-}$ AND Tg. (d) is a graph showing the incidence of the atopic dermatitis of female mice (n=15) having the genotype of DOCK8$^{-/-}$ AND Tg.

(a) of FIG. 1 is a representative photograph of 18-week-old DOCK8$^{+/-}$ AND Tg mice. (b) of FIG. 1 is a representative photograph of 18-week-old DOCK8$^{-/-}$ AND Tg mice.

In addition, (c) of FIG. 1 is a graph showing the incidence of atopic dermatitis in male mice (n=20) having a genotype of DOCK8$^{-/-}$ AND Tg. (d) of FIG. 1 is a graph showing the incidence of the atopic dermatitis in female mice (n=15) having the genotype of DOCK8$^{-/-}$ AND Tg. In (c) and (d) of FIG. 1, the same number of DOCK8$^{+/-}$ AND Tg littermates were analyzed as controls.

As shown in (c) and (d) of FIG. 1, there was no significant difference in incidence between males and females. The atopic dermatitis developed at 7 to 8 weeks of age and deteriorated with increases of age. On the other hand, the same as DOCK8$^{-/-}$ mice, the atopic dermatitis did not develop in DOCK8$^{+/-}$ AND Tg mice.

Experimental Example 2

Figure 2:
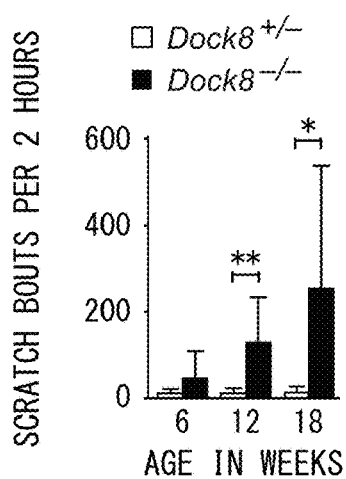
FIG. 2 is a graph showing quantitative measurements of scratching behaviors of DOCK8+/− AND Tg mice and DOCK8−/− AND Tg mice in Experimental Example 2.

The scratching behavior of DOCK8$^{-/-}$ AND Tg mice was analyzed. FIG. 2 is a graph showing quantitative measurements of scratching behaviors per 2 hours of DOCK8$^{+/-}$ AND Tg mice and DOCK8$^{-/-}$ AND Tg mice at 6 weeks of age (n=8), 12 weeks of age (n=6), and 18 weeks of age (n=8). Values in the graph represent average value±standard deviation. The symbol "*" in the drawing indicates that there is a significant difference at a risk ratio of less than 5%. As shown in FIG. 2, DOCK8$^{-/-}$ AND Tg mice exhibited severe scratching behaviors at 12 and 18 weeks of age. This result indicates that this dermatitis is very itchy.

Experimental Example 3

Figure 3:
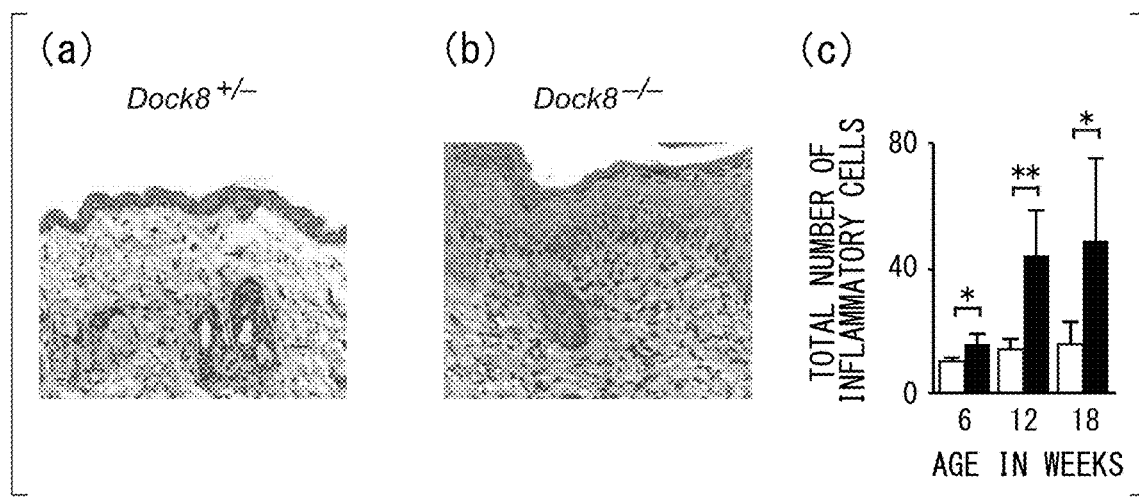
FIG. 3 shows results of Experimental Example 3. (a) and (b) are photographs of the results of hematoxylin and eosin staining of the skin of the 18-week-old DOCK8$^{+/-}$ AND Tg mice (a) and the DOCK8$^{-/-}$ AND Tg littermate mice (b). (c) is a graph showing total number of inflammatory cells per 0.25 mm$^2$ in the skin of the DOCK8$^{+/-}$ AND Tg mice and the DOCK8$^{-/-}$ AND Tg mice.

Histological and immunohistochemnical analysis of the skin of DOCK8$^{-/-}$ AND Tg mice was performed. (a) and (b) of FIG. 3 are photographs of the results of hematoxylin and eosin staining of the skin of the 18-week-old DOCK8$^{+/-}$ AND Tg mice ((a) of FIG. 3) and the DOCK8$^{-/-}$ AND Tg littermate mice ((b) of FIG. 3). Scale bar indicates 50 μm.

(c) of FIG. 3 is a graph showing the total number of inflammatory cells per 0.25 mm$^2$ in the skin of the DOCK8$^{+/-}$ AND Tg mice (n=4 at each week of age) and the DOCK88$^{-/-}$ AND Tg mice (n=4 at each week of age). Values in the graph represent average value±standard deviation. The symbol "*" in the drawing indicates that there is a significant difference at a risk rate of less than 5%, and the symbol "**" indicates that there is a significant difference at a risk rate of less than 1%.

(a) and (b) of FIG. 4 are fluorescence microscopy photographs obtained by staining the skin of the DOCK8$^{+/-}$ AND Tg mice ((a) of FIG. 4) and the DOCK8$^{-/-}$ AND Tg mice ((b) of FIG. 4) with anti-CD3 antibody and anti-CD4 antibody. Scale bar indicates 50 µm. As a result, it was revealed that CD4$^+$ T cells infiltrated into the skin of DOCK8$^{-/-}$ AND Tg mice.

Subsequently, infiltration of CD8$^+$ T cells and B cells was examined. (c) and (d) of FIG. 4 are fluorescence microscopy photographs obtained by staining the skin of the DOCK8$^{+/-}$ AND Tg mice ((c) of FIG. 4) and the DOCK8$^{-/-}$ AND Tg mice ((d) of FIG. 4) with anti-CD3 antibody, anti-CD8 antibody, and anti-B220 antibody. Scale bar indicates 50 µm. As a result, it was recognized that there was no infiltration of CD8$^+$ T cells and B cells on the skin of DOCK8$^{-/-}$ AND Tg mice.

Based on the above results, it became clear that, in the skin of DOCK8$^{-/-}$ AND Tg mouse, epidermal hyperplasia accompanied with massive infiltration of CD4$^+$ T cells and hyperkeratosis were recognized, as in the skin of patients with atopic dermatitis.

Experimental Example 4

The concentrations of IgE and IgG2b in the sera of DOCK88$^{+/-}$ AND Tg mice and DOCK8$^{-/-}$ AND Tg mice were measured. (a) and (b) of FIG. 5 are graphs showing the concentrations of IgE ((a) of FIG. 5) and IgG2b ((b) of FIG. 5) in sera of the DOCK8$^{+/-}$ AND Tg mice and the DOCK8$^{-/-}$ AND Tg mice at 6 weeks of age (n=13), 12 weeks of age (n=8 and 9), and 18 weeks of age (n=4). The line in the graph indicates the average value, and the symbol "*" indicates that there is a significant difference at a risk ratio of less than 5%.

As a result, the concentrations of IgE in the serum increased in DOCK8$^{-/-}$ AND Tg mice at 12 weeks of age and 18 weeks of age, but the concentration of IgG2b in the serum did not increase.

Experimental Example 5

The concentrations of IL-31 in the sera of DOCK8$^{+/-}$ AND Tg mice and DOCK8$^{-/-}$ AND Tg mice were measured. FIG. 6 is a graph showing a concentration of IL-31 in the sera of the DOCK8$^{+/-}$ AND Tg mice and the DOCK8$^{-/-}$ AND Tg mice at 6 weeks of age (n=6) and 18 weeks of age (n=6). The line in the graph indicates the average value, and the symbol "**" indicates that there is a significant difference at a risk ratio of less than 1%.

As a result, the concentrations of IL-31 in the sera were significantly increased in 18-week-old DOCK8$^{-/-}$ AND Tg mice, compared to DOCK8$^{+/-}$ AND Tg mice (147.2±29.3 pg/mL vs. 41.5±28.6 pg/mL).

II. DOCK8 Negatively Regulates IL-31 Production in CD4$^+$ T Cells

Experimental Example 6

The IL-31 is produced mainly from activated CD4$^+$ T cells. The present inventors compared the immunological function of CD4$^+$ T cells of DOCK8$^{+/-}$ AND Tg mice and DOCK8$^{-/-}$ AND Tg mice.

FIG. 7 is the results of flow cytometry analysis for thymocytes and peripheral lymph node cells of DOCK8$^{+/-}$ AND Tg mice and DOCK8$^{-/-}$ AND Tg mice of 6 to 8 weeks of age. In addition, FIG. 8 is the results of flow cytometry analysis for spleen cells of DOCK8$^{+/-}$ AND Tg mice and DOCK8$^{-/-}$ AND Tg mice of 6 to 8 weeks of age.

As a result, it was revealed that development of T cells in the thymus is normal even when DOCK8 is deficient. However, as reported in DOCK8$^{-/-}$ mice, the proportion of T cells in peripheral lymph nodes and spleen was decreased in DOCK8$^{-/-}$ AND Tg mice. In addition, regardless of the DOCK8 expression, peripheral T cells were CD4$^+$ T cells expressing Vα11$^+$Vβ3$^+$ AND TCR.

Furthermore, the expression of CD44, which is an activation/memory marker in CD4$^+$ T cells, was similar in DOCK8$^{+/-}$ AND Tg and DOCK8$^{-/-}$ AND Tg mice at 6 to 8 weeks of age.

Experimental Example 7

The antigen-specific proliferation of CD4$^+$ T cells from DOCK8$^{+/-}$ AND Tg mice and DOCK8$^{-/-}$ AND Tg mice was investigated. FIG. 9 is a graph showing proliferation of CD4$^+$ T cells from DOCK8$^{+/-}$ AND Tg mice and DOCK8$^{-/-}$ AND Tg mice when they are stimulated with MCC peptide (SEQ ID NO: 1) in the presence of spleen cells of B10.BR mice expressing I-E$^κ$.

As a result, as shown in FIG. 9, it was revealed that the antigen-specific proliferation of CD4$^+$ T cells from DOCK8$^{+/-}$ AND Tg mice and DOCK8$^{-/-}$ AND Tg mice was in the comparable level.

Experimental Example 8

CD4$^+$ T cells from DOCK8$^{+/-}$ AND Tg mice and DOCK8$^{-/-}$ AND Tg mice were primarily stimulated with MCC peptide and expression of cytokine genes was examined.

(a) of FIG. 10 is a graph showing the expression of the IL-31 gene, (b) of FIG. 10 is a graph showing the expression of the IL-4 gene, and (c) of FIG. 10 is a graph showing the expression of IL-2 gene. In (a) to (c) of FIG. 10, the expression level of each gene was expressed as a relative value by setting the result of CD4$^+$ T cells from DOCK8$^{+/-}$ AND Tg mice as 1. In addition, the graph shows the average value±standard deviation of four independent experimental results. The symbol "*" in the drawing indicates that there is a significant difference at a risk ratio of less than 5%.

As a result, CD4$^+$ T cells from DOCK8$^{-/-}$ AND Tg mice showed increased IL-31 transcripts at 24 hours after antigenic stimulation compared to CD4$^+$ T cells derived from DOCK8$^{+/-}$ AND Tg mice. On the other hand, expression of the IL-2 gene was equivalent in CD4$^+$ T cells derived from DOCK8$^{+/-}$ AND Tg mice and CD4$^+$ T cells derived from DOCK8$^{-/-}$ AND Tg mice.

FIG. 11 is a graph showing the expression level of IL-31 gene in CD4$^+$ T cells from DOCK8$^{+/-}$ AND Tg mice and from DOCK8$^{-/-}$ AND Tg mice, after the secondary stimulation with anti-CD3c antibody and anti-CD28 antibody. Values in the drawing are relative values by setting the expression level of the IL-31 gene in CD4$^+$ T cells from DOCK8$^{+/-}$ AND Tg mice without secondary stimulation as 1. The graph shows the average value±standard deviation of three independent experimental results. The symbol "*" in the drawing indicates that there is a significant difference at a risk rate of less than 5%, and the symbol "**" indicates that there is a significant difference at a risk rate of less than 1%.

As shown in FIG. 11, the above effect due to DOCK8 deficiency became more prominent when activated CD4+ T cells were recovered 96 hours after antigen stimulation and re-stimulated with anti-CD3ε antibody.

The transcript of IL-31 reached 2860 times 3 hours after the secondary stimulation of CD4+ T cells from DOCK8$^{-/-}$ AND Tg mice, compared to the control sample without antigenic stimulation. This value was 27.3 times when the amount of IL-31 transcript in CD4+ T cells from DOCK8$^{+/-}$ AND Tg mice were similarly analyzed.

Experimental Example 9

Expression level of IL-31 protein after secondary stimulation of CD4+ T cells from DOCK8$^{+/-}$ AND Tg mice and DOCK8$^{-/-}$ AND Tg mice was measured by ELISA method.

FIG. 12 is a graph showing measurement results. The graph shows average value±standard deviation in representative results of three independent experiments measured in 3 wells. The symbol "**" in the drawing indicates that there is a significant difference at a risk ratio of less than 1%.

As a result, in agreement with the results of Experimental Example 8, it was revealed that CD4+ T cells from DOCK8$^{-/-}$ AND Tg mice produce large amounts of IL-31 upon antigen stimulation.

Experimental Example 10

As shown in (b) of FIG. 10, CD4+ T cells from the activated DOCK8$^{-/-}$ AND Tg mice increased the expression of IL-4 gene.

Then, the present inventors investigated the influence of IL-4 on the expression of the IL-31 gene in CD4+ T cells from DOCK8$^{+/-}$ AND Tg mice and DOCK8$^{-/-}$ AND Tg mice by treating them with anti-IL-4 antibody in primary stimulation. For this purpose, anti-IL-4 antibody was added to the medium during the primary stimulation of CD4+ T cells with MCC peptide.

FIG. 13 is a graph showing the expression level of the IL-31 gene. Values in the graph are relative values by setting the expression level of the IL-31 gene in CD4+ T cells from DOCK8$^{+/-}$ AND Tg mice without secondary stimulation as 1. The graph shows the average value±standard deviation of three independent experimental results. The symbol "**" in the drawing indicates that there is a significant difference at a risk ratio of less than 1%.

As a result, anti-IL-4 antibody treatment reduced the expression level of the IL-31 gene in both CD4+ T cells from DOCK8$^{+/-}$ AND Tg mice and DOCK8$^{-/-}$ AND Tg mice. However, the expression level of the IL-31 gene in CD4+ T cells from DOCK8$^{-/-}$ AND Tg mice was significantly higher than CD4+ T cells from DOCK8$^{+/-}$ AND Tg mice.

Based on the above result, it was revealed that DOCK8 negatively regulates IL-31 production by CD4+ T cells independently of IL-4 mediated signaling.

Experimental Example 11

In order to investigate whether the above findings can be extended to TCR with different antigen-specificity, the present inventors prepared and analyzed DOCK8$^{-/-}$ mice expressing OTII TCR which recognize the ovalbumin (OVA) peptide (SEQ ID NO: 4) presented by the I-A$^b$ molecule.

FIG. 14 is the results of flow cytometry analysis for peripheral lymph node cells of DOCK8$^{+/-}$ OTII Tg mice and DOCK8$^{-/-}$ OTII Tg mice of 6 to 8 weeks of age.

As a result, it was revealed that CD4+ T cells develop normally in DOCK8$^{-/-}$ OTII Tg mice as in DOCK8$^{-/-}$ AND Tg mice.

Experimental Example 12

Subsequently, the antigen-specific proliferation of CD4+ T cells from DOCK8$^{+/-}$ OTII Tg mice and DOCK8$^{-/-}$ OTII Tg mice was investigated. FIG. 15 is a graph showing proliferation of CD4+ T cells from DOCK8$^{+/-}$ OTII Tg mice and DOCK8-/- OTII Tg mice when they are stimulated with OVA peptide (SEQ ID NO: 4) in the presence of spleen cells of C57BL/6 mice expressing I-A$^b$.

As a result, as shown in FIG. 15, it was revealed that the antigen-specific proliferation of CD4+ T cells from DOCK8$^{+/-}$ OTII Tg mice and DOCK8$^{-/-}$ OTII Tg mice was in the comparable level.

Experimental Example 13

Subsequently, CD4+ T cells from DOCK8$^{+/-}$ OTII Tg mice and CD4+ T cells derived from DOCK8-/- OTII Tg mice were secondary stimulated and the expression level of the IL-31 gene was measured. FIG. 16 is a graph of showing the expression of the IL-31 gene. The expression level of the IL-31 gene was expressed as a relative value by setting the result of CD4+ T cells from DOCK8$^{+/-}$ OTII Tg mice as 1. The graph shows average value±standard deviation in representative results of three independent experiments. The symbol "*" in the drawing indicates that there is a significant difference at a risk ratio of less than 5%.

Experimental Example 14

Production of IL-31 protein after secondary stimulation of CD4+ T cells from DOCK8$^{+/-}$ OTII Tg mice and DOCK8$^{-/-}$ OTII Tg mice was measured by ELISA method.

FIG. 17 is a graph showing measurement results. The graph shows average value±standard deviation in representative results of three independent experiments measured in 2 wells. The symbol "**" in the drawing indicates that there is a significant difference at a risk ratio of less than 1%.

As shown in FIG. 16 and FIG. 17, it was revealed that CD4+ T cells from DOCK8-/- OTII Tg mice produce large amounts of IL-31 after secondary stimulation. These results indicate that DOCK8 generally acts as a negative regulator of IL-31 induction, regardless of the antigen specificity of CD4+ T cells.

Experimental Example 15

Subsequently, the concentrations of IL-31 in sera of 18-week-old DOCK8$^{+/-}$ OTII Tg mice (n=7) and DOCK8$^{-/-}$ OTII Tg mice (n=7) were compared.

FIG. 18 is a graph showing the concentration of IL-31 in sera of DOCK8$^{+/-}$ OTII Tg mice and DOCK8$^{-/-}$ OTII Tg mice. The lines in the graph indicate average values.

As a result, it became clear that, unlike DOCK8$^{-/-}$ AND Tg mice, DOCK8$^{-/-}$ OTII Tg mice showed no increase in IL-31 concentration in the serum.

Experimental Example 16

Subsequently, histological analysis of the skin of 18-week-old DOCK8$^{+/-}$ OTII Tg mice (n=4) and DOCK8$^{-/-}$ OTII Tg littermate mice (n=4) was performed.

(a) and (b) of FIG. 19 are photographs of the results of hematoxylin and eosin staining of the skin of 18-week-old DOCK8$^{+/-}$ OTII Tg mice ((a) of FIG. 19) and DOCK8-/- OTII Tg littermate mice ((b) of FIG. 19). Scale bar indicates 50 μm.

(c) of FIG. 19 is a graph showing the total number of inflammatory cells per 0.25 mm$^2$ in the skin of the DOCK8$^{+/-}$ OTII Tg mice (n=4) and the DOCK8$^{-/-}$ OTII Tg mice (n=4). Values in the graph represent average value±standard deviation.

As a result, it became clear that, unlike DOCK8$^{-/-}$ AND Tg mice, DOCK8$^{-/-}$ OTII Tg mice did not develop atopic dermatitis.

These results suggest that CD4$^+$ T cells of DOCK8$^{-/-}$ AND Tg mice are self-reactive T cells and are continuously stimulated by undefined autoantigens presented to I-A$^b$ molecules. That is, AND TCR is a TCR having self-reactivity.

III. Identification of EPAS1 as Master Control Factor of IL-31

Experimental Example 17

To clarify the mechanism of overexpression of IL-31 by CD4$^+$ T cells of DOCK8$^{-/-}$ AND Tg mice, the present inventors performed microarray analysis. As a result, it was revealed that 856 genes were highly expressed in CD4$^+$ T cells of DOCK8$^{-/-}$ AND Tg mice as compared with those in CD4$^+$ T cells of control DOCK8$^{+/-}$ AND Tg mice after antigen stimulation.

These genes contained 40 putative transcription factors, one of which was EPAS1. Therefore, the expression of the IL-31 gene was examined by overexpressing EPAS1 in wild-type CD4$^+$ T cells.

First, CD4$^+$ T cells of C57BL/6 mice were stimulated with plate-bound anti-CD3ε antibody and anti-CD28 antibody. Subsequently, the retroviral vector pMX-EPAS1-IRES-GFP and pMX-IRES-GFP (control) that encodes GFP with or without EPAS1, respectively, were introduced into CD4$^+$ T cells, and the expression of IL-31 gene expression was measured.

FIG. 20 is a graph showing the expression level of IL-31 gene. The values in the graph are relative values by setting the expression level of IL-31 gene in the control sample (pMX-IRES-GFP transfection group) as 1. The graph shows the average value±standard deviation (n=6) of three independent experimental results. The symbol "*" in the drawing indicates that there is a significant difference at a risk ratio of less than 5%.

As a result, the expression of the IL-31 gene following TCR stimulation was significantly increased in CD4$^+$ T cells overexpressing EPAS1, as compared with the control.

Experimental Example 18

The EPAS1 gene in CD4$^+$ T cells from DOCK8$^{-/-}$ AND Tg mice was knocked down and the influence thereof on the expression of IL-31 gene expression was examined.

After siRNA specific for EPAS1 or control siRNA was introduced into CD4$^+$ T cells from DOCK8$^{-/-}$ AND Tg mice, they were stimulated with antigen, and then the expression level of IL-31 gene was measured. The knockdown efficacy was examined by RT-PCR.

(a) of FIG. 21 is a graph showing the expression level of IL-31 gene. The values in the graph are relative values by setting the expression level of the IL-31 gene in cells without antigen stimulation as 1. The graph shows the average value±standard deviation of three independent experimental results. The symbol "*" in the drawing indicates that there is a significant difference at a risk ratio of less than 5%. (b) of FIG. 21 is a graph of the results of the RT-PCR.

As a result, it was revealed that knocking down EPAS1 gene significantly suppresses the expression of IL-31 gene in the CD4$^+$ T cells from DOCK8$^{-/-}$ AND Tg mice.

Experimental Example 19

Subsequently, the effect of the deletion of EPAS1 gene on IL-31 gene expression in CD4$^+$ T cells from DOCK8$^{-/-}$ AND Tg mice was examined.

Specifically, CD4-Cre$^+$ EPAS1$^{lox/lox}$DOCK8$^{-/-}$ AND Tg mice lacking EPAS1 genes specifically in T cells were generated, and the expression level of IL-31 gene in CD4$^+$ T cells from these mice was measured.

FIG. 22 is a graph showing the expression level of IL-31 gene. The values in the graph are relative values by setting the expression level of the IL-31 gene in cells without antigen stimulation as 1. The graph shows average value±standard deviation of the representative three independent experiments. In each experiment, the assays were performed with triplicate wells. The symbol "**" in the drawing indicates that there is a significant difference at a risk ratio of less than 1%.

As a result, deletion of the EPAS1 gene in CD4$^+$ T cells yielded the same result as in the case where EPAS1 gene was knocked down. That is, it was revealed that the expression of IL-31 gene in CD4$^+$ T cells from DOCK8$^{-/-}$ AND Tg mice was significantly suppressed by the deletion of EPAS1 gene.

Experimental Example 20

The incidence of atopic dermatitis, scratching behavior, and concentration of IL-31 in serum in CD4-Cre$^+$ EPAS1$^{lox/lox}$DOCK8$^{-/-}$ AND Tg mice were examined.

FIG. 23 is a representative photograph of 14-week-old CD4-Cre$^+$ EPAS1$^{lox/lox}$DOCK8$^{-/-}$ AND Tg mice and control littermate mice.

FIG. 24 is a graph showing quantitative measurements of scratching behaviors per 2 hours of the 14-week-old CD4-Cre$^+$ EPAS1$^{lox/lox}$DOCK8$^{--}$ AND Tg mice and the control littermate mice (n=4). Values in the graph represent average value±standard deviation. The symbol "**" in the drawing indicates that there is a significant difference at a risk ratio of less than 1%.

(a) of FIG. 25 shows photographs of the skin of the 14-week-old CD4-Cre$^+$ EPAS1$^{lox/lox}$DOCK8$^{-/-}$ AND Tg mice and the control littermate mice stained with hematoxylin and eosin. Scale bar indicates 50 μm.

(b) of FIG. 25 is a graph showing the total number of inflammatory cells per 0.25 mm$^2$ in the skin of the 14-week-old CD4-Cre$^+$ EPAS1$^{lox/lox}$DOCK8$^{-/-}$ AND Tg mice (n=4) and the control littermate mice (n=4). Values in the graph represent average value±standard deviation. The symbol "**" in the drawing indicates that there is a significant difference at a risk ratio of less than 1%.

FIG. 26 is a graph showing the concentration of IL-31 in sera of the 14-week-old CD4-Cre$^+$ EPAS1$^{lox/lox}$DOCK8$^{-/-}$ AND Tg mice (n=4) and the control littermate mice (n=4). The lines in the graph indicate average values. The symbol "**" in the drawing indicates that there is a significant difference at a risk ratio of less than 1%.

In FIGS. 23 to 26, CD4-Cre$^-$ EPAS1$^{lox/lox}$DOCK8$^{-/-}$ AND Tg mice or CD4-Cre$^+$ EPAS1$^{lox/w}$DOCK8$^{-/-}$ AND Tg mice were used as control mice.

Based on the above results, no increase in the concentration of IL-31 in the serum was observed in all the CD4-Cre$^+$ EPAS1$^{lox/lox}$DOCK8$^{-/-}$ AND Tg mice tested, and neither scratching behavior nor atopic dermatitis development was evident in CD4-Cre$^+$ EPAS1$^{lox/lox}$DOCK8$^{-/-}$ AND Tg mice.

Therefore, it was revealed that EPAS1 functions as a master regulator of IL-31 induction in CD4$^+$ T cells and is essential for the development of atopic dermatitis in DOCK8$^{-/-}$ AND Tg mice.

Experimental Example 21

Subsequently, how EPAS1 activates the promoter of IL-31 was examined.

The present inventors produced a reporter construct in which the luciferase gene was ligated downstream of the IL-31 promoter sequence (−1367 to −1). In addition, an expression vector of a mutant of EPAS1 was produced.

(a) of FIG. 27 is a schematic diagram of EPAS1 mutants used in the present experimental example. Subsequently, the reporter construct was transfected into mouse embryonic fibroblasts (MEF) with the gene encoding EPAS1 mutant and the activity of the IL-31 promoter was measured.

(b) of FIG. 27 is a graph showing the activity of IL-31 promoter in the presence of wild-type and mutant EPAS1. The value of the graph shows the average value±standard deviation of four independent experiments. The symbol "*" in the drawing indicates that there is a significant difference at a risk rate of less than 5%, and the symbol "**" indicates that there is a significant difference at a risk rate of less than 1%.

As a result, it became clear that activation of IL-31 promoter was induced in the presence of wild-type EPAS1. However, activation of IL-31 promoter was not induced by the mutant EPAS1 lacking the activation domain at the N-terminal side (N-TAD) or the activation domain at the C-terminal side (C-TAD).

Experimental Example 22

Subsequently, the reporter construct of Experimental Example 21 and the expression vector encoding wild-type EPAS1 with siRNA specific for Aryl hydrocarbon receptor nuclear translocator (ARNT) gene or siRNA specific for specificity protein 1 (SP1) gene were introduced into MEF, and the activity of IL-31 promoter was measured.

(a) of FIG. 28 is a graph showing the activity of the IL-31 promoter. The value of the graph shows the average value±standard deviation of three independent experimental results. The symbol "*" in the drawing indicates that there is a significant difference at a risk rate of less than 5%, and the symbol "*" indicates that there is a significant difference at a risk rate of less than 5%. (b) of FIG. 28 are photographs of Western blotting showing the efficacy of knockdown of ARNT gene. (c) of FIG. 28 are photographs of Western blotting showing the efficacy of knockdown of SP1 gene.

As a result, it was revealed that knockdown of the ARNT gene did not affect EPAS1-mediated IL-31 promoter activation. On the other hand, it was revealed that, EPAS1-mediated IL-31 promoter activation was decreased when the SP1 gene was knocked down.

The above results indicate that SP1, but not ARNT, is essential for EPAS1-mediated IL-31 promoter activation.

Experimental Example 23

Subsequently, the present inventors generated a reporter construct where the IL-31 promoter region used in Experimental Example 21 was deleted, and introduced it into MEF together with the expression vector encoding wild-type EPAS1 to measure the IL-31 promoter activation.

FIG. 29 is a graph showing the activity of IL-31 promoter. The value of the graph shows the average value±standard deviation of three independent experimental results. The symbol "**" in the drawing indicates that there is a significant difference at a risk ratio of less than 1%.

As a result, the present inventors identified a region important for EPAS1-mediated IL-31 promoter activation. This region contained "GCGC" at −118 to −115, which is consensus sequence of the SP1 binding site.

Experimental Example 24

Subsequently, the present inventors generated a reporter construct where a site-specific mutation was introduced into the IL-31 promoter, and introduced into MEF together with the expression vector encoding wild-type EPAS1 to measure IL-31 promoter activation.

FIG. 30 is a graph showing the activity of IL-31 promoter. The term "#1;CAA" in the drawing means that "TGG" positioned in the #1 region (−135 to −133) of the IL-31 promoter shown in the lower part of FIG. 30 was mutated to "CAA", and the same applies hereinafter. The value of the graph shows the average value±standard deviation of three independent experimental results. The symbol "**" in the drawing indicates that there is a significant difference at a risk ratio of less than 1%.

As a result, it became clear that mutation of the SP1 binding sequence "GCGC" located at −118 to −115 of the IL-31 promoter to "AAGT" results in nearly complete loss of EPAS1-mediated IL-31 promoter activation. This result shows that the SP1 binding sequence located at −118 to −115 is important for the EPAS1-mediated IL-31 promoter activation.

Experimental Example 25

Subsequently, whether SP1 binds to the IL-31 promoter was investigated by Electrophoretic mobility shift assay (EMSA).

(a) and (b) of FIG. 31 are photographs of the results of EMSA. In the drawing, the term "C" indicates SP1-DNA complex and the term "SS" indicates super shift. The term "NE" means nuclear extract, the term "WT" means wild type sequence, and the term "Mut" means mutant type sequence.

As a result, it became clear that SP1 was definitely bound to the IL-31 promoter. In addition, it was revealed that SP1 does not bind to a DNA fragment where "GCGC", the SP1 binding sequence located at −118 to −115 of the IL-31 promoter, was mutated to "AAGT".

Experimental Example 26

Subsequently, the effect of EPAS1 on the binding of SP1 to the IL-31 promoter was examined by chromatin immunoprecipitation (ChIP).

FIG. 32 is a graph of the results of ChIP assay. The value of the graph shows the average value±standard deviation of seven independent experimental results. The symbol "*" in the drawing indicates that there is a significant difference at a risk ratio of less than 5%.

As a result, it was revealed that the binding of SP1 to the IL-31 promoter was markedly decreased in the absence of EPAS1.

Based on the result, it became clear that the EPAS1 activates the IL-31 promoter independently of the ARNT, but in collaboration with the SP1.

The present inventors also carried out ChIP using CD4$^+$ T cells instead of MEF and examined the effect of EPAS1 on the binding of SP1 to the IL-31 promoter. As a result, even when CD4$^+$ T cells were used, the same results were obtained as seen in the MEFs. That is, it was revealed that the binding of SP1 to the IL-31 promoter was markedly decreased in the absence of EPAS1.

IV. DOCK8 Functions as Adapter to Control Nuclear Translocation of EPAS1

Experimental Example 27

EPAS1 translocates from the cytoplasm to the nucleus and mediates IL-31 promoter activation. Therefore, the present inventors examined the intracellular localization of EPAS1 among wild-type MEF and DOCK8$^{-/-}$ MEF in order to elucidate the mechanism by which DOCK8 negatively controls IL-31 induction.

First, anti-EPAS1 antibody was verified by immunofluorescence staining. (a) of FIG. 33 shows fluorescence microscopy photographs of EPAS1$^{-/-}$ MEF stained with anti-EPAS1 antibody. DAPI was used to stain the nucleus. Scale bar indicates 20 μm. (b) of FIG. 33 shows fluorescence microscopy photographs of wild-type MEF stained with the anti-EPAS1 antibody. As a result, the validity of anti-EPAS1 antibody was checked.

Subsequently, the intracellular localization of EPAS1 in wild-type (WT) and DOCK8$^{-/-}$ MEF under normal and hypoxia conditions was examined by immunofluorescence staining. (a) and (b) of FIG. 34 are fluorescence microscopy photographs of the immunofluorescence staining. DAPI was used to stain the nucleus. Scale bar indicates 20 μm. (c) of FIG. 34 is a graph showing the proportion of cells with nuclear localization of EPAS1. The value of the graph shows the average value±standard deviation of four independent experiments. The symbol "**" in the drawing indicates that there is a significant difference at a risk ratio of less than 1%.

As a result, EPAS1 was translocated to the nucleus under hypoxia in both wild-type and DOCK8$^{-/-}$ MEFs. In addition, the nuclear localization of EPAS1 in DOCK8$^{-/-}$ MEF was remarkably increased under normal conditions as compared with that in wild-type MEF.

Experimental Example 28

Mutant DOCK8 (ΔN and ΔDHR2) and wild-type DOCK8 (WT) were expressed in DOCK8$^{-/-}$ MEF and the subcellular localization of EPAS1 was examined.

(a) of FIG. 35 are fluorescence microscopy photographs showing intracellular localization of EPAS1 under normal and hypoxia conditions by immunofluorescence staining. DAPI was used to stain the nucleus. Scale bar indicates 20 μm. (b) of FIG. 35 is a graph showing the proportion of cells with nuclear localization of EPAS1. The value of the graph shows the average value±standard deviation of four independent experimental results. The symbol "*" in the drawing indicates that there is a significant difference at a risk rate of less than 5%, and the symbol "**" indicates that there is a significant difference at a risk rate of less than 1%.

As a result, it was revealed that accumulation of EPAS1 in the nucleus due to deletion of DOCK8 disappears by expressing wild-type DOCK8 in DOCK8$^{-/-}$ MEF. Similar results were also obtained when the DOCK8 mutant (ΔDHR2) lacking DOCK homology region (DHR)-2 domain essential for Cdc42 activation was expressed in DOCK8$^{-/-}$ MEF.

However, when the mutant (ΔN) lacking 527 amino acids at the N terminal of DOCK8 was expressed in DOCK8$^{-/-}$ MEF, accumulation of EPAS1 in the nucleus could not be suppressed. This result shows that the N-terminal region of DOCK8 is important for controlling intracellular localization of EPAS1.

Experimental Example 29

By the way, mammalian STE 20-like kinase 1 (MST 1) is a serine/threonine kinase involved in T cell adhesion, migration, proliferation, and apoptosis. As a result of searching for binding proteins, the present inventors revealed that DOCK8 binds to MST1 via N-terminal region thereof.

(a) of FIG. 36 is the result of immunoprecipitation showing that DOCK8 binds to MST1 via the N-terminal region.

Subsequently, DOCK8, MST1, and EPAS1 were co-expressed in 293T (HEK-293T) cells, human embryonic kidney cells, and immunoprecipitation was performed. (b) of FIG. 36 are photographs showing the result of immunoprecipitation. As a result, it became clear that EPAS1 and MST1 were co-immunoprecipitated irrespective of the presence of DOCK8.

This result suggests that DOCK8 binds to MST1, thereby regulating the intracellular localization of EPAS1.

Experimental Example 30

Subsequently, the effect of knockdown of MST1 gene on nuclear localization of EPAS1 in the nucleus was examined in wild-type MEF.

The shRNA of MST1 was introduced into wild-type MEF using pSUPER retro-puro sh MST1 retroviral vector, and MST1 was knocked down. FIG. 37 are photographs of the results showing the efficacy of knockdown of MST1 gene in Western blotting.

Subsequently, intracellular localization of EPAS1 under normal and hypoxia conditions was analyzed by immunofluorescence staining for wild-type (WT) MEF, DOCK8$^{-/-}$ MEF, and MEF where MST1 genes were knocked down.

(a) to (c) of FIG. 38 are fluorescence microscopy photographs of the results of the immunofluorescence staining. (a) of FIG. 38 shows results of wild-type MEF, (b) of FIG. 38 shows results of DOCK8$^{-/-}$ MEF, and (c) of FIG. 38 shows results of MEF where the MST 1 gene was knocked down. DAPI was used to stain the nucleus. Scale bar indicates 20 μm. (d) of FIG. 38 is a graph showing the proportion of cells with nuclear localization of EPAS1. The value of the graph shows the average value±standard deviation of three independent experimental results. The symbol "**" in the drawing indicates that there is a significant difference at a risk ratio of less than 1%.

As a result, it was revealed that knockdown of the MST1 gene markedly increases nuclear localization of EPAS1.

Experimental Example 31

The expression of the IL-31 gene was examined when MST1 gene was knocked down in CD4$^+$ T cells from DOCK8$^{+/-}$ AND Tg mice.

Following transfection of siRNA specific for MST1 and control siRNA into CD4$^+$ T cells from DOCK8$^{+/-}$ AND Tg mice, they were stimulated with antigen, and then the expression level of the IL-31 gene was measured. The knockdown efficacy was examined by RT-PCR.

(a) of FIG. 39 is a graph showing the expression level of IL-31 gene. The values in the graph are relative values by setting the expression level of the IL-31 gene in cells without antigen stimulation as 1. The graph shows the average value±standard deviation (n=4) of two independent experimental results. The symbol "" in the drawing indicates that there is a significant difference at a risk ratio of less than 1%. (b) of FIG. 39** is a graph of the results of the RT-PCR.

As a result, it was revealed that knocking down the MST1 gene significantly increased the expression of the IL-31 gene in CD4$^+$ T cells from DOCK8$^{+/-}$ AND Tg mice.

The above results indicate that the DOCK8-MST1 axis negatively regulates the induction of IL-31 by inhibiting the nuclear translocation of EPAS1.

V. Role of EPAS1 in CD4$^+$ T Cells of Patients with Atopic Dermatitis

Experimental Example 32

Since it became clear that EPAS1 is essential for the induction of IL-31 in murine CD4$^+$ T cells, the present inventors examined the role of EPAS1 in human CD4$^+$ T cells.

The CD4$^+$ T cells from the patients with atopic dermatitis and healthy volunteers were cultured for 6 hours in a 24-well plate coated with or without anti-CD3ε antibody, and the expression of DOCK8 was examined by Western blotting.

FIG. 40 shows photographs of the results of the Western blotting. As a result, no significant difference in the expression of DOCK8 between the patients with atopic dermatitis and healthy people (controls) was observed.

Experimental Example 33

Subsequently, the concentrations of IL-31 in sera of the patients with atopic dermatitis and healthy people (controls) were measured for comparison. FIG. 41 is a graph showing the concentration of IL-31 in serum (n=6). The lines in the graph indicate average values. The symbol "**" in the drawing indicates that there is a significant difference at a risk ratio of less than 1%.

As a result, it was revealed that the concentration of IL-31 in the serum of patients with atopic dermatitis was remarkably increased as compared with that of healthy controls.

Experimental Example 34

Subsequently, expression of cytokine genes in CD4$^+$ T cells following TCR stimulation was examined.

CD4$^+$ T cells from the patients with atopic dermatitis and healthy controls were stimulated with anti-CD3ε antibody, and expression levels of IL-31 gene and IL-2 gene were measured. (a) of FIG. 42 is a graph showing the expression level of the IL-31 gene. (b) of FIG. 42 is a graph showing the expression level of the IL-2 gene.

The values of the graph are relative values by setting the expression level of each cytokine gene in CD4$^+$ T cells from the healthy controls without TCR stimulation as 1; and the data show average value±standard deviation (n=6). The symbol "*" in the drawing indicates that there is a significant difference at a risk ratio of less than 5%.

As a result, as seen in the CD4$^+$ T cells from DOCK8$^{-/-}$ AND Tg mice, the expression level of IL-31 gene following TCR stimulation was remarkably high in the CD4$^+$ T cells from the patients with atopic dermatitis, compared to that in CD4$^+$ T cells from healthy controls, but the expression levels of the IL-2 gene were comparable.

Experimental Example 35

Subsequently, the present inventors examined the effect of EPAS1 inhibitor on IL-31 induction in CD4$^+$ T cells from the patients with atopic dermatitis. For this purpose, EPAS1 inhibitor, FM19G11 and HIFVII, were used. Although the precise mechanism has not been elucidated, FM19G11 is known to inhibit the expression of EPAS1.

First, the validity of anti-EPAS1 antibody was confirmed by Western blotting. Following expression of pcDNA-EPAS1-FLAG encoding FLAG-tagged human EPAS1 in HEK-293T cells, cell lysates were analyzed by the Western blotting using anti-FLAG antibody and anti-EPAS1 antibody. FIG. 43 shows photographs of the results of the Western blotting. As a result, the validity of anti-EPAS1 antibody was checked.

Subsequently, the influence of the EPAS1 inhibitor on the expression of EPAS1 in the CD4$^+$ T cells from the patients with atopic dermatitis and healthy controls was examined.

FIG. 44 shows photographs of the results of the Western blotting. The photographs show representative results of three independent experiments. As a result, it was confirmed that FM19G11 markedly decreased the expression level of EPAS1 protein in human CD4$^+$ T cells.

Experimental Example 36

Subsequently, the influence of EPAS1 inhibitors, FM19G11 (n=6) and HIFVII (n=3), on the cytokine gene expression in CD4$^+$ T cells from the patients with atopic dermatitis was examined following TCR stimulation.

(a) of FIG. 45 is a graph showing the effect of FM19G11 on the expression level of IL-31 gene. (b) of FIG. 45 is a graph showing the effect of FM19G11 on the expression level of the IL-2 gene. (c) of FIG. 45 is a graph showing the effect of HIFVII on the expression level of the IL-31 gene. In (a) to (c) of FIG. 45, the data in the graph are relative values by setting the expression level of each cytokine in CD4$^+$ T cells from the patients without TCR stimulation as 1. The graph shows the average value±standard deviation. The symbol "**" in the drawing indicates that there is a significant difference at a risk ratio of less than 1%.

As a result, when CD4$^+$ T cells from the patients with atopic dermatitis were treated with FM19G11, the expression of the IL-31 gene following TCR stimulation was markedly suppressed, but the expression levels of the IL-2 gene were comparable. On the other hand, when CD4$^+$ T cells from the patients with atopic dermatitis were treated with HIFVII, the inhibitory effect on IL-31 gene expression was not observed.

Experimental Example 37

It is known that HIFVII binds to the PAS-B domain of EPAS1 and inhibits the binding between EPAS1 and ARNT. In order to confirm the above description, ARNT and EPAS1 were co-expressed in HEK-293T cells, and immunoprecipitation was performed in the presence or absence of HIFVII. (a) and (b) of FIG. 46 are photographs showing the result of immunoprecipitation. As a result, it was confirmed that the HIFVII treatment inhibited binding of ARNT and EPAS1.

These results indicate that in the CD4$^+$ T cells from the patients with atopic dermatitis, EPAS1 regulates the induction of IL-31 gene irrespective of binding to ARNT.

VI. Atopic Dermatitis in DOCK8 Conditional Knockout Mice

Experimental Example 38

Whether conditional knockout mice where DOCK8 was specifically absent from CD4$^+$ T cells expressing AND TCR developed atopic dermatitis was investigated.

First, DOCK8$^{lox/lox}$ mice were produced by a standard method. Subsequently, DOCK8$^{lox/lox}$ mice were crossed with AND TCR Tg mice to obtain DOCK8$^{lox/lox}$ AND Tg mice. In addition, DOCK8$^{lox/lox}$ AND Tg mice were crossed with CD4-Cre Tg mice to obtain CD4-Cre$^+$DOCK8$^{lox/low}$ AND Tg mice.

DOCK8 was specifically absent from CD4$^+$ T cells in CD4-Cre$^+$DOCK8$^{lox/low}$ AND Tg mice. CD4-Cre$^+$DOCK8$^{lox/low}$ AND Tg mice were maintained under specific-pathogen-free (SPF) conditions and the incidence of dermatitis was examined. Age- and sex-matched littermates were used as controls.

The state of dermatitis was evaluated according to the Severity Scoring of Atopic Dermatitis (SCORAD) index. Specifically, four items of (1) erythema/hemorrhage, (2) scaling/dryness, (3) edema, and (4) excoriation/erosion were scored as 0: absence, 1: mild, 2: moderate, and 3: severe with scores of total 12 points were evaluated.

FIG. 47 is a graph showing the change in the SCORAD index of DOCK8 conditional knockout mice (KO, n=4) and control mice (heterozygosity, n=4). The values in the graph represent average value±standard deviation.

As a result, it became clear that the DOCK8 conditional knockout mice developed atopic dermatitis after 7 weeks of age, whereas the control mice did not develop dermatitis.

This result further supports that the gene mutation by which tri-molecular complex comprising DOCK8 protein, MST1 protein, and EPAS1 protein is not formed in the CD4$^+$ T cells causes development of atopic dermatitis.

VII. Investigation of CD4$^+$ T Cells Derived from DOCK8$^{-/-}$ OTII Tg Mice

Experimental Example 39

In Experimental Example 16, it is indicated that DOCK8$^{-/-}$ OTII Tg mice do not develop atopic dermatitis. Therefore, CD4$^+$ T cells from DOCK8$^{-/-}$ OTII Tg mice were adoptively transferred into CAG-OVA mice expressing the OVA antigen systemically, and whether itching was induced was investigated.

Specifically, first, CD4$^+$ T cells from DOCK8$^{+/-}$ OTII Tg mice or littermate DOCK8$^{-/-}$ OTII Tg mice were cultured in the presence of OVA 323-339 peptide (SEQ ID NO: 4, 1 µg/mL) with T cell-depleted, irradiated spleen cells (5×10$^6$ cells/well). Subsequently, activated CD4$^+$ T cell from each mice were intravenously administered to CAG-OVA mice at a dose of 5.7×10$^6$ cells/mouse. Subsequently, observation of the scratching behaviors started 5 hours after the administration of the cells.

FIG. 48 is a graph showing quantitative measurements of scratching behaviors per 2 hours of CAG-OVA mice transferred with CD4$^+$ T cells from DOCK8$^{+/-}$ OTII Tg mice or with CD4$^+$ T cells from the DOCK8$^{-/-}$ OTII Tg mice (n=4 for each group). Values in the graph represent average value±standard deviation. The symbol "*" in the drawing indicates that there is a significant difference at a risk ratio of less than 5%.

As a result, as shown in FIG. 48, it was revealed that the CAG-OVA mice transferred with CD4$^+$ T cells from DOCK8$^{-/-}$ OTII Tg mice exhibit severe scratching behavior. This result indicates that itching can be induced by transferring CD4$^+$ T cells from DOCK8$^{-/-}$ OTII Tg mice into the CAG-OVA mice.

INDUSTRIAL APPLICABILITY

According to the present invention, it is possible to clarify the mechanism regulating IL-31 production and provide an atopic dermatitis model non-human animal.

The invention claimed is:

1. A transgenic mouse whose genome comprises (i) a homozygous inactivation of the endogenous dedicator of cytokinesis 8 (DOCK8) gene such that a complex comprising DOCK8 protein, mammalian STE20-like kinase 1 (MST1) protein, and endothelial PAS domain protein 1 (EPAS1) protein is not formed in CD4+ T cells of said mouse, and (ii) a nucleic acid encoding AND, wherein AND is a rearranged T-cell receptor (TCR) that is expressed in said mouse, wherein said mouse spontaneously develops atopic dermatitis, exhibits higher scratching behavior, higher IL-31 expression, and epidermal hyperplasia accompanied with infiltration of CD4+ T cells and hyperkeratosis in the skin as compared to wild type mouse.

2. A method for screening a candidate therapeutic agent for atopic dermatitis, comprising:
   (i) administering a test agent to the transgenic mouse of claim 1;
   (ii) quantitatively measuring a degree of scratching behavior present in the transgenic mouse administered with the test agent; and
   (iii) determining that the test substance is the candidate therapeutic agent for atopic dermatitis when the quantitatively determined degree of the scratching behavior is decreased, as compared to a degree of the scratching behavior of the transgenic mouse not receiving the test agent.

* * * * *